US008697374B2

(12) United States Patent
Rajagopal et al.

(10) Patent No.: US 8,697,374 B2
(45) Date of Patent: Apr. 15, 2014

(54) **ANTIBODIES TO *CLOSTRIDIUM DIFFICILE* SPORES AND USES THEREOF**

(75) Inventors: Raj Rajagopal, Woodbury, MN (US); Ai-Ping Wei, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 377 days.

(21) Appl. No.: 12/919,254

(22) PCT Filed: Feb. 25, 2009

(86) PCT No.: PCT/US2009/035050
§ 371 (c)(1),
(2), (4) Date: Mar. 28, 2011

(87) PCT Pub. No.: WO2009/108652
PCT Pub. Date: Sep. 3, 2009

(65) Prior Publication Data
US 2011/0183360 A1    Jul. 28, 2011

Related U.S. Application Data

(60) Provisional application No. 61/032,270, filed on Feb. 28, 2008.

(51) Int. Cl.
*G01N 33/554* (2006.01)
*G01N 33/569* (2006.01)

(52) U.S. Cl.
USPC ........................................................ 435/7.32

(58) Field of Classification Search
None
See application file for complete search history.

(56) References Cited

U.S. PATENT DOCUMENTS

| | | | |
|---|---|---|---|
| 4,530,833 A | 7/1985 | Wilkins et al. | 424/92 |
| 4,533,630 A | 8/1985 | Wilkins et al. | 435/7 |
| 4,741,900 A | 5/1988 | Alvarez et al. | 424/85 |
| 4,863,852 A | 9/1989 | Wilkins et al. | 435/7 |
| 4,879,218 A | 11/1989 | Wilkins et al. | 435/7 |
| 5,223,409 A | 6/1993 | Ladner et al. | 435/69 |
| 5,231,003 A | 7/1993 | Coughlin et al. | 435/7 |
| 5,610,023 A | 3/1997 | Deutsch | 435/7 |
| 5,753,517 A | 5/1998 | Brooks et al. | |
| 5,876,960 A | 3/1999 | Rosen | 435/39 |
| 5,965,375 A | 10/1999 | Valkirs | 435/7 |
| 6,485,982 B1 | 11/2002 | Charlton | 436/514 |
| 6,498,041 B1 | 12/2002 | Tabacco et al. | 436/172 |
| 6,503,722 B1 | 1/2003 | Valkirs | 435/7 |
| 6,509,196 B1 | 1/2003 | Brooks et al. | 436/514 |
| 6,815,178 B1 | 11/2004 | Shoaf | 435/34 |
| 6,939,548 B2 | 9/2005 | Wilkins et al. | 424/247 |
| 6,974,573 B2 | 12/2005 | Lee | 424/184 |
| 7,074,454 B1 | 7/2006 | Lee | 426/580 |
| 7,179,611 B2 | 2/2007 | Deutsch | 435/7 |
| 7,189,522 B2 | 3/2007 | Esfandiari | 435/7 |
| RE39,664 E | 5/2007 | Gordon et al. | 436/161 |
| 7,306,942 B1 | 12/2007 | Shoaf | 435/288 |
| 2003/0018170 A1 | 1/2003 | Deutsch | 530/350 |
| 2003/0138876 A1 | 7/2003 | Ponce et al. | 435/34 |
| 2003/0175318 A1 | 9/2003 | Schilling et al. | 424/405 |
| 2004/0014154 A1 | 1/2004 | Ponce et al. | 435/7 |
| 2004/0033546 A1 | 2/2004 | Wang | 435/7 |
| 2004/0039165 A1 | 2/2004 | Fairweather et al. | 530/350 |
| 2005/0136508 A1 | 6/2005 | Ponce | 435/34 |
| 2005/0220783 A1 | 10/2005 | Lee | 424/130 |
| 2006/0275920 A1 | 12/2006 | Petrilla et al. | 436/514 |

FOREIGN PATENT DOCUMENTS

| | | | |
|---|---|---|---|
| EP | 0 209 273 | 1/1987 | G01N 33/569 |
| WO | WO 86/02362 | 4/1986 | C07K 15/00 |
| WO | WO 90/02809 | 3/1990 | C12P 21/00 |
| WO | WO 91/17271 | 11/1991 | C12Q 1/70 |
| WO | WO 91/18293 | 11/1991 | G01N 33/554 |
| WO | WO 92/01047 | 1/1992 | C12N 15/00 |
| WO | WO 92/09690 | 6/1992 | C12N 15/00 |
| WO | WO 92/15679 | 9/1992 | C12N 15/10 |
| WO | WO 92/18619 | 10/1992 | C12N 7/01 |
| WO | WO 92/20791 | 11/1992 | C12N 15/00 |
| WO | WO 93/01288 | 1/1993 | C12N 15/13 |
| WO | WO 98/45706 | 10/1998 | G01N 33/554 |
| WO | WO 99/02188 | 1/1999 | A61K 39/395 |
| WO | WO 01/32713 | 5/2001 | C07K 16/04 |
| WO | WO 2004/017899 | 3/2004 | |
| WO | WO 2004/069848 | 8/2004 | |
| WO | WO 2007/021485 | 2/2007 | G01J 3/44 |

OTHER PUBLICATIONS

Aronsson, B. et al.; "Enzyme-Linked Immunosorbent Assay (ELISA) for Antibodies to *Clostridium difficile* Toxins in Patients with Pseudomembranous Colitis and Antibiotic-Associated Diarrhoea"; Journal of Immunological Methods; vol. 60, No. 3; 1983; pp. 341-350.

Aronsson, B. et al.; "Enzyme Immunoassay for Detection of *Clostridium difficile* Toxins A and B in Patients with Antibiotic-Associated Diarrhoea and Colitis"; Eur. J. Clin. Microbiol.; vol. 4, No. 2; 1985; pp. 102-107.

Aronsson, B. et al.; "Serum Antibody Response to *Clostridium difficile* Toxins in Patients with *Clostridium difficile* Diarrhoea"; Infection; vol. 13, No. 3; 1985; pp. 97-101.

Ausubel, F.M. et al.; Current Protocols in Molecular Biology, vol. 1, Green Publishing Associates, Inc. and John Wiley & Sons, Inc., NY, 1994 p. 2.10.3 entitled Hybridization Analysis of DNA Blots (also Title, Copyright and table of contents pages—15 pgs).

Broussolle, V. et al.; "Molecular and Physiological Characterisation of Spore Germination in *Clostridium botulinum* and *C. sporogenes*"; Anaerobe; vol. 8, No. 3; 2002; pp. 89-100.

Cappuccino, J.G. et al.; Microbiology: A Laboratory Manual, Seventh Edition, 2005, (Title, Copyright and table of contents pages—6 pages).

(Continued)

*Primary Examiner* — Gary Nickol
*Assistant Examiner* — Khatol Shahnan-Shah

(57) ABSTRACT

The present invention provides antibodies that bind to the endospore of the bacterium *Clostridium difficile*, methods of making such antibodies, and methods of using such antibodies, including methods of detecting *C. difficile* endospores.

3 Claims, 2 Drawing Sheets

(56) References Cited

OTHER PUBLICATIONS

Cerquetti, M. et al.; "Purification and characterization of an immunodominant 36 kDa antigen present on the cell surface of *Clostridium difficile*"; Microbial Pathogenesis.; vol. 13, No. 4; 1992; pp. 271-279.

Chothia, C. et al.; "Canonical Structures for the Hypervariable Regions of Immunoglobulins"; Journal of Molecular Biology; vol. 196, No. 4; 1987; pp. 901-917.

Davis L.G. et al.; Basic Methods in Molecular Biology; 1986, (Title, Copyright and table of contents pages—6 pages).

Delmee, M. et al.; "Serogrouping of *Clostridium difficile* Strains by Slide Agglutination"; Journal of Clinical Microbiology; vol. 21, No. 3; 1985; pp. 323-327.

Foerster, H.F. et al.; "Response of *Bacillus* Spores to Combinations of Germinative Compounds"; Journal of Bacteriology; vol. 91, No. 3; 1966; pp. 1168-1177.

"General information about *Clostridium Difficile*" [online] *Colstridium Difficile* Foundation; 1998-2002; (retrieved on Feb. 2, 2008 from www.cdiffsupport.com/aboutcdiff.html) ; 4 pgs.

Gianfrilli, P.J. et al.; "Cytotoxin and Enterotoxin Production by *Clostridium Difficile*"; Microbiologica; vol. 7, No. 4; 1984; pp. 375-379.

Goding, J.W.; Chapter 3—Production of Monoclonal Antibodies from Monoclonal Antibodies: Principles and Practice; Academic Press; 1986; pp. 59-103 (also Title, Copyright and table of contents pages).

Gould, G.W., "Germination and the Problem of Dormancy" (Symposium on Bacterial Spores: Paper IV); J. Appl. Bact; vol. 33, No. 1; 1970; pp. 34-49.

Harlow, E. et al.; Antibodies—A Laboratory Manual; Cold Spring Harbor Laboratory; Cold Spring Harbor, NY; 1988; (Title, Copyright and table of contents pages—10 pages).

Heard, S.R. et al.; "Immunoblotting to Demonstrate Antigenic and Immunogenic Differences among Nine Standard Strains of *Clostridium difficile*"; Journal of Clinical Microbiology; vol. 24, No. 3; 1986; pp. 384-387.

Holliger, P. et al.; ""Diabodies": Small bivalent and bispecific antibody fragments"; Proc. Natl. Acad. Sci., USA; vol. 90; 1993; pp. 6444-6448.

Jeong, D.S. et al.; "Simultaneous Quantitative Determination of Multiple Analytes with Fluorescence-Tagged Probes by Immunochromatography"; Korean J. Biol. Sci.; vol. 7, No. 1; 2003; pp. 89-92.

Jones, P.T. et al.; "Replacing the complementarity-determining regions in a human antibody with those from a mouse"; Nature; vol. 321; 1986; pp. 522-525.

Kabat, E.A. et al.; Sequences of Proteins of Immunological Interest, Fifth Edition; U.S. Department of Health and Human Services; NIH Publication No. 91-3242; 1991; (Cover and table of contents pages—11 pgs).

Köhler G. et al.; "Derivation of specific antibody-producing tissue culture and tumor lines by cell fusion"; European Journal of Immunology; vol. 6, No. 7; 1976; pp. 511-519.

Kostelny, S.A. et al.; "Formation of a Bispecific Antibody by the Use of Leucine Zippers"; The Journal of Immunology; vol. 148, No. 5; 1992; pp. 1547-1553.

Kyne, L. et al.; "Asymptomatic Carriage of *Clostridium Difficile* and Serum Levels of IgG Antibody Against Toxin A"; The New England Journal of Medicine; vol. 342, No. 6; 2000; pp. 390-397.

Long, S.K. et al.; "Method for Removal of Vegetative Cells from Bacterial Spore Preparations"; J. Bacteriol; vol. 76, No. 3; 1958; p. 332.

Madigan, M.T. et al.; Tenth Edition—Brock Biology of Microorganisms; prentice Hall 2003, (Title, Copyright and table of contents pages—12 pages).

McFarland, L.V. et al.; "Noscomial Acquisition of *Clostridium Difficile* Infection"; New England Journal of Medicine; vol. 320, No. 4; 1989; pp. 204-210.

Merz, C.S. et al.; "Comparison of Four Commercially Available Rapid Enzyme Immunoassays with Cytotoxin Assay for Detection of *Clostridium difficile* Toxin(s) from Stool Specimens"; Journal of Clinical Microbiology; vol. 32, No. 5; 1994; pp. 1142-1147.

Moir, A. et al.; "The Genetics of bacterial Spore Germination"; Annu. Rev. Mirobiol.; vol. 44; 1990; pp. 531-553.

Moriyama, R. et al.; "Expression of a Germination-Specific Amidase, SIeB, of Bacilli in the Forespore Compartment of Sporulating Cells and Its Localization on the Exterior Side of the Cortex in Dormant Spores"; Journal of Bacteriology; vol. 181, No. 8; 1999; pp. 2373-2378.

Naclerio, G. et al.; "*Bacillus subtilis* Spore Coat Assembly Requires *cot*H Gene Expression"; Journal of Bacteriology; vol. 178, No. 15; 1996; pp. 4375-4380.

National Center for Biotechnology Information; National Library of Medicine, National Institutes of Health; GenBank Locus NZ__AAML04000007; Accession No. NZ__AAML04000007, "*Clostridium difficile* QCD-32g58 CdiffQ__04__7, whole genome shotgun sequence"; [online] Bethesda, MD (retrieved on Feb. 26, 2008 from www.ncbi.nlm.nih.gov/entrez/viewer.fcgi?db=nuccore&id=145955411); 236 pgs.

National Center for Biotechnology Information; National Library of Medicine, National Institutes of Health; GenBank Locus NZ__ABFD01000037; Accession No. NZ__ABFD01000037, "*Clostridium difficile* QCD-66c26 contig00122, whole genome shotgun sequence"; [online] Bethesda, MD (retrieved on Feb. 26, 2008 from www.ncbi.nlm.nih.gov/entrez/viewer.fcgi?db=nuccore&id=156628136) ; 24 pgs.

National Center for Biotechnology Information; National Library of Medicine, National Institutes of Health; GenPept Locus YP__001087502; Accession No. YP__001087502, "hypothetical protein CD1021 [*Clostridium difficile* 630]"; [online] Bethesda, MD (retrieved on Jan. 16, 2008 from www.ncbi.nlm.nih.gov/entrez/viewer.fcgi?db=protein&id=126698605); 2 pgs.

National Center for Biotechnology Information; National Library of Medicine, National Institutes of Health; GenPept Locus YP__001087516; Accession No. YP__001087516, "cell surface protein (putative N-acetylmuramoyl-L-alanine amidase) [*Clostridium difficile* 630]"; [online] Bethesda, MD (retrieved on Feb. 26, 2008 from www.ncbi.nlm.nih.gov/entrez/viewer.fcgi?db=protein&id=126698619); 3 pgs.

National Center for Biotechnology Information; National Library of Medicine, National Institutes of Health; GenPept Locus YP__001087517; Accession No. YP__001087517, "cell surface protein (putative N-acetylmuramoyl-L-alanine amidase) [*Clostridium difficile* 630]"; [online] Bethesda, MD (retrieved on Jan. 16, 2008 from www.ncbi.nlm.nih.gov/entrez/viewer.fcgi?db=protein&id=126698620); 3 pgs.

National Center for Biotechnology Information; National Library of Medicine, National Institutes of Health; GenPept Locus YP__001089297; Accession No. YP__001089297, "cell surface protein [*Clostridium difficile* 630]"; [online] Bethesda, MD (retrieved on Feb. 26, 2008 from www.ncbi.nlm.nih.gov/entrez/viewer.fcgi?db=protein&id=126700400); 3 pgs.

National Center for Biotechnology Information; National Library of Medicine, National Institutes of Health; GenPept Locus ZP__01802273; Accession No. ZP__01802273, "hypothetical protein CdifQ__04003247 [*Clostridium difficile* QCD-32g58]"; [online] Bethesda, MD (retrieved on Feb. 26, 2008 from www.ncbi.nlm.nih.gov/entrez/viewer.fcgi?db=protein&id=145953265); 2 pgs.

National Center for Biotechnology Information; National Library of Medicine, National Institutes of Health; GenPept Locus ZP__01804350; Accession No. ZP__01804350, "hypothetical protein CdifQ__04001133 [*Clostridium difficile* QCD-32g58]"; [online] Bethesda, MD (retrieved on Jan. 16, 2008 from www.ncbi.nlm.nih.gov/entrez/viewer.fcgi?db=protein&id=145955347); 2 pgs.

National Center for Biotechnology Information; National Library of Medicine, National Institutes of Health; GenPept Locus ZP__01804351; Accession No. ZP__01804351, "hypothetical protein CdifQ__04001134 [*Clostridium difficile* QCD-32g58]"; [online] Bethesda, MD (retrieved on Feb. 26, 2008 from www.ncbi.nlm.nih.gov/entrez/viewer.fcgi?db=protein&id=145955348); 2 pgs.

National Center for Biotechnology Information; National Library of Medicine, National Institutes of Health; GenPept Locus ZP__01804840; Accession No. ZP__01804840, "hypothetical protein

(56) References Cited

OTHER PUBLICATIONS

CdifQ_04001048 [*Clostridium difficile* QCD-32g58]"; [online] Bethesda, MD (retrieved on Feb. 26, 2008 from www.ncbi.nlm.nih.gov/entrez/viewer.fcgi?db=protein&id=145955839); 2 pgs.

National Center for Biotechnology Information; National Library of Medicine, National Institutes of Health; GenPept Locus ZP_01804841; Accession No. ZP_10804841, "hypothetical protein CdifQ_04001049 [*Clostridium difficile* QCD-32g58]"; [online] Bethesda, MD (retrieved on Feb. 26, 2008 from www.ncbi.nlm.nih.gov/entrez/viewer.fcgi?db=protein&id=145955840); 2 pgs.

National Center for Biotechnology Information; National Library of Medicine, National Institutes of Health; GenPept Locus ZP_05396381; Accession No. ZP_05396381, "hypothetical protein CdifQCD-04722 [*Clostridium difficile* QCD-37x79]"; [online] Bethesda, MD (retrieved on Nov. 10, 2011 from www.ncbi.nlm.nih.gov/protein/ZP_05396381); 1 pg.

Orlandi, R. et al.; Cloning Immunoglobulin variable domains for expression by the polymerase chain reaction; Proc. Natl. Acad. Sci. USA; vol. 86, No. 10; 1989; pp. 3833-3837.

Pantosti, A. et al.; "Immunoblot Analysis of Serum Immunoglobulin G Response to Surface Proteins of *Clostridium difficile* in Patients with Antibiotic-Associated Diarrhea"; Journal of Clinical Microbiology; vol. 27, No. 11; 1989; pp. 2594-2597.

Ponce, A.; "Species Specific Bacterial Spore Detection Using Lateral-Flow Immunoassay With DPA-Triggered Tb Luminescence"; National Aeronautics and Space Administration Tech Brief; vol. 27, No. 3 from JPL New Technology Report NPO-30469; Mar. 1, 2003; pp. 1-9.

Powers, E.M., "Method for Obtaining Free Bacterial Spores of *Bacillus subtilis var. niger*"; Applied Microbiology vol. 16, No. 1; 1968; pp. 180-181.

Sambrook, J. et al.; Molecular Cloning: A Laboratory Manual, Second Edition, Cold Spring Harbor Laboratory Press, Cold Spring Harbor, NY; 1989, (Title, Copyright and table of contents pages—30 pgs).

Sebaihia, M. et al.; "The multidrug-resistant human pathogen *Clostridium difficile* has a highly mobile, mosaic genome"; Nature Genetics; vol. 38, No. 7; 2006; pp. 779-786.

Singer, I. et al.; "Optimal Humanization of 1B4, and Anti-CD18 Murine Monoclonal Antibody, Is Achieved by Correct Choice of Human V-Region Framework Sequences"; The Journal of Immunology; vol. 150, No. 7; 1993; pp. 2844-2857.

Smith, G.P. et al.; "Phage Display"; Chemical Reviews; vol. 97, No. 2; 1997; pp. 391-410.

Songsivilai, S. et al.; "Bispecific antibody: a tool for diagnosis and treatment of disease"; Clin. Exp. Immunol.; vol. 79, No. 3; 1990; pp. 315-321.

Sorg, J. A. et al.; "Bile Salts and Glycine as Cogerminant for *Clostridium difficile* Spores"; Journal of Bacteriology; vol. 190, No. 7; 2008; pp. 2505-2512.

Stabler, R.A. et al.; "Comparative Phylogenomics of *Clostridium difficile* Reveals Clade Specificity and Microevolution of Hypervirulent Strains"; Journal of Bacteriology; vol. 188, No. 20; 2006; pp. 7297-7305.

Sullivan, N.M. et al.; "Purification and Characterization of Toxins A and B of *Clostridium difficile*"; Infection and Immunity; vol. 35, No. 3; 1982; pp. 1032-1040.

Takeda, S. et al.; "Construction of chimaeric processed immunoglobulin genes containing mouse variable and human constant region sequences"; Nature; vol. 314; 1985; pp. 452-454.

Thornton, C.R. et al.; "A One-Step, Immunochromatographic Lateral Flow Device Specific to *Rhizoctonia solani* and Certain Related Species, and Its Use to Detect and Quantify *R. solani* in Soil"; Phytopathology; vol. 94, No. 3; 2004; pp. 280-288.

Toma, S. et al.; "Serotyping of *Clostridium difficile*"; Journal of Clinical Microbiology; vol. 26, No. 3; 1988; pp. 426-428.

Traunecker, A. et al.; "Bispecific single chain molecules (Janusins) target cytotoxic lymphocytes on HIV infected cells"; The EMBO Journal; vol. 10; No. 12, 1991; pp. 3655-3659.

Traunecker, A. et al.; "Janusin: New Molecular Design for Bispecific Reagents"; Int J. Cancer: Supplement; vol. 7; 1992; pp. 51-52.

Viscidi, R. et al.; "Serum Antibody Response to Toxins A and B of *Clostridium difficile*"; The Journal of Infectious Diseases; vol. 148, No. 1; 1983; pp. 93-100.

Walpita, P. et al.; "Mannalian Epithelial Cell Line Kit for Detection of *Clostridium difficile* Toxin"; Journal of Clinical Microbiology; vol. 31, No. 2; 1993; pp. 315-317.

Wren, B.W.; "*Clostridium difficile* comes of age"; Future Microbiol.; vol. 1, No. 3; 2006; pp. 243-245.

Zilhão, R. et al.; "Assembly Requirements and Role of CotH during Spore Coat Formation in *Bacillus subtilis*"; Journal of Bacteriology; vol. 181, No. 8; 1999; pp. 2631-2633.

Quinlan, J.J. et al.; "Monoclonal Antibodies for Use in Detection of *Bacillus* and *Clostridium* Spores"; Applied and Environmental Microbiology; vol. 63, No. 2; 1997; pp. 482-487.

| SEQ ID NO.: | | |
|---|---|---|
| 1 | 1 | MDKKFTLLISIMIVFLCAVVGVYSTSSNKSVDLYSDVYIEKYFNRDKVMEVNIEIDESDLKDMNENAIKEEFKVAKVTVDGDTYCNVGIRTKGNSSLISVANSDSDRYSYKINFDKYNT |
| 23 | 1 | MDKKFTLLISIMIIFLCAVVGVYSTSSNKSVDLYSDVYIEKYFNRDKVMEVNIEIDESDLKDMNENAIKEEFKVAKVTVDGDTYCNVGIRTKGNSSLTSVANSDSDRYSYKINFDKYNT |
| 21 | 1 | .KIKKFTLLISIMIIFLCAVVGVYSTSSNKSVDLYSDVYIEKYFNRDKVMEVNIEIDESDLKDMNENAIKEEFKVAKVTVDGDTYCNVGIRTKGNSSLTSVANSDSDRYSYKINFDKYNT |
| 11 | 1 | ....MIIFLCAVVGVYSTSSNKSVDLYSDVYIEKYFNRDKVMEVNIEIDESDLKDMNENAIKEEFKVAKVTVDGDTYCNVGIRTKGNSSLTSVANSDSDRYSYKINFDKYNT |
| 12 | 1 | .............................................................. |
| 22 | 1 | .............................................................. |
| 38 | 1 | XXXXXXXXXXXXMIXFLCAVVGVYSTSSNKSVDLYSDVYIEKYFNRDKVMEVNIEIDESDLKDMNENAIKEEFKVAKVTVDGDTYCNVGIRTKGNSSLXSVANSDSDRYSYKINFDKYNT |
| 1 | 121 | SQSMEGLTQLNLNNCYSDPSYMREFLTYSICEEMGLATPEFAYAKVSINGEYHGLYLAVEGLKESYLENNFGNVTGDLYKSDEGSSLQYKGDDPESYSNLIVESDKKTADWSKITKLLKS |
| 23 | 121 | SQSMEGLTQLNLNNCYSDPSYMREFLTYSICEEMGLATPEFAYAKVSINGEYHGLYLAVEGLKESYLENNFGNVTGDLYKSDEGSSLQYKGDDPESYSNLIVESDKKTADWSKITKLLKS |
| 21 | 120 | SQSMEGLTQLNLNNCYSDPSYMREFLTYSICEEMGLATPEFAYAKVSINGEYHGLYLAVEGLKESYLENNFGNVTGDLYKSDEGSSLQYKGDDPESYSNLIVESDKKTADWSKITKLLKS |
| 11 | 109 | SQSMEGLTQLNLNNCYSDPSYMREFLTYSICEEMGLATPEFAYAKVSINGEYHGLYLAVEGLKESYLENNFGNVTGDLYKSDEGSSLQYKGDDPESYSNLIVESDKKTADWSKITKLLKS |
| 12 | 1 | .............................................................. |
| 22 | 1 | .............................................................. |
| 38 | 107 | SQSMEGLTQLNLNNCYSDPSYMREFLTYSICEEMGLATPEFAYAKVSINGEYHGLYLAVEGLKESYLENNFGNVTGDLYKSDEGSSLQYKGDDPESYSNLIVESDKKTADWSKITKLLKS |
| 1 | 241 | LDTGEDIEKYLDVDSVLKNIAINTALLNLDSYQGSFAHNYYLYEQDGVFSMLPWDFNMSFGGFGFGGGSQSIAIDEPTTGNLEDRPLISSLLKNETYKTKYHKYLEIVTKYLDSDYLE |
| 23 | 241 | LDTGEDIEKYLDVDSVLKNIAINTALLNLDSYQGSFAHNYYLYEQDGVFSMLPWDFNMSFGGFGFGGGSQSIAIDEPTTGNLEDRPLISSLLKNETKITKYHKYLEEIVTKYLDSDYLE |
| 21 | 240 | LDTGEDIEKYLDVDSVLKNIAINTALLNLDSYQGSFAHNYYLYEQDGVFSMLPWDFNMSFGGFGFGGGSQSIAIDEPTTGNLEDRPLISSLLK.................. |
| 11 | 229 | LDTGEDIEKYLDVDSVLKNIAINTALLNLDSYQGSFAHNYYLYEQDGVFSMLPWDFNMSFGGFGFGGGSQSIAIDEPTTGNLEDRPLISSLLK.................. |
| 12 | 1 | .............................................................. |
| 22 | 1 | KNETHKTKYHKYLEEIVTKYLDSDYLE |
| 38 | 227 | LDTGEDIEKYLDVDSVLKNIAINTALLNLDSYQGSFAHNYYLYEQDGVFSMLPWDFNMSFGGFGFGGGSQSIAIDEPTTGNLEDRPLISSLLKXXXXXXXXXXXXXXXXXXXXXXXXXXX |

```
  1   361 NMTTKLHDMIASYVKEDPTAFYTYEEFEKNITSSIEDSSDNKGFGNKGFDNNNGNKGFDNNNSNSDSNNNGNSNSENKRSGNQSDEKEVNAELTSSVVKANTDNETEKNKTTNDSESKNNTDKDKSGNDNN
 23   361 NMTTKLHDMIASYVKEDPTAFYTYEEFEKNITSSIEDSSDNKGFGNKGFDNNNGNKGFDNNNSNSDSNNNGNSNSENKRSGNQSDKKEVNAELTSSVVKTNTDNETEENKTTNDSESKNNTDKDKSGNDNN
 21    ..............................................................................................................................
 11    ..............................................................................................................................
 12     1 .MTTKLHDMIASYVKEDPTAFYTYEEFEKNITSSIEDSSDNKGFGNKGFDNNNSNKGFDNNNSNSDSNNNSNSNSENKRSGNQSDKKEVNAELTSSVVKTNTDNETENKTTNDSESKNNTDKDKSGNDNN
 22    28 NMTTKLHDMIASYVKEDPTAFYTYEEFEKNITSSIEDSSDNKGFGNKGFDNNNSNKGFDNNNSNSDSNNNSNSNSENKRSGNQSDKKEVNAELTSSVVKTNTDNETENKTTNDSESKNNTDKDKSGNDNN
 38   321 XMTTKLHDMIASYVKEDPTAFYTYEEFEKNITSSIEDSSDNKGFGNKGFDNNNSNKGFDNNNSNSDSNNNSNSNSENKRSGNQSDKKEVNAELTSSVVKTNTDNETENKTTNDSESKNNTDKDKSGNDNN 1   481 QKLEGPMGKGGEKSIPGVLEVAEDMSKTIKSQLSGETSSTKQNSGDESSSGIKGSEKFDEDMSGMPEPPEGMDGKMPPGMGNMDKGDMNGKNGNMAMDRNQDNPREAGGFGMRGGGSVSKT
 23   481 QKLEGPRGKGGEKSIPGVLEVAEDMSKTIKSQLSGETSSTKQNSGDESSSGIKGSEKFDEDMSGMPEPPEGMDGKMPPGMGNMDKGDMNGKNGNMAMDRNQDNPREAGGFGMRGGGSVSKT
 21    ..............................................................................................................................
 11    ..............................................................................................................................
 12   120 QKLEGPRGKGGEKSIPGVLEVAEDMSKTIKSQLSGETSSTKQNSGDESSSGIKGSEKFDEDMSGMPEPPEGMDGKMPPGMGNMDKGDMNGKNGNMAMDRNQDNPREAGGFGMRGGGSVSKT
 22   148 QKLEGPRGKGGEKSIPGVLEVAEDMSKTIKSQLSGETSSTKQNSGDESSSGIKGSEKFDEDMSGMPEPPEGMDGKMPPGMGNMDKGDMENGKNGNMANGNMNMDRNQDNPREAGGFGMRGGGSVSKT
 38   440 QKLEGPRGKGGEKSIPGVLEVAEDMSKTIKSQLSGETSSTKQNSGDESSSGIKGSEKFDEDMSGMPEPPEGMDGKMPPGMGNMDKGDMNGKNGNMNMDRNQDNPREAGGFGMRGGGSVSKT 1   601 TTYFKLILGGASMIIMSIMLVGVSRVKRRRFIKSK
 23   601 TTYFKLILGGASMIIMSIMLVGVSRVKRRRFIKSK
 21    ..................................
 11    ..................................
 12   240 TTYFKLILGGASMIIMSIMLVGVSRVKRRRFIKSK
 22   268 TTYFKLILGGASMIIMSIMLVGVSRVKRRRFIKSK
 38   560 TTYFKLILGGASMIIMSIMLVGVSRVKRRRFIKSK
```

*Fig. 1b*

SEQUENCE LISTING

<160> NUMBER OF SEQ ID NOS: 50

<210> SEQ ID NO 1
<211> LENGTH: 635
<212> TYPE: PRT

<213> ORGANISM: Clostridium difficile

<400> SEQUENCE: 1

```
Met Lys Asp Lys Lys Phe Thr Leu Leu Ile Ser Ile Met Ile Val Phe
1               5                   10                  15

Leu Cys Ala Val Val Gly Val Tyr Ser Thr Ser Ser Asn Lys Ser Val
            20                  25                  30

Asp Leu Tyr Ser Asp Val Tyr Ile Glu Lys Tyr Phe Asn Arg Asp Lys
        35                  40                  45

Val Met Glu Val Asn Ile Glu Ile Asp Glu Ser Asp Leu Lys Asp Met
    50                  55                  60

Asn Glu Asn Ala Ile Lys Glu Glu Phe Lys Val Ala Lys Val Thr Val
65                  70                  75                  80

Asp Gly Asp Thr Tyr Gly Asn Val Gly Ile Arg Thr Lys Gly Asn Ser
                85                  90                  95

Ser Leu Ile Ser Val Ala Asn Ser Asp Ser Asp Arg Tyr Ser Tyr Lys
            100                 105                 110

Ile Asn Phe Asp Lys Tyr Asn Thr Ser Gln Ser Met Glu Gly Leu Thr
        115                 120                 125

Gln Leu Asn Leu Asn Asn Cys Tyr Ser Asp Pro Ser Tyr Met Arg Glu
130                 135                 140

Phe Leu Thr Tyr Ser Ile Cys Glu Glu Met Gly Leu Ala Thr Pro Glu
145                 150                 155                 160

Phe Ala Tyr Ala Lys Val Ser Ile Asn Gly Glu Tyr His Gly Leu Tyr
                165                 170                 175

Leu Ala Val Glu Gly Leu Lys Glu Ser Tyr Leu Glu Asn Asn Phe Gly
            180                 185                 190

Asn Val Thr Gly Asp Leu Tyr Lys Ser Asp Glu Gly Ser Ser Leu Gln
        195                 200                 205

Tyr Lys Gly Asp Asp Pro Glu Ser Tyr Ser Asn Leu Ile Val Glu Ser
210                 215                 220

Asp Lys Lys Thr Ala Asp Trp Ser Lys Ile Thr Lys Leu Leu Lys Ser
225                 230                 235                 240

Leu Asp Thr Gly Glu Asp Ile Glu Lys Tyr Leu Asp Val Asp Ser Val
                245                 250                 255

Leu Lys Asn Ile Ala Ile Asn Thr Ala Leu Leu Asn Leu Asp Ser Tyr
            260                 265                 270

Gln Gly Ser Phe Ala His Asn Tyr Tyr Leu Tyr Glu Gln Asp Gly Val
        275                 280                 285

Phe Ser Met Leu Pro Trp Asp Phe Asn Met Ser Phe Gly Gly Phe Ser
290                 295                 300

Gly Phe Gly Gly Gly Ser Gln Ser Ile Ala Ile Asp Glu Pro Thr Thr
305                 310                 315                 320

Gly Asn Leu Glu Asp Arg Pro Leu Ile Ser Ser Leu Leu Lys Asn Glu
                325                 330                 335

Thr Tyr Lys Thr Lys Tyr His Lys Tyr Leu Glu Glu Ile Val Thr Lys
            340                 345                 350

Tyr Leu Asp Ser Asp Tyr Leu Glu Asn Met Thr Thr Lys Leu His Asp
        355                 360                 365

Met Ile Ala Ser Tyr Val Lys Glu Asp Pro Thr Ala Phe Tyr Thr Tyr
370                 375                 380

Glu Glu Phe Glu Lys Asn Ile Thr Ser Ser Ile Glu Asp Ser Ser Asp
385                 390                 395                 400

Asn Lys Gly Phe Gly Asn Lys Gly Phe Asp Asn Asn Ser Asn Asn
```

```
                     405                 410                 415
Ser Asp Ser Asn Asn Ser Asn Ser Glu Asn Lys Arg Ser Gly Asn
            420                 425                 430

Gln Ser Asp Glu Lys Glu Val Asn Ala Glu Leu Thr Ser Ser Val Val
            435                 440                 445

Lys Ala Asn Thr Asp Asn Glu Thr Lys Asn Lys Thr Thr Asn Asp Ser
450                 455                 460

Glu Ser Lys Asn Asn Thr Asp Lys Asp Lys Ser Gly Asn Asp Asn Asn
465                 470                 475                 480

Gln Lys Leu Glu Gly Pro Met Gly Lys Gly Lys Ser Ile Pro Gly
            485                 490                 495

Val Leu Glu Val Ala Glu Asp Met Ser Lys Thr Ile Lys Ser Gln Leu
            500                 505                 510

Ser Gly Glu Thr Ser Ser Thr Lys Gln Asn Ser Gly Asp Glu Ser Ser
        515                 520                 525

Ser Gly Ile Lys Gly Ser Glu Lys Phe Asp Glu Asp Met Ser Gly Met
        530                 535                 540

Pro Glu Pro Pro Glu Gly Met Asp Gly Lys Met Pro Pro Gly Met Gly
545                 550                 555                 560

Asn Met Asp Lys Gly Asp Met Asn Gly Lys Asn Gly Asn Met Asn Met
                565                 570                 575

Asp Arg Asn Gln Asp Asn Pro Arg Glu Ala Gly Gly Phe Gly Asn Arg
                580                 585                 590

Gly Gly Gly Ser Val Ser Lys Thr Thr Thr Tyr Phe Lys Leu Ile Leu
                595                 600                 605

Gly Gly Ala Ser Met Ile Ile Met Ser Ile Met Leu Val Gly Val Ser
            610                 615                 620

Arg Val Lys Arg Arg Phe Ile Lys Ser Lys
625                 630                 635

<210> SEQ ID NO 2
<211> LENGTH: 100
<212> TYPE: PRT
<213> ORGANISM: Clostridium difficile

<400> SEQUENCE: 2

Ser Lys Thr Ile Lys Ser Gln Leu Ser Gly Glu Thr Ser Ser Thr Lys
1               5                   10                  15

Gln Asn Ser Gly Asp Glu Ser Ser Ser Gly Ile Lys Gly Ser Glu Lys
            20                  25                  30

Phe Asp Glu Asp Met Ser Gly Met Pro Glu Pro Pro Glu Gly Met Asp
        35                  40                  45

Gly Lys Met Pro Pro Gly Met Gly Asn Met Asp Lys Gly Asp Met Asn
    50                  55                  60

Gly Lys Asn Gly Asn Met Asn Met Asp Arg Asn Gln Asp Asn Pro Arg
65                  70                  75                  80

Glu Ala Gly Gly Phe Gly Asn Arg Gly Gly Gly Ser Val Ser Lys Thr
                85                  90                  95

Thr Thr Tyr Phe
            100

<210> SEQ ID NO 3
<211> LENGTH: 15
<212> TYPE: PRT
<213> ORGANISM: Clostridium difficile

<400> SEQUENCE: 3
```

```
Glu Gly Ser Ser Leu Gln Tyr Lys Gly Asp Asp Pro Glu Ser Tyr
1               5                   10                  15

<210> SEQ ID NO 4
<211> LENGTH: 15
<212> TYPE: PRT
<213> ORGANISM: Clostridium difficile

<400> SEQUENCE: 4

Leu Lys Asn Glu Thr Tyr Lys Thr Lys Tyr His Lys Tyr Leu Glu
1               5                   10                  15

<210> SEQ ID NO 5
<211> LENGTH: 677
<212> TYPE: PRT
<213> ORGANISM: Clostridium difficile

<400> SEQUENCE: 5

Met Leu Ser Lys Glu Ile Asn Met Arg Arg Asn Thr Lys Leu Leu Thr
1               5                   10                  15

Thr Gly Ile Leu Ser Met Ala Ile Val Ala Pro Thr Met Ala Phe Ala
            20                  25                  30

Thr Glu Ser Asn Ala Met Glu Asn Asn Ala Asp Leu Asn Ile Asn Leu
        35                  40                  45

Glu Lys Lys Ser Ile Val Leu Gly Ser Lys Ser Lys Val Ser Val Lys
50                  55                  60

Phe Lys Glu Lys Pro Asp Ala Asp Ser Ile Lys Leu Lys Tyr Lys Cys
65                  70                  75                  80

Tyr Asp Met Pro Leu Asn Thr Thr Leu Asn Tyr Asn Gln Ser Thr Gly
                85                  90                  95

Ala Tyr Glu Gly Ile Ile Asn Tyr Asn Lys Asp Pro Glu Tyr Leu Asn
            100                 105                 110

Val Trp Glu Leu Gln Gly Ile Thr Ile Asn Ser Lys Thr Asn Pro Lys
        115                 120                 125

Thr Leu Asn Arg Gln Asp Leu Glu Lys Met Gly Leu Asn Leu Lys Asp
130                 135                 140

Tyr Asn Val Thr Gln Glu Cys Ile Ile Glu Asp Ile Thr Ser Arg Lys
145                 150                 155                 160

Asp Val Asn Lys Tyr Leu Arg Lys Thr Ser Ser Pro Ile Thr Glu Leu
                165                 170                 175

Thr Gly Ser Asp Arg Tyr Glu Thr Ala Val Lys Ile Ser Lys Glu Gly
            180                 185                 190

Trp Lys Asn Gly Ser Asp Lys Val Val Ile Ile Asn Gly Asp Val Ser
        195                 200                 205

Ile Asp Gly Ile Ile Ser Thr Pro Leu Ala Thr Thr Tyr Asn Ala Pro
210                 215                 220

Ile Leu Leu Val Glu Lys Asn Asn Val Pro Asn Ser Val Lys Ser Glu
225                 230                 235                 240

Leu Lys Arg Leu Asn Pro Lys Asp Ile Ile Ile Gly Asp Glu Asn
                245                 250                 255

Ala Ile Ser Lys Thr Thr Ala Asn Gln Ile Lys Ser Thr Val Asn Ala
            260                 265                 270

Ser Gln Thr Arg Leu Asn Gly Ser Asn Arg Tyr Glu Thr Ser Leu Leu
        275                 280                 285

Ile Ala Lys Glu Ile Asp Lys Asn His Asp Val Glu Lys Val Tyr Ile
290                 295                 300
```

```
Thr Asn Ala Asn Gly Gly Glu Val Asp Ala Leu Thr Ile Ala Ala Lys
305                 310                 315                 320

Ala Gly Gln Asp Lys Gln Pro Ile Ile Leu Thr Asp Lys Asp Ser Ile
            325                 330                 335

Thr Asp Asn Thr Tyr Lys Trp Leu Lys Ser Glu Asp Leu Gln Asn Ala
        340                 345                 350

Tyr Phe Ile Gly Gly Pro Gln Met Ile Ser Thr Asn Val Ile Asn Lys
    355                 360                 365

Val Asn Gly Ile Thr Lys Asp Ser Val Thr Asn Asn Arg Val Tyr Gly
370                 375                 380

Ala Asp Arg His Glu Thr Asn Ala Asn Val Ile Lys Lys Phe Tyr Thr
385                 390                 395                 400

Asp Asp Glu Leu Glu Ala Val Leu Val Ala Lys Ser Asp Val Leu Val
            405                 410                 415

Asp Ala Leu Ala Ala Gly Pro Leu Ala Ala Asn Leu Lys Ser Pro Ile
        420                 425                 430

Leu Ile Thr Pro Lys Thr Tyr Val Ser Ala Tyr His Lys Asp Asn Leu
    435                 440                 445

Glu Ala Lys Ser Ala Asn Lys Val Tyr Lys Ile Gly Gly Gly Leu Thr
450                 455                 460

Ser Lys Val Met Ser Ser Ile Ala Ser Ser Leu Ser Lys His Asn Thr
465                 470                 475                 480

Thr Pro Thr Glu Pro Gly Asn Ser Gly Gly Lys Thr Val Met Ile Asp
            485                 490                 495

Pro Gly His Gly Gly Ser Ala Pro Gly Asn Ser Ser Gly Gly Met Ile
        500                 505                 510

Glu Lys Asp Tyr Asn Leu Asn Thr Ser Leu Ala Thr Thr Glu Tyr Leu
    515                 520                 525

Arg Ser Lys Gly Phe Asn Val Ile Met Thr Arg Asp Thr Asp Lys Thr
530                 535                 540

Leu Ser Leu Gly Asn Arg Thr Ala Leu Ser Asn Ser Leu Lys Pro Asp
545                 550                 555                 560

Leu Phe Thr Ser Ile His Tyr Asn Gly Ser Thr Asn Lys Gln Gly His
            565                 570                 575

Gly Val Glu Val Phe Tyr Lys Leu Lys Asp Lys Asn Gly Gly Thr Thr
        580                 585                 590

Lys Thr Val Ala Thr Asn Ile Leu Asn Arg Ile Leu Glu Lys Phe Lys
    595                 600                 605

Leu Thr Asn Arg Gly Ile Lys Thr Arg Val Leu Pro Ser Asp Ser Thr
610                 615                 620

Lys Asp Tyr Leu Tyr Val Leu Arg Ser Asn Asp Met Pro Ala Val Leu
625                 630                 635                 640

Val Glu Cys Ala Phe Leu Asp Asn Glu Asn Asp Met Ser Leu Ile Asn
            645                 650                 655

Ser Ser Ala Lys Val Lys Glu Met Gly Thr Gln Ile Gly Lys Gly Ile
        660                 665                 670

Glu Asp Ser Leu Lys
        675

<210> SEQ ID NO 6
<211> LENGTH: 99
<212> TYPE: PRT
<213> ORGANISM: Clostridium difficile

<400> SEQUENCE: 6
```

Asp Lys Asn His Asp Val Glu Lys Val Tyr Ile Thr Asn Ala Asn Gly
1               5                   10                  15

Gly Glu Val Asp Ala Leu Thr Ile Ala Lys Ala Gly Gln Asp Lys
            20                  25                  30

Gln Pro Ile Ile Leu Thr Asp Lys Asp Ser Ile Thr Asp Asn Tyr Lys
        35                  40                  45

Trp Leu Lys Ser Glu Asp Leu Gln Asn Ala Tyr Phe Ile Gly Gly Pro
    50                  55                  60

Gln Met Ile Ser Thr Asn Val Ile Asn Lys Val Asn Gly Ile Thr Lys
65              70                  75                  80

Asp Ser Val Thr Asn Asn Arg Val Tyr Gly Ala Asp Arg His Glu Thr
                85                  90                  95

Asn Ala Asn

<210> SEQ ID NO 7
<211> LENGTH: 15
<212> TYPE: PRT
<213> ORGANISM: Clostridium difficile

<400> SEQUENCE: 7

Tyr Lys Leu Lys Asp Lys Asn Gly Gly Thr Thr Lys Thr Val Ala
1               5                   10                  15

<210> SEQ ID NO 8
<211> LENGTH: 15
<212> TYPE: PRT
<213> ORGANISM: Clostridium difficile

<400> SEQUENCE: 8

Lys Phe Lys Glu Lys Pro Asp Ala Asp Ser Ile Lys Leu Lys Tyr
1               5                   10                  15

<210> SEQ ID NO 9
<211> LENGTH: 91
<212> TYPE: PRT
<213> ORGANISM: Clostridium difficile

<400> SEQUENCE: 9

Lys Ser Val Asp Leu Tyr Ser Asp Val Tyr Ile Glu Lys Tyr Phe Asn
1               5                   10                  15

Arg Asp Lys Val Met Glu Val Asn Ile Glu Ile Asp Glu Ser Asp Leu
            20                  25                  30

Lys Asp Met Asn Glu Asn Ala Ile Lys Glu Glu Phe Lys Val Ala Lys
        35                  40                  45

Val Thr Val Asp Gly Asp Thr Tyr Gly Asn Val Gly Ile Arg Thr Lys
    50                  55                  60

Gly Asn Ser Ser Leu Ile Ser Val Ala Asn Ser Asp Ser Asp Arg Tyr
65              70                  75                  80

Ser Tyr Lys Ile Asn Phe Asp Lys Tyr Asn Thr
                85                  90

<210> SEQ ID NO 10
<211> LENGTH: 100
<212> TYPE: PRT
<213> ORGANISM: Clostridium difficile

<400> SEQUENCE: 10

Val Thr Gly Asp Leu Tyr Lys Ser Asp Glu Gly Ser Ser Leu Gln Tyr
1               5                   10                  15

Lys Gly Asp Asp Pro Glu Ser Tyr Ser Asn Leu Ile Val Glu Ser Asp

```
            20                  25                  30
Lys Lys Thr Ala Asp Trp Ser Lys Ile Thr Lys Leu Leu Lys Ser Leu
         35                  40                  45

Asp Thr Gly Glu Asp Ile Glu Lys Tyr Leu Asp Val Asp Ser Val Leu
 50                  55                  60

Lys Asn Ile Ala Ile Asn Thr Ala Leu Leu Asn Leu Asp Ser Tyr Gln
 65                  70                  75                  80

Gly Ser Phe Ala His Asn Tyr Tyr Leu Tyr Glu Gln Asp Gly Val Phe
             85                  90                  95

Ser Met Leu Pro
            100

<210> SEQ ID NO 11
<211> LENGTH: 323
<212> TYPE: PRT
<213> ORGANISM: Clostridium difficile

<400> SEQUENCE: 11

Met Ile Ile Phe Leu Cys Ala Val Val Gly Val Tyr Ser Thr Ser Ser
 1               5                  10                  15

Asn Lys Ser Val Asp Leu Tyr Ser Asp Val Tyr Ile Glu Lys Tyr Phe
             20                  25                  30

Asn Arg Asp Lys Val Met Glu Val Asn Ile Glu Ile Asp Glu Ser Asp
         35                  40                  45

Leu Lys Asp Met Asn Glu Asn Ala Ile Lys Glu Glu Phe Lys Val Ala
 50                  55                  60

Lys Val Thr Val Asp Gly Asp Thr Tyr Gly Asn Val Gly Ile Arg Thr
 65                  70                  75                  80

Lys Gly Asn Ser Ser Leu Thr Ser Val Ala Asn Ser Asp Ser Asp Arg
             85                  90                  95

Tyr Ser Tyr Lys Ile Asn Phe Asp Lys Tyr Asn Thr Ser Gln Ser Met
            100                 105                 110

Glu Gly Leu Thr Gln Leu Asn Leu Asn Asn Cys Tyr Ser Asp Pro Ser
        115                 120                 125

Tyr Met Arg Glu Phe Leu Thr Tyr Ser Ile Cys Glu Glu Met Gly Leu
130                 135                 140

Ala Thr Pro Glu Phe Ala Tyr Ala Lys Val Ser Ile Asn Gly Glu Tyr
145                 150                 155                 160

His Gly Leu Tyr Leu Ala Val Glu Gly Leu Lys Glu Ser Tyr Leu Glu
            165                 170                 175

Asn Asn Phe Gly Asn Val Thr Gly Asp Leu Tyr Lys Ser Asp Glu Gly
        180                 185                 190

Ser Ser Leu Gln Tyr Lys Gly Asp Asp Pro Glu Ser Tyr Ser Asn Leu
        195                 200                 205

Ile Val Glu Ser Asp Lys Lys Thr Ala Asp Trp Ser Lys Ile Thr Lys
210                 215                 220

Leu Leu Lys Ser Leu Asp Thr Gly Glu Asp Ile Glu Lys Tyr Leu Asp
225                 230                 235                 240

Val Asp Ser Val Leu Lys Asn Ile Ala Ile Asn Thr Ala Leu Leu Asn
            245                 250                 255

Leu Asp Ser Tyr Gln Gly Ser Phe Ala His Asn Tyr Tyr Leu Tyr Glu
        260                 265                 270

Gln Asp Gly Val Phe Ser Met Leu Pro Trp Asp Phe Asn Met Ser Phe
        275                 280                 285

Gly Gly Phe Ser Gly Phe Gly Gly Gly Ser Gln Ser Ile Ala Ile Asp
```

```
                    290                 295                 300
Glu Pro Thr Thr Gly Asn Leu Glu Asp Arg Pro Leu Ile Ser Ser Leu
305                 310                 315                 320

Leu Lys Lys

<210> SEQ ID NO 12
<211> LENGTH: 274
<212> TYPE: PRT
<213> ORGANISM: Clostridium difficile

<400> SEQUENCE: 12

Met Thr Thr Lys Leu His Asp Met Ile Ala Ser Tyr Val Lys Glu Asp
1               5                   10                  15

Pro Thr Ala Phe Tyr Thr Tyr Glu Glu Phe Glu Lys Asn Ile Thr Ser
            20                  25                  30

Ser Ile Glu Asp Ser Ser Asp Asn Lys Gly Phe Gly Asn Lys Gly Phe
        35                  40                  45

Asp Asn Asn Asn Ser Asn Asn Ser Asp Ser Asn Asn Asn Ser Asn Ser
    50                  55                  60

Glu Asn Lys Arg Ser Gly Asn Gln Ser Asp Lys Lys Glu Val Asn Ala
65                  70                  75                  80

Glu Leu Thr Ser Ser Val Val Lys Thr Asn Thr Asp Asn Glu Thr Glu
                85                  90                  95

Asn Lys Thr Thr Asn Asp Ser Glu Ser Lys Asn Asn Thr Asp Lys Asp
            100                 105                 110

Lys Ser Gly Asn Asp Asn Asn Gln Lys Leu Glu Gly Pro Arg Gly Lys
        115                 120                 125

Gly Gly Lys Ser Ile Pro Gly Val Leu Glu Val Ala Glu Asp Met Ser
    130                 135                 140

Lys Thr Ile Lys Ser Gln Leu Ser Gly Glu Thr Ser Ser Thr Lys Gln
145                 150                 155                 160

Asn Ser Gly Asp Glu Ser Ser Ser Gly Ile Lys Gly Ser Glu Lys Phe
                165                 170                 175

Asp Glu Asp Met Ser Gly Met Pro Glu Pro Pro Glu Gly Met Asp Gly
            180                 185                 190

Lys Met Pro Pro Gly Met Gly Asn Met Asp Lys Gly Asp Met Asn Gly
        195                 200                 205

Lys Asn Gly Asn Met Asn Met Asp Arg Asn Gln Asp Asn Pro Arg Glu
    210                 215                 220

Ala Gly Gly Phe Gly Asn Arg Gly Gly Ser Val Ser Lys Thr Thr
225                 230                 235                 240

Thr Tyr Phe Lys Leu Ile Leu Gly Gly Ala Ser Met Ile Ile Met Ser
                245                 250                 255

Ile Met Leu Val Gly Val Ser Arg Val Lys Arg Arg Phe Ile Lys
            260                 265                 270

Ser Lys

<210> SEQ ID NO 13
<211> LENGTH: 999
<212> TYPE: DNA
<213> ORGANISM: Clostridium difficile

<400> SEQUENCE: 13
aagataaaaa aatttaccct tcttatctct attatgatta tattttatg tgctgtagtt      60 ggagtttata gtacatctag caacaaaagt gttgatttat atagtgatgt atatattgaa    120
```

-continued

| | |
|---|---|
| aaatattttta acagagacaa ggttatggaa gttaatatag agatagatga aagtgacttg | 180 |
| aaggatatga atgaaaatgc tataaaagaa gaatttaagg ttgcaaaagt aactgtagat | 240 |
| ggagatacat atggaaacgt aggtataaga actaaaggaa attcaagtct tacatctgta | 300 |
| gcaaatagtg atagtgatag atacagctat aagattaatt ttgataagta taatactagt | 360 |
| caaagtatgg aagggcttac tcaattaaat cttaataact gttactctga cccatcttat | 420 |
| atgagagagt ttttaacata tagtatttgc gaggaaatgg gattagcgac tccagaattt | 480 |
| gcatatgcta aagtctctat aaatggcgaa tatcatggtt tgtatttggc agtagaagga | 540 |
| ttaaaagagt cttatcttga aaataatttt ggtaatgtaa ctggagactt atataagtca | 600 |
| gatgaaggaa gctcgttgca atataaagga gatgacccag aaagttactc aaacttaatc | 660 |
| gttgaaagtg ataaaaagac agctgattgg tctaaaatta caaaactatt aaaatctttg | 720 |
| gatacaggtg aagatattga aaaatatctt gatgtagatt ctgtccttaa aaatatagca | 780 |
| ataaatacag cttttattaaa ccttgatagc tatcaaggca gttttgccca taactattat | 840 |
| ttatatgagc aagatggagt atttctatg ttaccatggg attttaatat gtcatttggt | 900 |
| ggatttagtg gttttggtgg aggtagtcaa tctatagcaa ttgatgaacc tacgacaggt | 960 |
| aatttagaag acagacctct catatcctcg ttattaaaa | 999 |

<210> SEQ ID NO 14
<211> LENGTH: 909
<212> TYPE: DNA
<213> ORGANISM: Clostridium difficile

<400> SEQUENCE: 14

| | |
|---|---|
| aaaaatgaga cacacaaaac aaaataccat aaatatctgg aagagatagt aacaaaatac | 60 |
| ctagattcag actatttaga gaatatgaca acaaaattgc atgacatgat agcatcatat | 120 |
| gtaaagaag acccaacagc atttttatact tatgaagaat ttgaaaaaaa tataacatct | 180 |
| tcaattgaag attctagtga taataaggga tttggtaata aagggtttga caacaataac | 240 |
| tctaataaca gtgattctaa taataattct aatagtgaaa ataagcgctc tggaaatcaa | 300 |
| agtgataaaa aagaagttaa tgctgaatta acatcaagcg tagtcaaaac taatacagat | 360 |
| aatgaaactg aaaataaaac tacaaatgat agcgaaagta agaataatac agataaagat | 420 |
| aaaagtggaa atgataataa tcaaaagcta gaaggtccta ggggtaaagg aggtaagtca | 480 |
| ataccagggg ttttggaagt tgcagaagat atgagtaaaa ctataaaatc tcaattaagt | 540 |
| ggagaaactt cttcgacaaa gcaaaactct ggtgatgaaa gttcaagtgg aattaaaggt | 600 |
| agtgaaaagt ttgatgagga tatgagtggt atgccagaac cacctgaggg aatggatggt | 660 |
| aaaatgccac caggaatggg taatatggat aaggagata tgaatggtaa aaatggcaat | 720 |
| atgaatatgg atagaaatca agataatcca agagaagctg gaggttttgg caatagagga | 780 |
| ggaggctctg tgagtaaaac aacaacatac ttcaaattaa ttttaggtgg agcttcaatg | 840 |
| ataataatgt cgattatgtt agtaggtgta tcaagggtaa agagaagaag atttataaag | 900 |
| tcaaaataa | 909 |

<210> SEQ ID NO 15
<211> LENGTH: 1907
<212> TYPE: DNA
<213> ORGANISM: Clostridium difficile

<400> SEQUENCE: 15

| | |
|---|---|
| atgaaagata aaaaatttac ccttcttatc tctattatga ttatattttt atgtgctgta | 60 |

-continued

```
ttggagttta tagtacatct agcaacaaaa gtgttgattt atatagtgat gtatatattg    120
aaaaatattt taacagagac aaggttatgg aagttaatat agagatagat gaaagtgact    180
tgaaggatat gaatgaaaat gctataaaag aagaatttaa ggttgcaaaa gtaactgtag    240
atggagatac atatggaaac gtaggtataa gaactaaagg aaattcaagt cttacatctg    300
tagcaaatag tgatagtgat agatacagct ataagattaa ttttgataag tataatacta    360
gtcaaagtat ggaagggctt actcaattaa atcttaataa ctgttactct gacccatctt    420
atatgagaga gtttttaaca tatagtattt gcgaggaaat gggattagcg actccagaat    480
ttgcatatgc taaagtctct ataaatggcg aatatcatgg tttgtatttg gcagtagaag    540
gattaaaaga gtcttatctt gaaaataatt ttggtaatgt aactggagac ttatataagt    600
cagatgaagg aagctcgttg caatataaag gagatgaccc agaaagttac tcaaacttaa    660
tcgttgaaag tgataaaaag acagctgatt ggtctaaaat tacaaaacta ttaaaatctt    720
tggatacagg tgaagatatt gaaaaatatc ttgatgtaga ttctgtcctt aaaaatatag    780
caataaatac agctttatta aaccttgata gctatcaagg cagttttgcc cataactatt    840
atttatatga gcaagatgga gtattttcta tgttaccatg ggattttaat atgtcatttg    900
gtggatttag tggttttggt ggaggtagtc aatctatagc aattgatgaa cctacgacag    960
gtaatttaga agacagacct ctcatatcct cgttattaaa aaatgagaca cacaaaacaa   1020
aataccataa atatctggaa gagatagtaa caaaatacct agattcagac tatttagaga   1080
atatgacaac aaaattgcat gacatgatag catcatatgt aaaagaagac ccaacagcat   1140
tttatactta tgaagaattt gaaaaaaata taacatcttc aattgaagat tctagtgata   1200
ataagggatt tggtaataaa gggtttgaca acaataactc taataacagt gattctaata   1260
ataattctaa tagtgaaaat aagcgctctg gaaatcaaag tgataaaaaa gaagttaatg   1320
ctgaattaac atcaagcgta gtcaaaacta atacagataa tgaaactgaa aataaaacta   1380
caaatgatag cgaaagtaag aataatacag ataaagataa aagtggaaat gataataatc   1440
aaaagctaga aggtcctagg ggtaaaggag gtaagtcaat accaggggtt ttggaagttg   1500
cagaagatat gagtaaaact ataaaatctc aattaagtgg agaaacttct tcgacaaagc   1560
aaaactctgg tgatgaaagt tcaagtggaa ttaaaggtag tgaaaagttt gatgaggata   1620
tgagtggtat gccagaacca cctgagggaa tggatggtaa aatgccacca ggaatgggta   1680
atatggataa gggagatatg aatggtaaaa atggcaatat gaatatggat agaaatcaag   1740
ataatccaag agaagctgga ggttttggca atagaggagg aggctctgtg agtaaaacaa   1800
caacatactt caaattaatt ttaggtggag cttcaatgat aataatgtcg attatgttag   1860
taggtgtatc aagggtaaag agaagaagat ttataaagtc aaaataa                 1907
```

<210> SEQ ID NO 16
<211> LENGTH: 679
<212> TYPE: PRT
<213> ORGANISM: Clostridium difficile

<400> SEQUENCE: 16

```
Met Leu Ser Lys Glu Ile Asn Met Arg Arg Asn Thr Lys Leu Leu Thr
1               5                   10                  15

Thr Gly Ile Leu Ser Met Ala Ile Val Thr Pro Thr Met Ala Phe Ala
            20                  25                  30

Thr Glu Ser Asn Ala Met Glu Asn Asn Ala Asp Leu Asn Ile Asn Leu
        35                  40                  45

Glu Lys Lys Ser Ile Val Leu Gly Ser Thr Ser Lys Val Ser Val Lys
```

-continued

```
            50                  55                  60
Phe Lys Glu Lys Pro Asp Ala Asp Ser Ile Thr Leu Lys Tyr Lys Cys
65                  70                  75                  80

Tyr Asp Met Pro Leu Asp Thr Thr Leu Asn Tyr Asn Gln Ser Thr Glu
                85                  90                  95

Ser Tyr Glu Gly Thr Ile Asn Tyr Asn Lys Asp Pro Glu Tyr Leu Asn
            100                 105                 110

Val Trp Glu Leu Gln Gly Ile Thr Ile Asn Ser Lys Asn Asn Pro Lys
            115                 120                 125

Thr Leu Asn Lys Gln Glu Leu Glu Lys Met Gly Leu Asn Leu Lys Asp
130                 135                 140

Tyr Asn Val Thr Gln Glu Cys Ile Ile Glu Asp Ile Thr Ser Arg Lys
145                 150                 155                 160

Asp Val Asn Lys Tyr Leu Arg Lys Thr Ser Ala Pro Ile Thr Glu Leu
                165                 170                 175

Thr Gly Ser Asp Arg Tyr Glu Thr Ala Val Lys Ile Ser Lys Glu Gly
            180                 185                 190

Trp Lys Asn Gly Ser Asp Lys Val Val Ile Asn Gly Asp Val Ser
            195                 200                 205

Ile Asp Gly Ile Ile Ser Thr Pro Leu Ala Thr Thr Tyr Asn Ala Pro
210                 215                 220

Ile Leu Leu Val Glu Lys Asn Asn Val Pro Asn Ser Val Lys Ser Glu
225                 230                 235                 240

Leu Lys Arg Leu Asn Pro Arg Asp Val Ile Ile Gly Asp Glu Asn
                245                 250                 255

Ala Ile Ser Lys Thr Thr Ala Asn Gln Ile Lys Ser Thr Val Asn Ala
            260                 265                 270

Ser Gln Thr Arg Leu Lys Gly Ser Asn Arg Tyr Glu Thr Ser Leu Leu
            275                 280                 285

Ile Ala Lys Glu Ile Asp Lys Asn His Asp Val Glu Lys Val Tyr Ile
            290                 295                 300

Thr Asn Ala Asn Gly Gly Glu Val Asp Ala Leu Thr Ile Ala Ala Lys
305                 310                 315                 320

Ala Gly Gln Asp Lys Gln Pro Ile Ile Leu Thr Asp Lys Asn Ser Ile
                325                 330                 335

Thr Asp Asn Thr Tyr Lys Trp Leu Lys Ser Glu Asp Leu Gln Asn Ala
            340                 345                 350

Tyr Phe Ile Gly Gly Pro Gln Met Ile Ser Thr Asn Val Ile Asn Lys
            355                 360                 365

Val Asn Asp Ile Thr Lys Asp Asn Val Thr Asn Asn Arg Val Tyr Gly
370                 375                 380

Ala Asp Arg His Glu Thr Asn Ala Asn Val Ile Lys Lys Phe Tyr Thr
385                 390                 395                 400

Asp Asp Glu Leu Glu Ala Val Leu Val Ala Lys Ser Asp Val Leu Val
                405                 410                 415

Asp Ala Leu Ala Ala Gly Pro Leu Ala Ala Asn Leu Lys Ser Pro Ile
            420                 425                 430

Leu Ile Thr Pro Lys Thr Tyr Val Ser Ala Tyr His Lys Glu Asn Leu
            435                 440                 445

Glu Ala Lys Ser Ala Asn Lys Val Tyr Lys Ile Gly Gly Gly Leu Thr
            450                 455                 460

Ser Lys Val Met Ser Ser Ile Ala Ser Ser Leu Ser Lys His Asn Thr
465                 470                 475                 480
```

-continued

```
Thr Pro Thr Glu Pro Gly Asn Ser Gly Gly Lys Thr Val Met Ile Asp
                485                 490                 495

Pro Gly His Gly Gly Ser Asp Thr Gly Thr Thr Gly Lys Pro Leu Gly
            500                 505                 510

Gly Ile Arg Glu Lys Asp Tyr Thr Leu Asn Thr Ser Leu Ala Thr Thr
        515                 520                 525

Glu Tyr Leu Arg Ser Lys Gly Phe Asn Val Ile Met Thr Arg Asp Thr
    530                 535                 540

Asp Lys Thr Leu Ser Leu Gly Asn Arg Thr Ala Leu Ser Asn Ser Leu
545                 550                 555                 560

Arg Pro Asp Leu Phe Thr Ser Ile His Tyr Asn Ala Ser Asp Thr Thr
                565                 570                 575

Gly Asn Gly Val Glu Val Phe Tyr Lys Leu Lys Asp Lys Asp Gly Gly
            580                 585                 590

Thr Thr Lys Thr Val Ala Thr Asn Ile Leu Asn Arg Ile Leu Glu Lys
        595                 600                 605

Phe Asn Leu Lys Asn Arg Gly Ala Lys Thr Arg Thr Leu Ser Thr Asp
    610                 615                 620

Pro Thr Lys Asp Tyr Leu Tyr Val Leu Arg Asn Asn Asp Met Pro Ala
625                 630                 635                 640

Val Leu Val Glu Cys Ala Phe Leu Asp Asn Glu Lys Asp Met Ser Leu
                645                 650                 655

Leu Asn Thr Ser Asn Lys Val Lys Glu Met Gly Thr Gln Ile Gly Lys
            660                 665                 670

Gly Ile Glu Asp Ser Leu Lys
        675

<210> SEQ ID NO 17
<211> LENGTH: 675
<212> TYPE: PRT
<213> ORGANISM: Clostridium difficile

<400> SEQUENCE: 17

Met Met Lys Lys Thr Thr Lys Leu Leu Ala Thr Gly Met Leu Ser Val
1               5                   10                  15

Ala Met Val Ala Pro Asn Val Ala Leu Ala Ala Glu Asn Thr Thr Ala
                20                  25                  30

Asn Thr Glu Ser Asn Ser Asp Ile Asn Ile Asn Leu Gln Arg Lys Ser
            35                  40                  45

Val Val Leu Gly Ser Lys Ser Asn Ala Ser Val Lys Phe Lys Glu Lys
        50                  55                  60

Leu Asn Ala Asp Ser Ile Thr Leu Asn Phe Met Cys Tyr Asp Met Pro
65                  70                  75                  80

Leu Glu Ala Thr Leu Asn Tyr Asn Glu Lys Thr Asp Ser Tyr Glu Gly
                85                  90                  95

Val Ile Asn Tyr Asn Lys Asp Pro Glu Tyr Leu Asn Val Trp Glu Leu
            100                 105                 110

Gln Ser Ile Lys Ile Asn Gly Lys Asp Glu Gln Lys Val Leu Asn Lys
        115                 120                 125

Glu Asp Leu Glu Ser Met Gly Leu Asn Leu Lys Asp Tyr Asp Val Thr
    130                 135                 140

Gln Glu Phe Ile Ile Ser Asp Ala Asn Ser Thr Lys Ala Val Asn Glu
145                 150                 155                 160

Tyr Met Arg Lys Thr Ser Ala Pro Val Lys Lys Leu Ala Gly Ala Thr
                165                 170                 175
```

```
Arg Phe Glu Thr Ala Val Glu Ile Ser Lys Gln Gly Trp Lys Asp Gly
            180                 185                 190

Ser Ser Lys Val Val Ile Val Asn Gly Glu Leu Ala Ala Asp Gly Ile
        195                 200                 205

Thr Ala Thr Pro Leu Ala Ser Thr Tyr Asp Ala Pro Ile Leu Leu Ala
    210                 215                 220

Asn Lys Asp Asp Ile Pro Glu Ser Thr Lys Ala Glu Leu Lys Arg Leu
225                 230                 235                 240

Asn Pro Ser Asp Val Ile Ile Ile Gly Asp Gly Ser Val Ser Gln
                245                 250                 255

Lys Ala Val Ser Gln Ile Lys Ser Ala Val Asn Val Asn Val Thr Arg
                260                 265                 270

Ile Gly Gly Val Asp Arg His Glu Thr Ser Leu Leu Ile Ala Lys Glu
            275                 280                 285

Ile Asp Lys Tyr His Asp Val Asn Lys Ile Tyr Ile Ala Asn Gly Tyr
            290                 295                 300

Ala Gly Glu Tyr Asp Ala Leu Asn Ile Ser Ser Lys Ala Gly Glu Asp
305                 310                 315                 320

Gln Gln Pro Ile Ile Leu Ala Asn Lys Asp Ser Val Pro Gln Gly Thr
                325                 330                 335

Tyr Asn Trp Leu Ser Ser Gln Gly Leu Glu Glu Ala Tyr Tyr Ile Gly
            340                 345                 350

Gly Ser Gln Ser Leu Ser Ser Lys Ile Ile Asp Gln Ile Ser Lys Ile
        355                 360                 365

Ala Lys Asn Gly Thr Ser Lys Asn Arg Val Ser Gly Ala Asp Arg His
    370                 375                 380

Glu Thr Asn Ala Asn Val Ile Lys Thr Phe Tyr Pro Asp Lys Glu Leu
385                 390                 395                 400

Ser Ala Met Leu Val Ala Lys Ser Asp Ile Ile Val Asp Ser Ile Thr
                405                 410                 415

Ala Gly Pro Leu Ala Ala Lys Leu Lys Ala Pro Ile Leu Ile Thr Pro
            420                 425                 430

Lys Thr Tyr Val Ser Ala Tyr His Ser Thr Asn Leu Ser Glu Lys Thr
        435                 440                 445

Ala Glu Thr Val Tyr Gln Ile Gly Asp Gly Met Lys Asp Ser Val Ile
    450                 455                 460

Asn Ser Ile Ala Ser Ser Leu Ser Lys His Asn Ala Pro Thr Glu Pro
465                 470                 475                 480

Asp Asn Ser Gly Ser Ala Ala Gly Lys Thr Val Val Ile Asp Pro Gly
                485                 490                 495

His Gly Gly Ser Asp Ser Gly Ala Thr Ser Gly Leu Asn Gly Gly Ala
            500                 505                 510

Gln Glu Lys Lys Tyr Thr Leu Asn Thr Ala Leu Ala Thr Thr Glu Tyr
        515                 520                 525

Leu Arg Ser Lys Gly Ile Asn Val Val Met Thr Arg Asp Thr Asp Lys
    530                 535                 540

Thr Met Ala Leu Gly Glu Arg Thr Ala Leu Ser Asn Thr Ile Lys Pro
545                 550                 555                 560

Asp Leu Phe Thr Ser Ile His Tyr Asn Ala Ser Asn Gly Ser Gly Asn
                565                 570                 575

Gly Val Glu Ile Tyr Tyr Lys Val Lys Asp Lys Asn Gly Gly Thr Thr
            580                 585                 590

Lys Thr Ala Ala Ser Asn Ile Leu Lys Arg Ile Leu Glu Lys Phe Asn
        595                 600                 605
```

```
Met Lys Asn Arg Gly Ile Lys Thr Arg Thr Leu Asp Asn Gly Lys Asp
    610                 615                 620
Tyr Leu Tyr Val Leu Arg Asn Asn Tyr Pro Ala Ile Leu Val Glu
625                 630                 635                 640
Cys Ala Phe Ile Asp Asn Lys Ser Asp Met Asp Lys Leu Asn Thr Ala
                    645                 650                 655
Glu Lys Val Lys Thr Met Gly Thr Gln Ile Gly Ile Gly Ile Glu Asp
                660                 665                 670
Thr Val Lys
        675

<210> SEQ ID NO 18
<211> LENGTH: 618
<212> TYPE: PRT
<213> ORGANISM: Clostridium difficile

<400> SEQUENCE: 18

Met Phe Arg Phe Lys Glu Lys Pro Asp Ala Asp Ser Ile Thr Leu Lys
1               5                   10                  15
Tyr Lys Cys Tyr Asp Met Pro Leu Asp Thr Thr Leu Asn Tyr Asn Gln
            20                  25                  30
Ser Thr Glu Ser Tyr Glu Gly Thr Ile Asn Tyr Asn Lys Asp Pro Glu
        35                  40                  45
Tyr Leu Asn Val Trp Glu Leu Gln Gly Ile Thr Ile Asn Ser Lys Asn
50                  55                  60
Asn Pro Lys Thr Leu Asn Lys Gln Glu Leu Lys Met Gly Leu Asn
65                  70                  75                  80
Leu Lys Asp Tyr Asn Val Thr Gln Glu Cys Ile Ile Glu Asp Ile Thr
                85                  90                  95
Ser Arg Lys Asp Val Asn Lys Tyr Leu Arg Lys Thr Ser Ala Pro Ile
            100                 105                 110
Thr Glu Leu Thr Gly Ser Asp Arg Tyr Glu Thr Ala Val Lys Ile Ser
        115                 120                 125
Lys Glu Gly Trp Lys Asn Gly Ser Asp Lys Val Val Ile Ile Asn Gly
    130                 135                 140
Asp Val Ser Ile Asp Gly Ile Ile Ser Thr Pro Leu Ala Thr Thr Tyr
145                 150                 155                 160
Asn Ala Pro Ile Leu Leu Val Glu Lys Asn Asn Val Pro Asn Ser Val
                165                 170                 175
Lys Ser Glu Leu Lys Arg Leu Asn Pro Arg Asp Val Ile Ile Ile Gly
            180                 185                 190
Asp Glu Asn Ala Ile Ser Lys Thr Thr Ala Asn Gln Ile Lys Ser Thr
        195                 200                 205
Val Asn Ala Ser Gln Thr Arg Leu Lys Gly Ser Asn Arg Tyr Glu Thr
    210                 215                 220
Ser Leu Leu Ile Ala Lys Glu Ile Asp Lys Asn His Asp Val Glu Lys
225                 230                 235                 240
Val Tyr Ile Thr Asn Ala Asn Gly Gly Glu Val Asp Ala Leu Thr Ile
                245                 250                 255
Ala Ala Lys Ala Gly Gln Asp Lys Gln Pro Ile Ile Leu Thr Asp Lys
            260                 265                 270
Asn Ser Ile Thr Asp Asn Thr Tyr Lys Trp Leu Lys Ser Glu Asp Leu
        275                 280                 285
Gln Asn Ala Tyr Phe Ile Gly Gly Pro Gln Met Ile Ser Thr Asn Val
    290                 295                 300
```

Ile Asn Lys Val Asn Asp Ile Thr Lys Asp Asn Val Thr Asn Asn Arg
305                 310                 315                 320

Val Tyr Gly Ala Asp Arg His Glu Thr Asn Ala Asn Val Ile Lys Lys
            325                 330                 335

Phe Tyr Thr Asp Asp Glu Leu Glu Ala Val Leu Val Ala Lys Ser Asp
            340                 345                 350

Val Leu Val Asp Ala Leu Ala Ala Gly Pro Leu Ala Asn Leu Lys
        355                 360                 365

Ser Pro Ile Leu Ile Thr Pro Lys Thr Tyr Val Ser Ala Tyr His Lys
        370                 375                 380

Asp Asn Leu Glu Ala Lys Ser Ala Asn Lys Val Tyr Lys Ile Gly Gly
385                 390                 395                 400

Gly Leu Thr Ser Lys Val Met Asn Ser Ile Ala Ser Ser Leu Ser Lys
                405                 410                 415

His Asn Thr Thr Pro Thr Glu Pro Gly Asn Ser Gly Gly Lys Thr Val
                420                 425                 430

Met Ile Asp Pro Gly His Gly Gly Ser Asp Thr Gly Thr Thr Gly Lys
        435                 440                 445

Pro Leu Gly Gly Ile Lys Glu Lys Asp Tyr Thr Leu Asn Thr Ser Leu
        450                 455                 460

Ala Thr Thr Glu Tyr Leu Arg Ser Lys Gly Phe Asn Val Ile Met Thr
465                 470                 475                 480

Arg Asp Thr Asp Lys Thr Leu Ser Leu Gly Asn Arg Thr Ala Leu Ser
                485                 490                 495

Asn Ser Leu Arg Pro Asp Leu Phe Thr Ser Ile His Tyr Asn Ala Ser
                500                 505                 510

Asp Thr Thr Gly Asn Gly Val Glu Val Phe Tyr Lys Leu Lys Asp Lys
        515                 520                 525

Asp Gly Gly Thr Thr Lys Thr Val Ala Thr Asn Ile Leu Asn Arg Ile
530                 535                 540

Leu Glu Lys Phe Asn Leu Lys Asn Arg Gly Ala Lys Thr Arg Thr Leu
545                 550                 555                 560

Ser Thr Asp Pro Thr Lys Asp Tyr Leu Tyr Val Leu Arg Asn Asn Asp
                565                 570                 575

Met Pro Ala Val Leu Val Glu Cys Ala Phe Leu Asp Asn Glu Lys Asp
        580                 585                 590

Met Ser Leu Leu Asn Thr Ser Asn Lys Val Lys Glu Met Gly Thr Gln
        595                 600                 605

Ile Gly Lys Gly Ile Glu Asp Ser Leu Lys
        610                 615

<210> SEQ ID NO 19
<211> LENGTH: 552
<212> TYPE: PRT
<213> ORGANISM: Clostridium difficile

<400> SEQUENCE: 19

Met Leu Ser Lys Glu Ile Asn Met Arg Arg Asn Thr Lys Leu Leu Thr
1               5                   10                  15

Thr Gly Ile Leu Ser Met Ala Ile Val Ala Pro Thr Met Ala Phe Ala
            20                  25                  30

Thr Glu Ser Asn Ala Met Glu Asn Asn Ala Asp Leu Asn Ile Asn Leu
        35                  40                  45

Glu Lys Lys Ser Ile Val Leu Gly Ser Lys Ser Lys Val Ser Val Lys
50                  55                  60

-continued

Phe Lys Glu Lys Pro Asp Ala Asp Ser Ile Thr Leu Lys Tyr Lys Cys
 65                  70                  75                  80

Tyr Asp Met Pro Leu Asp Thr Thr Leu Asn Tyr Asn Gln Ser Thr Gly
             85                  90                  95

Ala Tyr Glu Gly Thr Ile Asn Tyr Asn Gln Asp Pro Glu Tyr Leu Asn
            100                 105                 110

Val Trp Glu Leu Gln Gly Ile Thr Ile Asn Ser Lys Asn Asn Pro Lys
        115                 120                 125

Thr Leu Asn Gly Gln Asp Leu Glu Lys Met Gly Leu Asn Leu Lys Asp
130                 135                 140

Tyr Asn Val Thr Gln Glu Cys Ile Ile Glu Asp Ile Thr Ser Arg Lys
145                 150                 155                 160

Asp Val Asn Lys Tyr Leu Arg Lys Thr Ser Ala Pro Ile Thr Glu Leu
                165                 170                 175

Thr Gly Ser Asp Arg Tyr Glu Thr Ala Val Lys Ile Ser Lys Glu Gly
            180                 185                 190

Trp Lys Asn Gly Ser Asp Lys Val Val Ile Ile Asn Gly Asp Val Ser
        195                 200                 205

Ile Asp Gly Ile Ile Ser Thr Pro Leu Ala Thr Thr Tyr Asn Ala Pro
210                 215                 220

Ile Leu Leu Val Glu Lys Asn Asn Val Pro Asn Ser Val Lys Ser Glu
225                 230                 235                 240

Leu Lys Arg Leu Asn Pro Lys Asp Ile Ile Ile Gly Asp Glu Asn
                245                 250                 255

Ala Ile Ser Lys Thr Thr Ala Asn Gln Ile Lys Ser Thr Val Asn Ala
            260                 265                 270

Ser Gln Thr Arg Leu Asn Gly Ser Asn Arg Tyr Glu Thr Ser Leu Leu
        275                 280                 285

Ile Ala Lys Glu Ile Asp Lys Asn His Asp Val Glu Lys Val Tyr Ile
290                 295                 300

Thr Asn Ala Asn Gly Gly Glu Val Asp Ala Leu Thr Ile Ala Ala Lys
305                 310                 315                 320

Ala Gly Gln Asp Lys Gln Pro Ile Ile Leu Thr Asp Lys Asp Ser Ile
                325                 330                 335

Thr Asp Asn Thr Tyr Lys Trp Leu Lys Ser Glu Asp Leu Gln Asn Ala
            340                 345                 350

Tyr Phe Ile Gly Gly Pro Gln Met Ile Ser Thr Asn Val Ile Asn Lys
        355                 360                 365

Val Asn Gly Ile Thr Lys Asp Ser Val Thr Asn Asn Arg Val Tyr Gly
370                 375                 380

Ala Asp Arg His Glu Thr Asn Ala Asn Val Ile Lys Lys Phe Tyr Thr
385                 390                 395                 400

Glu Asp Glu Ile Glu Ala Val Leu Val Ala Lys Ser Asp Val Leu Val
                405                 410                 415

Asp Ala Leu Ala Ala Gly Pro Leu Ala Ala Asn Leu Lys Ser Pro Ile
            420                 425                 430

Leu Ile Thr Pro Lys Thr Tyr Val Ser Ala Tyr His Lys Asp Asn Leu
        435                 440                 445

Glu Ala Lys Ser Ala Asn Lys Val Tyr Lys Ile Gly Gly Gly Leu Thr
450                 455                 460

Ser Lys Val Met Ser Ser Ile Ala Ser Ser Leu Ser Lys His Asn Thr
465                 470                 475                 480

Thr Pro Thr Glu Pro Gly Asn Ser Gly Gly Lys Thr Val Met Ile Asp

```
                485                 490                 495

Pro Gly His Gly Gly Ser Ala Pro Gly Asn Ser Ser Gly Gly Met Ile
            500                 505                 510

Glu Lys Asp Tyr Asn Leu Asn Thr Ser Leu Ala Thr Thr Glu Tyr Leu
        515                 520                 525

Arg Ser Lys Gly Phe Asn Val Ile Met Thr Arg Asp Thr Asp Lys Thr
    530                 535                 540

Leu Ser Leu Gly Asn Arg Thr Ala
545                 550

<210> SEQ ID NO 20
<211> LENGTH: 675
<212> TYPE: PRT
<213> ORGANISM: Clostridium difficile

<400> SEQUENCE: 20

Met Met Lys Lys Thr Thr Lys Leu Leu Ala Thr Gly Met Leu Ser Val
1               5                   10                  15

Ala Met Val Ala Pro Asn Val Ala Leu Ala Ala Glu Asn Thr Thr Ala
            20                  25                  30

Asn Thr Glu Ser Asn Ser Asp Ile Asn Ile Asn Leu Gln Arg Lys Ser
        35                  40                  45

Val Val Leu Gly Ser Lys Ser Asn Ala Ser Val Lys Phe Lys Glu Lys
    50                  55                  60

Leu Asn Ala Asp Ser Ile Thr Leu Asn Phe Met Cys Tyr Asp Met Pro
65                  70                  75                  80

Leu Glu Ala Thr Leu Asn Tyr Asn Glu Lys Thr Asp Ser Tyr Glu Gly
                85                  90                  95

Val Ile Asn Tyr Asn Lys Asp Pro Glu Tyr Leu Asn Val Trp Glu Leu
            100                 105                 110

Gln Ser Ile Lys Ile Asn Gly Lys Asp Glu Gln Lys Val Leu Asn Lys
        115                 120                 125

Glu Asp Leu Glu Ser Met Gly Leu Asn Leu Lys Asp Tyr Asp Val Thr
    130                 135                 140

Gln Glu Phe Ile Ile Ser Asp Ala Asn Ser Thr Lys Ala Val Asn Glu
145                 150                 155                 160

Tyr Met Arg Lys Thr Ser Ala Pro Val Lys Lys Leu Ala Gly Ala Thr
                165                 170                 175

Arg Phe Glu Thr Ala Val Glu Ile Ser Lys Gln Gly Trp Lys Asp Gly
            180                 185                 190

Ser Ser Lys Val Val Ile Val Asn Gly Glu Leu Ala Ala Asp Gly Ile
        195                 200                 205

Thr Ala Thr Pro Leu Ala Ser Thr Tyr Asp Ala Pro Ile Leu Leu Ala
    210                 215                 220

Asn Lys Asp Asp Ile Pro Glu Ser Thr Lys Ala Glu Leu Lys Arg Leu
225                 230                 235                 240

Asn Pro Ser Asp Val Ile Ile Ile Gly Asp Asp Gly Ser Val Ser Gln
                245                 250                 255

Lys Ala Val Ser Gln Ile Lys Ser Ala Val Asn Val Asn Val Thr Arg
            260                 265                 270

Ile Gly Gly Val Asp Arg His Glu Thr Ser Leu Leu Ile Ala Lys Glu
        275                 280                 285

Ile Asp Lys Tyr His Asp Val Asn Lys Ile Tyr Ile Ala Asn Gly Tyr
    290                 295                 300

Ala Gly Glu Tyr Asp Ala Leu Asn Ile Ser Ser Lys Ala Gly Glu Asp
```

```
                305                 310                 315                 320
Gln Gln Pro Ile Ile Leu Ala Asn Lys Asp Ser Val Pro Gln Gly Thr
            325                 330                 335

Tyr Asn Trp Leu Ser Ser Gln Gly Leu Glu Glu Ala Tyr Tyr Ile Gly
        340                 345                 350

Gly Ser Gln Ser Leu Ser Ser Lys Ile Ile Asp Gln Ile Ser Lys Ile
    355                 360                 365

Ala Lys Asn Gly Thr Ser Lys Asn Arg Val Ser Gly Ala Asp Arg His
370                 375                 380

Glu Thr Asn Ala Asn Val Ile Lys Thr Phe Tyr Pro Asp Lys Glu Leu
385                 390                 395                 400

Ser Ala Met Leu Val Ala Lys Ser Asp Ile Ile Val Asp Ser Ile Thr
                405                 410                 415

Ala Gly Pro Leu Ala Ala Lys Leu Lys Ala Pro Ile Leu Ile Thr Pro
            420                 425                 430

Lys Thr Tyr Val Ser Ala Tyr His Ser Thr Asn Leu Ser Glu Lys Thr
        435                 440                 445

Ala Gly Thr Val Tyr Gln Ile Gly Asp Gly Met Lys Asp Ser Val Ile
    450                 455                 460

Asn Ser Ile Ala Ser Ser Leu Ser Lys His Asn Ala Pro Thr Glu Pro
465                 470                 475                 480

Asp Asn Ser Gly Ser Ala Ala Gly Lys Thr Val Val Ile Asp Pro Gly
                485                 490                 495

His Gly Gly Ser Asp Ser Gly Ala Thr Ser Gly Leu Asn Gly Gly Ala
            500                 505                 510

Gln Glu Lys Lys Tyr Thr Leu Asn Thr Ala Leu Ala Thr Thr Glu Tyr
        515                 520                 525

Leu Arg Ser Lys Gly Ile Asn Val Val Met Thr Arg Asp Thr Asp Lys
    530                 535                 540

Thr Met Ala Leu Gly Glu Arg Thr Ala Leu Ser Asn Thr Ile Lys Pro
545                 550                 555                 560

Asp Leu Phe Thr Ser Ile His Tyr Asn Ala Ser Asn Gly Ala Gly Asn
                565                 570                 575

Gly Val Glu Ile Tyr Tyr Lys Val Lys Asp Lys Asn Gly Gly Thr Thr
            580                 585                 590

Lys Thr Ala Ala Ser Asn Ile Leu Lys Arg Ile Leu Glu Lys Phe Asn
        595                 600                 605

Met Lys Asn Arg Gly Ile Lys Thr Arg Thr Leu Asp Asn Gly Lys Asp
    610                 615                 620

Tyr Leu Tyr Val Leu Arg Asn Asn Asn Tyr Pro Ala Ile Leu Val Glu
625                 630                 635                 640

Cys Ala Phe Ile Asp Asn Lys Ser Asp Met Asp Lys Leu Asn Thr Ala
                645                 650                 655

Glu Lys Val Lys Thr Met Gly Thr Gln Ile Gly Ile Gly Ile Glu Asp
            660                 665                 670

Thr Val Lys
        675

<210> SEQ ID NO 21
<211> LENGTH: 333
<212> TYPE: PRT
<213> ORGANISM: Clostridium difficile

<400> SEQUENCE: 21

Lys Ile Lys Lys Phe Thr Leu Leu Ile Ser Ile Met Ile Ile Phe Leu
```

-continued

```
                1               5                   10                  15
Cys Ala Val Val Gly Val Tyr Ser Thr Ser Ser Asn Lys Ser Val Asp
                    20                  25                  30

Leu Tyr Ser Asp Val Tyr Ile Glu Lys Tyr Phe Asn Arg Asp Lys Val
                    35                  40                  45

Met Glu Val Asn Ile Glu Ile Asp Glu Ser Asp Leu Lys Asp Met Asn
            50                  55                  60

Glu Asn Ala Ile Lys Glu Phe Lys Val Ala Lys Val Thr Val Asp
65                  70                  75                  80

Gly Asp Thr Tyr Gly Asn Val Gly Ile Arg Thr Lys Gly Asn Ser Ser
                    85                  90                  95

Leu Thr Ser Val Ala Asn Ser Asp Ser Asp Arg Tyr Ser Tyr Lys Ile
                    100                 105                 110

Asn Phe Asp Lys Tyr Asn Thr Ser Gln Ser Met Glu Gly Leu Thr Gln
                    115                 120                 125

Leu Asn Leu Asn Asn Cys Tyr Ser Asp Pro Ser Tyr Met Arg Glu Phe
            130                 135                 140

Leu Thr Tyr Ser Ile Cys Glu Glu Met Gly Leu Ala Thr Pro Glu Phe
145                 150                 155                 160

Ala Tyr Ala Lys Val Ser Ile Asn Gly Glu Tyr His Gly Leu Tyr Leu
                    165                 170                 175

Ala Val Glu Gly Leu Lys Glu Ser Tyr Leu Glu Asn Asn Phe Gly Asn
                    180                 185                 190

Val Thr Gly Asp Leu Tyr Lys Ser Asp Glu Gly Ser Ser Leu Gln Tyr
                    195                 200                 205

Lys Gly Asp Asp Pro Glu Ser Tyr Ser Asn Leu Ile Val Glu Ser Asp
                    210                 215                 220

Lys Lys Thr Ala Asp Trp Ser Lys Ile Thr Lys Leu Leu Lys Ser Leu
225                 230                 235                 240

Asp Thr Gly Glu Asp Ile Glu Lys Tyr Leu Asp Val Asp Ser Val Leu
                    245                 250                 255

Lys Asn Ile Ala Ile Asn Thr Ala Leu Leu Asn Leu Asp Ser Tyr Gln
                    260                 265                 270

Gly Ser Phe Ala His Asn Tyr Tyr Leu Tyr Glu Gln Asp Gly Val Phe
                    275                 280                 285

Ser Met Leu Pro Trp Asp Phe Asn Met Ser Phe Gly Gly Phe Ser Gly
                    290                 295                 300

Phe Gly Gly Ser Gln Ser Ile Ala Ile Asp Glu Pro Thr Thr Gly
305                 310                 315                 320

Asn Leu Glu Asp Arg Pro Leu Ile Ser Ser Leu Leu Lys
                    325                 330
```

<210> SEQ ID NO 22
<211> LENGTH: 302
<212> TYPE: PRT
<213> ORGANISM: Clostridium difficile

<400> SEQUENCE: 22

```
Lys Asn Glu Thr His Lys Thr Lys Tyr His Lys Tyr Leu Glu Glu Ile
1               5                   10                  15

Val Thr Lys Tyr Leu Asp Ser Asp Tyr Leu Glu Asn Met Thr Thr Lys
                    20                  25                  30

Leu His Asp Met Ile Ala Ser Tyr Val Lys Glu Asp Pro Thr Ala Phe
                    35                  40                  45

Tyr Thr Tyr Glu Glu Phe Glu Lys Asn Ile Thr Ser Ser Ile Glu Asp
```

-continued

```
    50                  55                  60

Ser Ser Asp Asn Lys Gly Phe Gly Asn Lys Gly Phe Asp Asn Asn Asn
65                  70                  75                  80

Ser Asn Asn Ser Asp Ser Asn Asn Asn Ser Asn Ser Glu Asn Lys Arg
                85                  90                  95

Ser Gly Asn Gln Ser Asp Lys Lys Glu Val Asn Ala Glu Leu Thr Ser
            100                 105                 110

Ser Val Val Lys Thr Asn Thr Asp Asn Glu Thr Glu Asn Lys Thr Thr
        115                 120                 125

Asn Asp Ser Glu Ser Lys Asn Asn Thr Asp Lys Asp Lys Ser Gly Asn
    130                 135                 140

Asp Asn Asn Gln Lys Leu Glu Gly Pro Arg Gly Lys Gly Gly Lys Ser
145                 150                 155                 160

Ile Pro Gly Val Leu Glu Val Ala Glu Asp Met Ser Lys Thr Ile Lys
                165                 170                 175

Ser Gln Leu Ser Gly Glu Thr Ser Ser Thr Lys Gln Asn Ser Gly Asp
            180                 185                 190

Glu Ser Ser Ser Gly Ile Lys Gly Ser Glu Lys Phe Asp Glu Asp Met
        195                 200                 205

Ser Gly Met Pro Glu Pro Pro Glu Gly Met Asp Gly Lys Met Pro Pro
    210                 215                 220

Gly Met Gly Asn Met Asp Lys Gly Asp Met Asn Gly Lys Asn Gly Asn
225                 230                 235                 240

Met Asn Met Asp Arg Asn Gln Asp Asn Pro Arg Glu Ala Gly Gly Phe
                245                 250                 255

Gly Asn Arg Gly Gly Gly Ser Val Ser Lys Thr Thr Thr Tyr Phe Lys
            260                 265                 270

Leu Ile Leu Gly Gly Ala Ser Met Ile Ile Met Ser Ile Met Leu Val
        275                 280                 285

Gly Val Ser Arg Val Lys Arg Arg Arg Phe Ile Lys Ser Lys
    290                 295                 300

<210> SEQ ID NO 23
<211> LENGTH: 635
<212> TYPE: PRT
<213> ORGANISM: Clostridium difficile

<400> SEQUENCE: 23

Met Lys Asp Lys Lys Phe Thr Leu Leu Ile Ser Ile Met Ile Ile Phe
1               5                   10                  15

Leu Cys Ala Val Val Gly Val Tyr Ser Thr Ser Ser Asn Lys Ser Val
            20                  25                  30

Asp Leu Tyr Ser Asp Val Tyr Ile Glu Lys Tyr Phe Asn Arg Asp Lys
        35                  40                  45

Val Met Glu Val Asn Ile Glu Ile Asp Glu Ser Asp Leu Lys Asp Met
    50                  55                  60

Asn Glu Asn Ala Ile Lys Glu Glu Phe Lys Val Ala Lys Val Thr Val
65                  70                  75                  80

Asp Gly Asp Thr Tyr Gly Asn Val Gly Ile Arg Thr Lys Gly Asn Ser
                85                  90                  95

Ser Leu Thr Ser Val Ala Asn Ser Asp Ser Asp Arg Tyr Ser Tyr Lys
            100                 105                 110

Ile Asn Phe Asp Lys Tyr Asn Thr Ser Gln Ser Met Glu Gly Leu Thr
        115                 120                 125

Gln Leu Asn Leu Asn Asn Cys Tyr Ser Asp Pro Ser Tyr Met Arg Glu
```

-continued

```
            130                 135                 140
Phe Leu Thr Tyr Ser Ile Cys Glu Glu Met Gly Leu Ala Thr Pro Glu
145                 150                 155                 160

Phe Ala Tyr Ala Lys Val Ser Ile Asn Gly Glu Tyr His Gly Leu Tyr
                165                 170                 175

Leu Ala Val Glu Gly Leu Lys Glu Ser Tyr Leu Glu Asn Asn Phe Gly
                180                 185                 190

Asn Val Thr Gly Asp Leu Tyr Lys Ser Asp Gly Ser Ser Leu Gln
                195                 200                 205

Tyr Lys Gly Asp Asp Pro Glu Ser Tyr Ser Asn Leu Ile Val Glu Ser
                210                 215                 220

Asp Lys Lys Thr Ala Asp Trp Ser Lys Ile Thr Lys Leu Leu Lys Ser
225                 230                 235                 240

Leu Asp Thr Gly Glu Asp Ile Glu Lys Tyr Leu Asp Val Asp Ser Val
                245                 250                 255

Leu Lys Asn Ile Ala Ile Asn Thr Ala Leu Leu Asn Leu Asp Ser Tyr
                260                 265                 270

Gln Gly Ser Phe Ala His Asn Tyr Tyr Leu Tyr Glu Gln Asp Gly Val
                275                 280                 285

Phe Ser Met Leu Pro Trp Asp Phe Asn Met Ser Phe Gly Gly Phe Ser
290                 295                 300

Gly Phe Gly Gly Gly Ser Gln Ser Ile Ala Ile Asp Glu Pro Thr Thr
305                 310                 315                 320

Gly Asn Leu Glu Asp Arg Pro Leu Ile Ser Ser Leu Leu Lys Asn Glu
                325                 330                 335

Thr His Lys Thr Lys Tyr His Lys Tyr Leu Glu Glu Ile Val Thr Lys
                340                 345                 350

Tyr Leu Asp Ser Asp Tyr Leu Glu Asn Met Thr Thr Lys Leu His Asp
                355                 360                 365

Met Ile Ala Ser Tyr Val Lys Glu Asp Pro Thr Ala Phe Tyr Thr Tyr
370                 375                 380

Glu Glu Phe Glu Lys Asn Ile Thr Ser Ser Ile Glu Asp Ser Ser Asp
385                 390                 395                 400

Asn Lys Gly Phe Gly Asn Lys Gly Phe Asp Asn Asn Asn Ser Asn Asn
                405                 410                 415

Ser Asp Ser Asn Asn Ser Asn Ser Glu Asn Lys Arg Ser Gly Asn
                420                 425                 430

Gln Ser Asp Lys Lys Glu Val Asn Ala Glu Leu Thr Ser Ser Val Val
                435                 440                 445

Lys Thr Asn Thr Asp Asn Glu Thr Glu Asn Lys Thr Thr Asn Asp Ser
450                 455                 460

Glu Ser Lys Asn Asn Thr Asp Lys Asp Lys Ser Gly Asn Asp Asn Asn
465                 470                 475                 480

Gln Lys Leu Glu Gly Pro Arg Gly Lys Gly Lys Ser Ile Pro Gly
                485                 490                 495

Val Leu Glu Val Ala Glu Asp Met Ser Lys Thr Ile Lys Ser Gln Leu
                500                 505                 510

Ser Gly Glu Thr Ser Ser Thr Lys Gln Asn Ser Gly Asp Glu Ser Ser
                515                 520                 525

Ser Gly Ile Lys Gly Ser Glu Lys Phe Asp Glu Asp Met Ser Gly Met
                530                 535                 540

Pro Glu Pro Pro Glu Gly Met Asp Gly Lys Met Pro Pro Gly Met Gly
545                 550                 555                 560
```

-continued

```
            Asn Met Asp Lys Gly Asp Met Asn Gly Lys Asn Gly Asn Met Asn Met
                            565                 570                 575

Asp Arg Asn Gln Asp Asn Pro Arg Glu Ala Gly Gly Phe Gly Asn Arg
                        580                 585                 590

Gly Gly Gly Ser Val Ser Lys Thr Thr Thr Tyr Phe Lys Leu Ile Leu
                    595                 600                 605

Gly Gly Ala Ser Met Ile Ile Met Ser Ile Met Leu Val Gly Val Ser
                610                 615                 620

Arg Val Lys Arg Arg Arg Phe Ile Lys Ser Lys
            625                 630                 635

<210> SEQ ID NO 24
<211> LENGTH: 30
<212> TYPE: DNA
<213> ORGANISM: Artificial Sequence
<220> FEATURE:
<223> OTHER INFORMATION: Chemically-synthesized CD1021 primer +
      restriction site
<220> FEATURE:
<221> NAME/KEY: misc_feature
<223> OTHER INFORMATION: Forward primer with NheI restriction site
<220> FEATURE:
<221> NAME/KEY: misc_feature
<222> LOCATION: (4)..(9)
<223> OTHER INFORMATION: NheI restriction site

<400> SEQUENCE: 24
taagctagca tgaaagataa aaaatttacc                                    30

<210> SEQ ID NO 25
<211> LENGTH: 30
<212> TYPE: DNA
<213> ORGANISM: Artificial Sequence
<220> FEATURE:
<223> OTHER INFORMATION: Chemically-synthesized CD1021 primer +
      restriction site
<220> FEATURE:
<221> NAME/KEY: misc_feature
<222> LOCATION: (4)..(10)
<223> OTHER INFORMATION: XhoI restriction site
<220> FEATURE:
<221> NAME/KEY: misc_feature
<222> LOCATION: (4)..(9)
<223> OTHER INFORMATION: XhoI restriction site

<400> SEQUENCE: 25
ttactcgagt tttgacttta taaatcttct                                    30

<210> SEQ ID NO 26
<211> LENGTH: 33
<212> TYPE: DNA
<213> ORGANISM: Artificial Sequence
<220> FEATURE:
<223> OTHER INFORMATION: Chemically-synthesized CD1021 primer +
      restriction site
<220> FEATURE:
<221> NAME/KEY: misc_feature
<222> LOCATION: (4)..(9)
<223> OTHER INFORMATION: NheI restriction site

<400> SEQUENCE: 26
acagctagca tgaaaagtgt tgatttatat agt                                33

<210> SEQ ID NO 27
<211> LENGTH: 31
<212> TYPE: DNA
<213> ORGANISM: Artificial Sequence
<220> FEATURE:
<223> OTHER INFORMATION: Chemically-synthesized CD1021 primer +
```

```
                                   restriction site
<220> FEATURE:
<221> NAME/KEY: misc_feature
<222> LOCATION: (4)..(9)
<223> OTHER INFORMATION: XhoI restriction site

<400> SEQUENCE: 27
actctcgaga gtattatact tatcaaaatt a                                      31

<210> SEQ ID NO 28
<211> LENGTH: 36
<212> TYPE: DNA
<213> ORGANISM: Artificial Sequence
<220> FEATURE:
<223> OTHER INFORMATION: Chemically-synthesized CD1021 primer +
      restriction site
<220> FEATURE:
<221> NAME/KEY: misc_feature
<222> LOCATION: (4)..(9)
<223> OTHER INFORMATION: NheI restriction site

<400> SEQUENCE: 28
aatgctagca tggtaactgg agacttatat aagtca                                 36

<210> SEQ ID NO 29
<211> LENGTH: 32
<212> TYPE: DNA
<213> ORGANISM: Artificial Sequence
<220> FEATURE:
<223> OTHER INFORMATION: Chemically-synthesized CD1021 primer +
      restriction site
<220> FEATURE:
<221> NAME/KEY: misc_feature
<222> LOCATION: (4)..(9)
<223> OTHER INFORMATION: XhoI restriction site

<400> SEQUENCE: 29
aaactcgagt ggtaacatag aaaatactcc at                                     32

<210> SEQ ID NO 30
<211> LENGTH: 33
<212> TYPE: DNA
<213> ORGANISM: Artificial Sequence
<220> FEATURE:
<223> OTHER INFORMATION: Chemically-synthesized CD1021 primer +
      restriction site
<220> FEATURE:
<221> NAME/KEY: misc_feature
<222> LOCATION: (4)..(9)
<223> OTHER INFORMATION: NheI restriction site

<400> SEQUENCE: 30
gcagctagca tgagtaaaac tataaaatct caa                                    33

<210> SEQ ID NO 31
<211> LENGTH: 33
<212> TYPE: DNA
<213> ORGANISM: Artificial Sequence
<220> FEATURE:
<223> OTHER INFORMATION: Chemically-synthesized CD1021 primer +
      restriction site
<220> FEATURE:
<221> NAME/KEY: misc_feature
<222> LOCATION: (4)..(9)
<223> OTHER INFORMATION: XhoI restriction site

<400> SEQUENCE: 31
aatctcgagg aagtatgttg ttgttttact cac                                    33

<210> SEQ ID NO 32
```

```
<211> LENGTH: 17
<212> TYPE: DNA
<213> ORGANISM: Artificial Sequence
<220> FEATURE:
<223> OTHER INFORMATION: Commercial M13 forward sequencing primer
<220> FEATURE:
<221> NAME/KEY: misc_feature
<222> LOCATION: (1)..(17)
<223> OTHER INFORMATION: M13 forward (-20) sequencing primer

<400> SEQUENCE: 32
gtaaaacgac ggccagt                                                  17

<210> SEQ ID NO 33
<211> LENGTH: 17
<212> TYPE: DNA
<213> ORGANISM: Artificial Sequence
<220> FEATURE:
<223> OTHER INFORMATION: Commercial M13 reverse sequencing primer
<220> FEATURE:
<221> NAME/KEY: misc_feature
<222> LOCATION: (1)..(17)
<223> OTHER INFORMATION: M13 reverse (-27) sequencing primer

<400> SEQUENCE: 33
caggaaacag ctatgac                                                  17

<210> SEQ ID NO 34
<211> LENGTH: 29
<212> TYPE: DNA
<213> ORGANISM: Artificial Sequence
<220> FEATURE:
<223> OTHER INFORMATION: Chemically-synthesized CD1036 +
      restriction site
<220> FEATURE:
<221> NAME/KEY: misc_feature
<222> LOCATION: (4)..(9)
<223> OTHER INFORMATION: NcoI restriction site

<400> SEQUENCE: 34
aatccatggt aagtaaggag attaatatg                                     29

<210> SEQ ID NO 35
<211> LENGTH: 30
<212> TYPE: DNA
<213> ORGANISM: Artificial Sequence
<220> FEATURE:
<223> OTHER INFORMATION: Chemically-synthesized CD1036 primer +
      restriction site
<220> FEATURE:
<221> NAME/KEY: misc_feature
<222> LOCATION: (4)..(9)
<223> OTHER INFORMATION: XhoI restriction site

<400> SEQUENCE: 35
ttcctcgagt tttaatgaat cttctattcc                                    30

<210> SEQ ID NO 36
<211> LENGTH: 29
<212> TYPE: DNA
<213> ORGANISM: Artificial Sequence
<220> FEATURE:
<223> OTHER INFORMATION: Chemically-synthesized CD1036 primer +
      restriction site
<220> FEATURE:
<221> NAME/KEY: misc_feature
<222> LOCATION: (4)..(9)
<223> OTHER INFORMATION: NcoI restriction site

<400> SEQUENCE: 36
aggccatgga taaaaatcat gatgtggaa                                     29
```

```
<210> SEQ ID NO 37
<211> LENGTH: 30
<212> TYPE: DNA
<213> ORGANISM: Artificial Sequence
<220> FEATURE:
<223> OTHER INFORMATION: Chemically-synthesized CD1036 primer +
      restriction site
<220> FEATURE:
<221> NAME/KEY: misc_feature
<222> LOCATION: (4)..(9)
<223> OTHER INFORMATION: XhoI restriction site

<400> SEQUENCE: 37
tttctcgagg tttgcatttg tttcgtgtct                                         30

<210> SEQ ID NO 38
<211> LENGTH: 635
<212> TYPE: PRT
<213> ORGANISM: Artificial Sequence
<220> FEATURE:
<223> OTHER INFORMATION: Computer program-generated consensus protein
      sequence for CD1021
<220> FEATURE:
<221> NAME/KEY: VARIANT
<222> LOCATION: (1)..(12)
<223> OTHER INFORMATION: An "Xaa" designates a residue where variants
      were observed among the sequences (SEQ ID NOS: 1, 11, 12, 21, 22,
      23) aligned in Figure 1.  Variations may include amino acid
      substitutions at these respective residue positions.
<220> FEATURE:
<221> NAME/KEY: VARIANT
<222> LOCATION: (15)..(15)
<223> OTHER INFORMATION: An "Xaa" designates a residue where variants
      were observed among the sequences (SEQ ID NOS: 1, 11, 12, 21, 22,
      23) aligned in Figure 1.  Variations may include amino acid
      substitutions at residue 15.
<220> FEATURE:
<221> NAME/KEY: VARIANT
<222> LOCATION: (99)..(99)
<223> OTHER INFORMATION: An "Xaa" designates a residue where variants
      were observed among the sequences (SEQ ID NOS: 1, 11, 12, 21, 22,
      23) aligned in Figure 1.  Variations may include amino acid
      substitutions at residue 99.
<220> FEATURE:
<221> NAME/KEY: VARIANT
<222> LOCATION: (334)..(361)
<223> OTHER INFORMATION: An "Xaa" designates a residue where variants
      were observed among the sequences (SEQ ID NOS: 1, 11, 12, 21, 22,
      23) aligned in Figure 1.  Variations may include amino acid
      substitutions at these respective residue positions.

<400> SEQUENCE: 38

Xaa Xaa Xaa Xaa Xaa Xaa Xaa Xaa Xaa Xaa Xaa Xaa Met Ile Xaa Phe
1               5                   10                  15

Leu Cys Ala Val Val Gly Val Tyr Ser Thr Ser Ser Asn Lys Ser Val
            20                  25                  30

Asp Leu Tyr Ser Asp Val Tyr Ile Glu Lys Tyr Phe Asn Arg Asp Lys
        35                  40                  45

Val Met Glu Val Asn Ile Glu Ile Asp Glu Ser Asp Leu Lys Asp Met
    50                  55                  60

Asn Glu Asn Ala Ile Lys Glu Glu Phe Lys Val Ala Lys Val Thr Val
65                  70                  75                  80

Asp Gly Asp Thr Tyr Gly Asn Val Gly Ile Arg Thr Lys Gly Asn Ser
                85                  90                  95

Ser Leu Xaa Ser Val Ala Asn Ser Asp Ser Arg Tyr Ser Tyr Lys
            100                 105                 110

Ile Asn Phe Asp Lys Tyr Asn Thr Ser Gln Ser Met Glu Gly Leu Thr
            115                 120                 125
```

```
Gln Leu Asn Leu Asn Asn Cys Tyr Ser Asp Pro Ser Tyr Met Arg Glu
    130                 135                 140

Phe Leu Thr Tyr Ser Ile Cys Glu Glu Met Gly Leu Ala Thr Pro Glu
145                 150                 155                 160

Phe Ala Tyr Ala Lys Val Ser Ile Asn Gly Glu Tyr His Gly Leu Tyr
                165                 170                 175

Leu Ala Val Glu Gly Leu Lys Glu Ser Tyr Leu Glu Asn Asn Phe Gly
            180                 185                 190

Asn Val Thr Gly Asp Leu Tyr Lys Ser Asp Glu Gly Ser Ser Leu Gln
        195                 200                 205

Tyr Lys Gly Asp Asp Pro Glu Ser Tyr Ser Asn Leu Ile Val Glu Ser
    210                 215                 220

Asp Lys Lys Thr Ala Asp Trp Ser Lys Ile Thr Lys Leu Leu Lys Ser
225                 230                 235                 240

Leu Asp Thr Gly Glu Asp Ile Glu Lys Tyr Leu Asp Val Asp Ser Val
                245                 250                 255

Leu Lys Asn Ile Ala Ile Asn Thr Ala Leu Leu Asn Leu Asp Ser Tyr
            260                 265                 270

Gln Gly Ser Phe Ala His Asn Tyr Tyr Leu Tyr Glu Gln Asp Gly Val
        275                 280                 285

Phe Ser Met Leu Pro Trp Asp Phe Asn Met Ser Phe Gly Gly Phe Ser
    290                 295                 300

Gly Phe Gly Gly Gly Ser Gln Ser Ile Ala Ile Asp Glu Pro Thr Thr
305                 310                 315                 320

Gly Asn Leu Glu Asp Arg Pro Leu Ile Ser Ser Leu Leu Lys Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Met Thr Thr Lys Leu His Asp
        355                 360                 365

Met Ile Ala Ser Tyr Val Lys Glu Asp Pro Thr Ala Phe Tyr Thr Tyr
    370                 375                 380

Glu Glu Phe Glu Lys Asn Ile Thr Ser Ser Ile Glu Asp Ser Ser Asp
385                 390                 395                 400

Asn Lys Gly Phe Gly Asn Lys Gly Phe Asp Asn Asn Asn Ser Asn Asn
                405                 410                 415

Ser Asp Ser Asn Asn Asn Ser Asn Ser Glu Asn Lys Arg Ser Gly Asn
            420                 425                 430

Gln Ser Asp Lys Lys Glu Val Asn Ala Glu Leu Thr Ser Ser Val Val
        435                 440                 445

Lys Thr Asn Thr Asp Asn Glu Thr Glu Asn Lys Thr Thr Asn Asp Ser
    450                 455                 460

Glu Ser Lys Asn Asn Thr Asp Lys Asp Lys Ser Gly Asn Asp Asn Asn
465                 470                 475                 480

Gln Lys Leu Glu Gly Pro Arg Gly Lys Gly Lys Ser Ile Pro Gly
                485                 490                 495

Val Leu Glu Val Ala Glu Asp Met Ser Lys Thr Ile Lys Ser Gln Leu
            500                 505                 510

Ser Gly Glu Thr Ser Ser Thr Lys Gln Asn Ser Gly Asp Glu Ser Ser
        515                 520                 525

Ser Gly Ile Lys Gly Ser Glu Lys Phe Asp Glu Asp Met Ser Gly Met
    530                 535                 540

Pro Glu Pro Pro Glu Gly Met Asp Gly Lys Met Pro Pro Gly Met Gly
```

```
                 545                 550                 555                 560
Asn Met Asp Lys Gly Asp Met Asn Gly Lys Asn Gly Asn Met Asn Met
                565                 570                 575

Asp Arg Asn Gln Asp Asn Pro Arg Glu Ala Gly Gly Phe Gly Asn Arg
                580                 585                 590

Gly Gly Gly Ser Val Ser Lys Thr Thr Thr Tyr Phe Lys Leu Ile Leu
                595                 600                 605

Gly Gly Ala Ser Met Ile Ile Met Ser Ile Met Leu Val Gly Val Ser
            610                 615                 620

Arg Val Lys Arg Arg Arg Phe Ile Lys Ser Lys
625                 630                 635

<210> SEQ ID NO 39
<211> LENGTH: 1905
<212> TYPE: DNA
<213> ORGANISM: Clostridium difficile

<400> SEQUENCE: 39
atgaaagata aaaaatttac ccttcttatc tcgattatga ttatattttt atgtgctgta      60
gttggagttt atagtacatc tagcaacaaa agtgttgatt tatatagtga tgtatatatt     120
gaaaaatatt ttaacagaga caaggttatg gaagttaata tagagataga tgaaagtgac    180
ttgaaggata tgaatgaaaa tgctataaaa gaagaattta ggttgcaaaa gtaactgta     240
gatggagata catatggaaa cgtaggtata agaactaaag gaaattcaag tcttatatct     300
gtagcaaata gtgatagtga tagatacagc tataagatta ttttgataa gtataatact     360
agtcaaagta tggaagggct tactcaatta aatcttaata actgttactc tgacccatct     420
tatatgagag agttttttaac atatagtatt tgcgaggaaa tgggattagc gactccagaa    480
tttgcatatg ctaaagtctc tataaatggc gaatatcatg gtttgtattt ggcagtagaa    540
ggattaaaag agtcttatct tgaaaataat tttggtaatg taactggaga cttatataag    600
tcagatgaag gaagctcgtt gcaatataaa ggagatgacc cagaaagtta ctcaaactta    660
atcgttgaaa gtgataaaaa gacagctgat tggtctaaaa tcacaaaact attaaaatct    720
ttggatacag gtgaagatat tgaaaaatat cttgatgtag attctgtcct taaaaatata    780
gcaataaata cagctttatt aaaccttgat agctatcaag ggagttttgc ccataactat    840
tatttatatg agcaagatgg agtatttct atgttaccat gggattttaa tatgtcattt     900
ggtggattta gtggttttgg tggaggtagt caatctatag caattgatga acctacgaca    960
ggtaatttag aagacagacc tctcatatcc tcgttattaa aaaatgagac atacaaaaca   1020
aaataccata aatatctgga agagatagta acaaaatacc tagattcaga ctatttagag   1080
aatatgacaa caaaattgca tgacatgata gcatcatatg taaagaaga cccaacagca    1140
ttttatactt atgaagaatt tgaaaaaaat ataacatctt caattgaaga ttctagtgat   1200
aataagggat ttggtaataa agggtttgac aacaataact ctaataacag tgattctaat    1260
aataattcta atagtgaaaa taagcgctct ggaaatcaaa gtgatgaaaa agaagttaat   1320
gctgaattaa catcaagcgt agtcaaagct aatacagata tgaaactaa aaataaaact   1380
acaaatgata gtgaaagtaa gaataataca gataaagata aagtggaaa tgataataat    1440
caaaagctag aaggtcctat gggtaaagga ggtaagtcaa taccagggg tttggaagtt   1500
gcagaagata tgagtaaaac tataaaatct caattaagtg gagaaacttc ttcgacaaag  1560
caaaactctg gtgatgaaag ttcaagtgga attaaaggta gtgaaaagtt tgatgaggat   1620
atgagtggta tgccagaacc acctgaggga atggatggta aaatgccacc aggaatgggt   1680
```

```
aatatggata agggagatat gaatggtaaa aatggcaata tgaatatgga tagaaatcaa   1740
gataatccaa gagaagctgg aggttttggc aatagaggag gaggctctgt gagtaaaaca   1800
acaacatact tcaaattaat tttaggtgga gcttcaatga taataatgtc gattatgtta   1860
gttggtgtat caagggtaaa gagaagaaga tttataaagt caaaa                   1905

<210> SEQ ID NO 40
<211> LENGTH: 276
<212> TYPE: DNA
<213> ORGANISM: Clostridium difficile

<400> SEQUENCE: 40
atgaaaagtg ttgatttata tagtgatgta tatattgaaa atatttttaa cagagacaag     60
gttatggaag ttaatataga gatagatgaa agtgacttga aggatatgaa tgaaaatgct   120
ataaaagaag aatttaaggt tgcaaaagta actgtagatg gagatacata tggaaacgta   180
ggtataagaa ctaaaggaaa ttcaagtctt atatctgtag caaatagtga tagtgataga   240
tacagctata agattaattt tgataagtat aatact                              276

<210> SEQ ID NO 41
<211> LENGTH: 303
<212> TYPE: DNA
<213> ORGANISM: Clostridium difficile

<400> SEQUENCE: 41
atggtaactg agacttata taagtcagat gaaggaagct cgttgcaata taaggagat      60 gacccagaaa gttactcaaa cttaatcgtt gaaagtgata aaaagacagc tgattggtct   120
aaaatcacaa aactattaaa atctttggat acaggtgaag atattgaaaa atatcttgat   180
gtagattctg tccttaaaaa tatagcaata aatacagctt tattaaaccct tgatagctat   240 caagggagtt ttgcccataa ctattattta tatgagcaag atggagtatt ttctatgtta   300
cca                                                                  303

<210> SEQ ID NO 42
<211> LENGTH: 303
<212> TYPE: DNA
<213> ORGANISM: Clostridium difficile

<400> SEQUENCE: 42
atgagtaaaa ctataaaatc tcaattaagt ggagaaactt cttcgacaaa gcaaaactct    60
ggtgatgaaa gttcaagtgg aattaaaggt agtgaaaagt ttgatgagga tatgagtggt   120
atgccagaac cacctgaggg aatggatggt aaaatgccac caggaatggg taatatggat   180
aagggagata tgaatggtaa aaatggcaat atgaatatgg atagaaatca agataatcca   240
agagaagctg gaggttttgg caatagagga ggaggctctg tgagtaaaac aacaacatac   300
ttc                                                                  303

<210> SEQ ID NO 43
<211> LENGTH: 2031
<212> TYPE: DNA
<213> ORGANISM: Clostridium difficile

<400> SEQUENCE: 43
atggtaagta aggagattaa tatgagaaga aatacaaaat tattaacaac agggattctt    60
tcaatggcaa tcgtcgcacc tacaatggca tttgctactg aatctaatgc tatggaaaat   120
aacgctgatt taaatataaa cttagagaaa aaaagtatcg ttttaggtag caaatcaaaa   180
```

```
gttagtgtca aatttaaaga aaaaccagat gcagatagca ttacattaaa gtataaatgc      240
tatgacatgc cattgaatac aactctaaat tacaatcaat caactggggc atatgaagga      300
actatcaatt ataaccaaga cccagaatat ctaaatgttt gggaactaca agggataaca      360
ataaacagca aaaataatca taaaacttta aacagacaag acctagaaaa gctgggatta      420
aatttaaaag actataatgt aacacaggaa tgtataattg aagatataac ttctagaaaa      480
gatgtaaata atatttgag aaaaacttct tcacctatta cagaacttac aggaagtgat       540
agatatgaaa cagcagttaa aataagtaaa gagggctgga aaaatggttc agataaggta      600
gttataataa atggggatgt aagtatagat ggcattatat caactccact ggcaaccaca      660
tataatgcac caatactttt ggttgaaaaa acaatgtac ctaatagtgt aaaatcagaa       720
ttaaagcgcc taaaccctaa agatataatt ataattggag atgagaatgc tatttctaaa      780
actactgcta atcaaattaa atcaactgta aatgctagtc aaacacgttt aaatggttct      840
aatagatatg agacatcttt attgatagca aaggaaatag ataaaaatca tgatgtggaa      900
aaagtataca taacaaatgc taatggcgga gaagtggatg cacttactat agcagcaaaa      960
gcaggtcaag acaagcaacc aattatatta actgataaag atagtattac agacaataca     1020
tataaatggt taaagagtga ggatttacaa aatgcttatt ttataggtgg tcctcaaatg     1080
atatcaacaa atgttataaa taaggtaaat ggaataacta agatagtgt tactaataat      1140 agagtatacg gagcagatag acacgaaaca aatgcaaacg taataaaaaa attctataca     1200
gatgatgagt tagaggctgt tttagtagct aaatcagatg tacttgttga tgctttagca     1260
gcaggtccat tggctgcgaa cttaaaatct ccaatactta taacaccaaa gacgtatgta     1320
tctgcatacc ataagagtaa tttagaagct aaatcagcta ataaggtata caaaatagga     1380
ggaggattga cttctaaggt aatgagctct atagcatcat cattatctaa acacaatacg     1440
actccaacag aaccaggaaa tagtgggggc aagacagtta tgattgaccc agggcatggt     1500
ggttcagcac ctggaaattc atctggagga atgattgaaa agattacaa tttaaatact       1560 tcacttgcaa caactgaata tttacgttca aagggattca atgtaataat gacaagagac     1620
acagataaga cttatctct tggaaataga actgctctat ctaattcatt gaaaccagat       1680
ttatttacaa gtacacatta taatggctca actaataaac aaggtcatgg tgtagaagta      1740 tttttataagc ttaaagataa aaatggaggg actactaaaa ctgtagctac caatatatta     1800
aatagaattt tagagaaatt taaacttaca aatagaggta taaaaacaag agtacttcct     1860
agtgattcta caaaagatta tttatacgtt ttaagaagta atgatatgcc agctgtactt     1920
gtagaatgtg cattttggga taatgaaaat gatatgagtt taataaactc atctgcaaaa     1980
gtaaaagaaa tgggtacaca aataggtaaa ggaatagaag attcattaaa a              2031
```

<210> SEQ ID NO 44  
<211> LENGTH: 303  
<212> TYPE: DNA  
<213> ORGANISM: Clostridium difficile

<400> SEQUENCE: 44

```
atggataaaa atcatgatgt ggaaaaagta tacataacaa atgctaatgg cggagaagtg        60
gatgcactta ctatagcagc aaaagcaggt caagacaagc aaccaattat attaactgat       120
aaagatagta ttacagacaa tacatataaa tggttaaaga gtgaggattt acaaaatgct      180
tattttatag gtggtcctca aatgatatca acaaatgtta taaataaggt aaatggaata      240
actaaagata gtgttactaa taatagagta tacggagcag atagacacga aacaaatgca      300
```

```
                                    aac                                                   303

<210> SEQ ID NO 45
<211> LENGTH: 635
<212> TYPE: PRT
<213> ORGANISM: Clostridium difficile

<400> SEQUENCE: 45

Met Lys Asp Lys Lys Phe Thr Leu Leu Ile Ser Ile Met Ile Ile Phe
1               5                   10                  15

Leu Cys Ala Val Val Gly Val Tyr Ser Thr Ser Asn Lys Ser Val
            20                  25                  30

Asp Leu Tyr Ser Asp Val Tyr Ile Glu Lys Tyr Phe Asn Arg Asp Lys
        35                  40                  45

Val Met Glu Val Asn Ile Glu Ile Asp Glu Ser Asp Leu Lys Asp Met
    50                  55                  60

Asn Glu Asn Ala Ile Lys Glu Phe Lys Val Ala Lys Val Thr Val
65              70                  75                  80

Asp Gly Asp Thr Tyr Gly Asn Val Gly Ile Arg Thr Lys Gly Asn Ser
                85                  90                  95

Ser Leu Ile Ser Val Ala Asn Ser Asp Ser Asp Arg Tyr Ser Tyr Lys
            100                 105                 110

Ile Asn Phe Asp Lys Tyr Asn Thr Ser Gln Ser Met Glu Gly Leu Thr
        115                 120                 125

Gln Leu Asn Leu Asn Asn Cys Tyr Ser Asp Pro Ser Tyr Met Arg Glu
    130                 135                 140

Phe Leu Thr Tyr Ser Ile Cys Glu Glu Met Gly Leu Ala Thr Pro Glu
145                 150                 155                 160

Phe Ala Tyr Ala Lys Val Ser Ile Asn Gly Glu Tyr His Gly Leu Tyr
                165                 170                 175

Leu Ala Val Glu Gly Leu Lys Gly Ser Tyr Leu Glu Asn Asn Phe Gly
            180                 185                 190

Asn Val Thr Gly Asp Leu Tyr Lys Ser Asp Glu Gly Ser Ser Leu Gln
        195                 200                 205

Tyr Lys Gly Asp Asp Pro Glu Ser Tyr Ser Asn Leu Ile Val Glu Ser
    210                 215                 220

Asp Lys Lys Thr Ala Asp Trp Ser Lys Ile Thr Lys Leu Leu Lys Ser
225                 230                 235                 240

Leu Asp Thr Gly Glu Asp Ile Glu Lys Tyr Leu Asp Val Asp Ser Val
                245                 250                 255

Leu Lys Asn Ile Ala Ile Asn Thr Ala Leu Leu Asn Leu Asp Ser Tyr
            260                 265                 270

Gln Gly Ser Phe Ala His Asn Tyr Tyr Leu Tyr Glu Gln Asp Gly Val
        275                 280                 285

Phe Ser Met Leu Pro Trp Asp Phe Asn Met Ser Phe Gly Gly Phe Ser
    290                 295                 300

Gly Phe Gly Gly Gly Ser Gln Ser Ile Ala Ile Asp Glu Pro Thr Thr
305                 310                 315                 320

Gly Asn Leu Glu Asp Arg Pro Leu Ile Ser Ser Leu Leu Lys Asn Glu
                325                 330                 335

Thr Tyr Lys Thr Lys Tyr His Lys Tyr Leu Glu Glu Ile Val Thr Lys
            340                 345                 350

Tyr Leu Asp Ser Asp Tyr Leu Glu Asn Met Thr Thr Lys Leu His Asp
        355                 360                 365
```

```
Met Ile Ala Ser Tyr Val Lys Glu Asp Pro Thr Ala Phe Tyr Thr Tyr
    370                 375                 380

Glu Glu Phe Glu Lys Asn Ile Thr Ser Ser Ile Glu Asp Ser Ser Asp
385                 390                 395                 400

Asn Lys Gly Phe Gly Asn Lys Gly Phe Asp Asn Asn Asn Ser Asn Asn
                405                 410                 415

Ser Asp Ser Asn Asn Asn Ser Asn Ser Glu Asn Lys Arg Ser Gly Asn
            420                 425                 430

Gln Ser Asp Glu Lys Glu Val Asn Ala Glu Leu Thr Ser Ser Val Val
        435                 440                 445

Lys Ala Asn Thr Asp Asn Glu Thr Lys Asn Lys Thr Thr Asn Asp Ser
    450                 455                 460

Glu Ser Lys Asn Asn Thr Asp Lys Asp Lys Ser Gly Asn Asp Asn Asn
465                 470                 475                 480

Gln Lys Leu Glu Gly Pro Met Gly Lys Gly Gly Lys Ser Ile Pro Gly
                485                 490                 495

Val Leu Glu Val Ala Glu Asp Met Ser Lys Thr Ile Lys Ser Gln Leu
            500                 505                 510

Ser Gly Glu Thr Ser Ser Thr Lys Gln Asn Ser Gly Asp Glu Ser Ser
        515                 520                 525

Ser Gly Ile Lys Gly Ser Glu Lys Phe Asp Glu Asp Met Ser Gly Met
    530                 535                 540

Pro Glu Pro Pro Glu Gly Met Asp Gly Lys Met Pro Pro Gly Met Gly
545                 550                 555                 560

Asn Met Asp Lys Gly Asp Met Asn Gly Lys Asn Gly Asn Met Asn Met
                565                 570                 575

Asp Arg Asn Gln Asp Asn Pro Arg Glu Ala Gly Gly Phe Gly Asn Arg
            580                 585                 590

Gly Gly Gly Ser Val Ser Lys Thr Thr Thr Tyr Phe Lys Leu Ile Leu
        595                 600                 605

Gly Gly Ala Ser Met Ile Ile Met Ser Ile Met Leu Val Gly Val Ser
    610                 615                 620

Arg Val Lys Arg Arg Arg Phe Ile Lys Ser Lys
625                 630                 635

<210> SEQ ID NO 46
<211> LENGTH: 92
<212> TYPE: PRT
<213> ORGANISM: Clostridium difficile

<400> SEQUENCE: 46

Met Lys Ser Val Asp Leu Tyr Ser Asp Val Tyr Ile Glu Lys Tyr Phe
1               5                   10                  15

Asn Arg Asp Lys Val Met Glu Val Asn Ile Glu Ile Asp Glu Ser Asp
            20                  25                  30

Leu Lys Asp Met Asn Glu Asn Ala Ile Lys Glu Glu Phe Lys Val Ala
        35                  40                  45

Lys Val Thr Val Asp Gly Asp Thr Tyr Gly Asn Val Gly Ile Arg Thr
    50                  55                  60

Lys Gly Asn Ser Ser Leu Ile Ser Val Ala Asn Ser Asp Ser Asp Arg
65                  70                  75                  80

Tyr Ser Tyr Lys Ile Asn Phe Asp Lys Tyr Asn Thr
                85                  90

<210> SEQ ID NO 47
<211> LENGTH: 101
```
<212> TYPE: PRT
<213> ORGANISM: Clostridium difficile

<400> SEQUENCE: 47

Met Val Thr Gly Asp Leu Tyr Lys Ser Asp Glu Gly Ser Ser Leu Gln
1 5 10 15

Tyr Lys Gly Asp Asp Pro Glu Ser Tyr Ser Asn Leu Ile Val Glu Ser
20 25 30

Asp Lys Lys Thr Ala Asp Trp Ser Lys Ile Thr Lys Leu Leu Lys Ser
35 40 45

Leu Asp Thr Gly Glu Asp Ile Glu Lys Tyr Leu Asp Val Asp Ser Val
50 55 60

Leu Lys Asn Ile Ala Ile Asn Thr Ala Leu Leu Asn Leu Asp Ser Tyr
65 70 75 80

Gln Gly Ser Phe Ala His Asn Tyr Tyr Leu Tyr Glu Gln Asp Gly Val
85 90 95

Phe Ser Met Leu Pro
100

<210> SEQ ID NO 48
<211> LENGTH: 101
<212> TYPE: PRT
<213> ORGANISM: Clostridium difficile

<400> SEQUENCE: 48

Met Ser Lys Thr Ile Lys Ser Gln Leu Ser Gly Glu Thr Ser Ser Thr
1 5 10 15

Lys Gln Asn Ser Gly Asp Glu Ser Ser Ser Gly Ile Lys Gly Ser Glu
20 25 30

Lys Phe Asp Glu Asp Met Ser Gly Met Pro Glu Pro Pro Glu Gly Met
35 40 45

Asp Gly Lys Met Pro Pro Gly Met Gly Asn Met Asp Lys Gly Asp Met
50 55 60

Asn Gly Lys Asn Gly Asn Met Asn Met Asp Arg Asn Gln Asp Asn Pro
65 70 75 80

Arg Glu Ala Gly Gly Phe Gly Asn Arg Gly Gly Gly Ser Val Ser Lys
85 90 95

Thr Thr Thr Tyr Phe
100

<210> SEQ ID NO 49
<211> LENGTH: 677
<212> TYPE: PRT
<213> ORGANISM: Clostridium difficile

<400> SEQUENCE: 49

Met Val Ser Lys Glu Ile Asn Met Arg Arg Asn Thr Lys Leu Leu Thr
1 5 10 15

Thr Gly Ile Leu Ser Met Ala Ile Val Ala Pro Thr Met Ala Phe Ala
20 25 30

Thr Glu Ser Asn Ala Met Glu Asn Asn Ala Asp Leu Asn Ile Asn Leu
35 40 45

Glu Lys Lys Ser Ile Val Leu Gly Ser Lys Ser Lys Val Ser Val Lys
50 55 60

Phe Lys Glu Lys Pro Asp Ala Asp Ser Ile Thr Leu Lys Tyr Lys Cys
65 70 75 80

Tyr Asp Met Pro Leu Asn Thr Thr Leu Asn Tyr Asn Gln Ser Thr Gly
85 90 95

Ala Tyr Glu Gly Thr Ile Asn Tyr Asn Gln Asp Pro Glu Tyr Leu Asn
                100                 105                 110

Val Trp Glu Leu Gln Gly Ile Thr Ile Asn Ser Lys Asn Asn His Lys
            115                 120                 125

Thr Leu Asn Arg Gln Asp Leu Glu Lys Leu Gly Leu Asn Leu Lys Asp
        130                 135                 140

Tyr Asn Val Thr Gln Glu Cys Ile Ile Glu Asp Ile Thr Ser Arg Lys
145                 150                 155                 160

Asp Val Asn Lys Tyr Leu Arg Lys Thr Ser Pro Ile Thr Glu Leu
                165                 170                 175

Thr Gly Ser Asp Arg Tyr Glu Thr Ala Val Lys Ile Ser Lys Glu Gly
            180                 185                 190

Trp Lys Asn Gly Ser Asp Lys Val Val Ile Ile Asn Gly Asp Val Ser
        195                 200                 205

Ile Asp Gly Ile Ile Ser Thr Pro Leu Ala Thr Thr Tyr Asn Ala Pro
210                 215                 220

Ile Leu Leu Val Glu Lys Asn Asn Val Pro Asn Ser Val Lys Ser Glu
225                 230                 235                 240

Leu Lys Arg Leu Asn Pro Lys Asp Ile Ile Ile Gly Asp Glu Asn
                245                 250                 255

Ala Ile Ser Lys Thr Thr Ala Asn Gln Ile Lys Ser Thr Val Asn Ala
            260                 265                 270

Ser Gln Thr Arg Leu Asn Gly Ser Asn Arg Tyr Glu Thr Ser Leu Leu
        275                 280                 285

Ile Ala Lys Glu Ile Asp Lys Asn His Asp Val Glu Lys Val Tyr Ile
    290                 295                 300

Thr Asn Ala Asn Gly Gly Glu Val Asp Ala Leu Thr Ile Ala Ala Lys
305                 310                 315                 320

Ala Gly Gln Asp Lys Gln Pro Ile Ile Leu Thr Asp Lys Asp Ser Ile
                325                 330                 335

Thr Asp Asn Thr Tyr Lys Trp Leu Lys Ser Glu Asp Leu Gln Asn Ala
            340                 345                 350

Tyr Phe Ile Gly Gly Pro Gln Met Ile Ser Thr Asn Val Ile Asn Lys
        355                 360                 365

Val Asn Gly Ile Thr Lys Asp Ser Val Thr Asn Arg Val Tyr Gly
    370                 375                 380

Ala Asp Arg His Glu Thr Asn Ala Asn Val Ile Lys Lys Phe Tyr Thr
385                 390                 395                 400

Asp Asp Glu Leu Glu Ala Val Leu Val Ala Lys Ser Asp Val Leu Val
                405                 410                 415

Asp Ala Leu Ala Ala Gly Pro Leu Ala Ala Asn Leu Lys Ser Pro Ile
            420                 425                 430

Leu Ile Thr Pro Lys Thr Tyr Val Ser Ala Tyr His Lys Asp Asn Leu
        435                 440                 445

Glu Ala Lys Ser Ala Asn Lys Val Tyr Lys Ile Gly Gly Gly Leu Thr
    450                 455                 460

Ser Lys Val Met Ser Ser Ile Ala Ser Ser Leu Ser Lys His Asn Thr
465                 470                 475                 480

Thr Pro Thr Glu Pro Gly Asn Ser Gly Gly Lys Thr Val Met Ile Asp
                485                 490                 495

Pro Gly His Gly Gly Ser Ala Pro Gly Asn Ser Ser Gly Gly Met Ile
            500                 505                 510

Glu Lys Asp Tyr Asn Leu Asn Thr Ser Leu Ala Thr Thr Glu Tyr Leu

-continued

```
                515                 520                 525
Arg Ser Lys Gly Phe Asn Val Ile Met Thr Arg Asp Thr Asp Lys Thr
        530                 535                 540

Leu Ser Leu Gly Asn Arg Thr Ala Leu Ser Asn Ser Leu Lys Pro Asp
545                 550                 555                 560

Leu Phe Thr Ser Ile His Tyr Asn Gly Ser Thr Asn Lys Gln Gly His
                565                 570                 575

Gly Val Glu Val Phe Tyr Lys Leu Lys Asp Lys Asn Gly Gly Thr Thr
            580                 585                 590

Lys Thr Val Ala Thr Asn Ile Leu Asn Arg Ile Leu Glu Lys Phe Lys
            595                 600                 605

Leu Thr Asn Arg Gly Ile Lys Thr Arg Val Leu Pro Ser Asp Ser Thr
            610                 615                 620

Lys Asp Tyr Leu Tyr Val Leu Arg Ser Asn Asp Met Pro Ala Val Leu
625                 630                 635                 640

Val Glu Cys Ala Phe Leu Asp Asn Glu Asn Asp Met Ser Leu Ile Asn
                645                 650                 655

Ser Ser Ala Lys Val Lys Glu Met Gly Thr Gln Ile Gly Lys Gly Ile
                660                 665                 670

Glu Asp Ser Leu Lys
            675

<210> SEQ ID NO 50
<211> LENGTH: 101
<212> TYPE: PRT
<213> ORGANISM: Clostridium difficile

<400> SEQUENCE: 50

Met Asp Lys Asn His Asp Val Glu Lys Val Tyr Ile Thr Asn Ala Asn
1               5                   10                  15

Gly Gly Glu Val Asp Ala Leu Thr Ile Ala Ala Lys Ala Gly Gln Asp
            20                  25                  30

Lys Gln Pro Ile Ile Leu Thr Asp Lys Asp Ser Ile Thr Asp Asn Thr
        35                  40                  45

Tyr Lys Trp Leu Lys Ser Glu Asp Leu Gln Asn Ala Tyr Phe Ile Gly
    50                  55                  60

Gly Pro Gln Met Ile Ser Thr Asn Val Ile Asn Lys Val Asn Gly Ile
65                  70                  75                  80

Thr Lys Asp Ser Val Thr Asn Asn Arg Val Tyr Gly Ala Asp Arg His
                85                  90                  95

Glu Thr Asn Ala Asn
            100
```

ANTIBODIES TO *CLOSTRIDIUM DIFFICILE* SPORES AND USES THEREOF

CROSS REFERENCE TO RELATED APPLICATIONS

This application claims the benefit of U.S. Provisional Application Ser. No. 61/032,270, filed Feb. 28, 2008, which is incorporated herein by reference.

This application has associated with it a sequence listing with the file name Sequence_Listing_63842US005.TXT, created March 30, 2009. The sequence listing file contains 98,928 bytes and it is incorporated herein by reference in its entirety.

BACKGROUND

*Clostridium difficile*, an anaerobic spore forming Gram-positive bacteria, is the major cause of pseudomembraneous colitis and antibiotic associated diarrhea in humans and is one of the most widespread bacterium implicated in hospital acquired, nosocomial infections (see, for example, Wren, 2006, *Future Microbiol;* 1 (3):243-245). According to the Center for Disease Control (CDC), *C. difficile* is responsible for tens of thousands of cases of diarrhea and at least 5,000 deaths each year in the United States. The number of *C. difficile* infections doubled between 1993 and 2003, with the largest increase coming after 2000.

Individuals with a *C. difficile*-associated disease shed spores in the stool. *C. difficile* infections are frequently transmitted between hospitalized patients and the organism is often present on the hands of hospital personnel (see, for example, McFarland et al., 1989, *N Engl J Med;* 320:204-210). Patients infected with a *C. difficile* infection are isolated and precautions are taken to avoid outbreaks. Asymptomatic carriers can shed spores and need to be screened for isolation purposes (see, for example, Kyne et al., 2000, *N Engl J Med;* 342:390-397).

*C. difficile* spores are resistant to heat, drying, and cleaning agents and can survive up to seventy days on environmental surfaces, such as cart handles, bedrails, bedpans, toilets, bathing tubs, floors, furniture, linens, telephones, stethoscopes, thermometers, and remote controls. Thus, environmental surfaces are a ready source of infection. The thorough cleaning of patient's rooms during hospitalization is needed.

There is a clear need to monitor cleaning effectiveness and to verify that patient rooms and environmental surfaces are free of *C. difficile* spores. Currently, there are no easy to use, rapid methods for detecting *C. difficile* spores in environmental and patient samples. While kits (both immunoassay and molecular assays) are currently commercially available for the detection of *C. difficile* toxin, these kits do not detect *C. difficile* spores. Thus, there is a need for rapid and easy to use systems for the detection of *C. difficile* spores.

SUMMARY OF THE INVENTION

The present invention includes an isolated antibody that binds to a *Clostridium difficile* spore. In some embodiments, the spore is an ungerminated spore. In some embodiments, the spore is a germinated spore. In some embodiments, the antibody does not bind to *Clostridium difficile* vegetative cells. In some embodiments, the antibody does not bind to *C. difficile* toxin.

The present invention includes an isolated antibody that binds to hypothetical protein CD1021 of *Clostridium difficile* strain 630 having SEQ ID NO: 1, or a fragment of hypothetical protein CD1021. In some embodiments, the isolated antibody binds a fragment of hypothetical protein CD1021 including amino acid residues 505 to 604. In some embodiments, the isolated antibody binds a fragment of hypothetical protein CD1021 including amino acid residues 30 to 120. In some embodiments, the isolated antibody binds a fragment of hypothetical protein CD1021 including amino acid residues 194 to 293. In some embodiments, the isolated antibody binds to a fragment of hypothetical protein CD1021 including amino acid residues 203 to 217. In some embodiments, the isolated antibody binds to a fragment of hypothetical protein CD1021 including amino acid residues 333 to 347.

The present invention includes an isolated antibody that binds to the amino acid sequence SEQ ID NO:2.

The present invention includes an isolated antibody that binds to the amino acid sequence SEQ ID NO:9.

The present invention includes an isolated antibody that binds to the amino acid sequence SEQ ID NO:10.

The present invention includes an isolated antibody that binds to the amino acid sequence EGSSLQYKGDDPESY (SEQ ID NO:3).

The present invention includes an isolated antibody that binds to the amino acid sequence LKNETYKTKYHKYLE (SEQ ID NO:4).

The present invention includes an isolated antibody that binds to putative N-acetylmuramoyl-L-alanine amidase protein of *Clostridium difficile* strain 630 having SEQ ID NO: 5 or a fragment of the putative N-acetylmuramoyl-L-alanine amidase protein. In some embodiments, the isolated antibody binds to a fragment of the putative N-acetylmuramoyl-L-alanine amidase protein including amino acid residues 294 to 393. In some embodiments, the isolated antibody binds to a fragment of the putative N-acetylmuramoyl-L-alanine amidase protein including amino acid residues 582 to 596. In some embodiments, the isolated antibody binds to a fragment of the putative N-acetylmuramoyl-L-alanine amidase protein including amino acid residues 64 to 78.

The present invention includes an isolated antibody that binds to the amino acid sequence SEQ ID NO:6.

The present invention includes an isolated antibody that binds to the amino acid sequence YKLKDKNGGTTKTVA (SEQ ID NO:7).

The present invention includes an isolated antibody that binds to the amino acid sequence KFKEKPDADSIKLKY (SEQ ID NO:8).

The present invention includes a monoclonal antibody, or antigen binding fragment thereof, wherein the monoclonal antibody or antigen binding fragment inhibits the binding of an antibody of the present invention to its antigen target.

The present invention includes an antigen binding fragment of an isolated antibody of the present invention.

In some embodiments, an isolated antibody of the present invention is a polyclonal antibody. In some embodiments, an isolated antibody of the present invention is a monoclonal antibody. In some embodiments, the isolated antibody of the present invention does not bind to *Bacillus subtilis* spores or *Clostridium sporogenes* spores. In some embodiments, the antibodies and antigen binding fragments of the present invention are labeled.

The present invention includes a composition including one or more of the isolated antibodies of the present invention, or antigen binding fragments thereof.

The present invention includes a kit including one or more of the isolated antibodies of the present invention, or antigen binding fragments thereof.

The present invention includes a hybridoma cell line or transformed B cell line that produces a monoclonal antibody of the present invention.

The present invention includes an isolated polynucleotide sequence including the nucleic acid sequence coding for the heavy chain, the light chain, the heavy chain variable region, the light chain variable region, or one or more complementarity determining regions of a monoclonal antibody of the present invention. The present invention includes an expression vector including such an isolated polynucleotide sequence. The present invention includes a host cell including such an expression vector.

The present invention includes a method of preparing an anti-*Clostridium difficile* antibody, the method including immunizing a host organism with a polypeptide including at least a portion of a protein encoded by the *C. difficile* genome in an amount effective to generate an antibody response to the polypeptide. In some embodiments, the polypeptide including at least a portion of a protein encoded by the *C. difficile* genome is selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and fragments thereof. In some embodiments, the method further includes purifying the antibody preparation.

The present invention includes a method of preparing an anti-*Clostridium difficile* antibody, the method including expressing a nucleic acid sequence encoding at least a portion of a protein encoded by the *C. difficile* genome in an immunocompetent host organism. In some embodiments, the nucleic acid sequence encoding at least a portion of a protein encoded by the *C. difficile* genome encodes an amino acid sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and fragments thereof. In some embodiments, the method further includes purifying the antibody preparation.

The present invention includes a composition including at least two isolated antibodies or antigen-binding fragments thereof, wherein each isolated antibody binds to a distinct antigenic epitope of the *Clostridium difficile* spore.

In some embodiments of the composition, at least one isolated antibody or antigen-binding fragment thereof binds to hypothetical protein CD1021 of *C. difficile* strain 630 having SEQ ID NO: 1, or a polypeptide fragment of hypothetical protein CD1021. In some embodiments, the polypeptide fragment of hypothetical protein CD1021 is selected from SEQ ID NO:2, SEQ ID NO:3, SEQ ID NO:4, SEQ ID NO:9, SEQ ID NO:10, and fragments thereof.

In some embodiments of the composition, at least one isolated antibody or antigen-binding fragment thereof binds to putative N-acetylmuramoyl-L-alanine amidase protein of *C. difficile* strain 630 having SEQ ID NO: 5, or a fragment of the putative N-acetylmuramoyl-L-alanine amidase protein. In some embodiments, the polypeptide fragment of the putative N-acetylmuramoyl-L-alanine amidase protein is selected from the group consisting of SEQ ID NO:6, SEQ ID NO:7, SEQ ID NO:8, and fragments thereof.

In some embodiments of the composition, a first isolated antibody or antigen-binding fragment thereof binds to hypothetical protein CD1021 of *C. difficile* strain 630 having SEQ ID NO: 1, or a polypeptide fragment of hypothetical protein CD1021, and a second isolated antibody or antigen-binding fragment thereof binds to putative N-acetylmuramoyl-L-alanine amidase protein of *C. difficile* strain 630 having SEQ ID NO: 5, or a fragment of the putative N-acetylmuramoyl-L-alanine amidase protein. In some embodiments, the polypeptide fragment of hypothetical protein CD1021 is selected from SEQ ID NO:2, SEQ ID NO:3, SEQ ID NO:4, SEQ ID NO:9, SEQ ID NO:10, and fragments thereof. In some embodiments, the polypeptide fragment of the putative N-acetylmuramoyl-L-alanine amidase protein is selected from the group consisting of SEQ ID NO:6, SEQ ID NO:7, SEQ ID NO:8, and fragments thereof.

The present invention includes a kit including at least two isolated antibodies or antigen-binding fragments thereof, wherein each isolated antibody binds to a distinct antigenic epitope of the *Clostridium difficile* spore.

In some embodiments of the kit, at least one isolated antibody or antigen-binding fragment thereof binds to hypothetical protein CD1021 of *C. difficile* strain 630 having SEQ ID NO: 1, or a polypeptide fragment of hypothetical protein CD1021. In some embodiments, the polypeptide fragment of hypothetical protein CD1021 is selected from SEQ ID NO:2, SEQ ID NO:3, SEQ ID NO:4, SEQ ID NO:9, SEQ ID NO:10, and fragments thereof.

In some embodiments of the kit, at least one isolated antibody or antigen-binding fragment thereof binds to putative N-acetylmuramoyl-L-alanine amidase protein of *C. difficile* strain 630 having SEQ ID NO: 5, or a fragment of the putative N-acetylmuramoyl-L-alanine amidase protein. In some embodiments, the polypeptide fragment of the putative N-acetylmuramoyl-L-alanine amidase protein is selected from SEQ ID NO:6, SEQ ID NO:7, SEQ ID NO:8, and fragments thereof.

In some embodiments of the kit, a first isolated antibody or antigen-binding fragment thereof binds to hypothetical protein CD1021 of *C. difficile* strain 630 having SEQ ID NO: 1, or a polypeptide fragment of hypothetical protein CD1021, and a second isolated antibody or antigen-binding fragment thereof binds to putative N-acetylmuramoyl-L-alanine amidase protein of *C. difficile* strain 630 having SEQ ID NO: 5, or a fragment of the putative N-acetylmuramoyl-L-alanine amidase protein. In some embodiments, the polypeptide fragment of hypothetical protein CD1021 is selected from SEQ ID NO:2, SEQ ID NO:3, SEQ ID NO:4, SEQ ID NO:9, SEQ ID NO:10, and fragments thereof. In some embodiments, the polypeptide fragment of the putative N-acetylmuramoyl-L-alanine amidase protein is selected from SEQ ID NO:6, SEQ ID NO:7, SEQ ID NO:8, and fragments thereof.

The present invention includes a method of detecting the presence of a *Clostridium difficile* spore in a sample, the method including contacting the sample with one or more isolated antibodies of the present invention.

The present invention includes a method of detecting the presence of a *Clostridium difficile* spore in a sample, the method including contacting the sample with at least two isolated antibodies or antigen-binding fragments thereof, wherein each isolated antibody binds to a distinct antigenic epitope of the *C. difficile* spore.

The present invention includes a method of detecting the presence of a *Clostridium difficile* spore in a sample, the method including: contacting the sample with a first isolated antibody or antigen-binding fragment thereof, wherein the first isolated antibody binds to a first antigenic epitope of the *C. difficile* spore; and contacting the sample with a second isolated antibody or antigen-binding fragment thereof, wherein the second isolated antibody binds to a second antigenic epitope of the *C. difficile* spore.

In some embodiments of the methods of the present invention, at least one isolated antibody or antigen-binding fragment thereof binds to hypothetical protein CD1021 of *C. difficile* strain 630 having SEQ ID NO: 1, or a polypeptide fragment of hypothetical protein CD1021. In some embodiments, the polypeptide fragment of hypothetical protein CD1021 is selected from SEQ ID NO:2, SEQ ID NO:3, SEQ ID NO:4, SEQ ID NO:9, SEQ ID NO:10, and fragments thereof.

In some embodiments of the methods of the present invention, at least one isolated antibody or antigen-binding fragment thereof binds to putative N-acetylmuramoyl-L-alanine amidase protein of *C. difficile* strain 630 having SEQ ID NO: 5, or a fragment of the putative N-acetylmuramoyl-L-alanine amidase protein. In some embodiments, the polypeptide fragment of the putative N-acetylmuramoyl-L-alanine amidase protein is selected from SEQ ID NO:6, SEQ ID NO:7, SEQ ID NO:8, and fragments thereof.

In some embodiments of the methods of the present invention, a first isolated antibody or antigen-binding fragment thereof binds to hypothetical protein CD1021 of *C. difficile* strain 630 having SEQ ID NO: 1, or a polypeptide fragment of hypothetical protein CD1021, and a second isolated antibody or antigen-binding fragment thereof binds to putative N-acetylmuramoyl-L-alanine amidase protein of *C. difficile* strain 630 having SEQ ID NO: 5, or a fragment of the putative N-acetylmuramoyl-L-alanine amidase protein. In some embodiments, the polypeptide fragment of hypothetical protein CD1021 is selected from SEQ ID NO:2, SEQ ID NO:3, SEQ ID NO:4, SEQ ID NO:9, SEQ ID NO:10, and fragments thereof. In some embodiments, the polypeptide fragment of the putative N-acetylmuramoyl-L-alanine amidase protein is selected from SEQ ID NO:6, SEQ ID NO:7, SEQ ID NO:8, and fragments thereof.

Unless otherwise specified, "a," "an," "the," and "at least one" are used interchangeably and mean one or more than one.

BRIEF DESCRIPTION OF THE FIGURES

FIG. 1 represents the homology between the amino acid sequences for hypothetical CD1021 proteins from *C. difficile* strain 630 (SEQ ID NO:1, corresponding to GenBank Accession No. YP_001087502), *C. difficile* QCD-32g58 (SEQ ID NO:11, corresponding to GenBank Accession No. ZP_01804840), *C. difficile* QCD-32g58 (SEQ ID NO:12, corresponding to GenBank Accession No. ZP_01804841), *C. difficile* QCD-32g58 (SEQ ID NO:21, translated from the region corresponding to nucleotides 461827 to 462825 of GenBank Accession No. NZ_$_{AAML}$04000007), *C. difficile* QCD-32g58 (SEQ ID NO:22, translated from region corresponding to nucleotides 462824 to 463732 of GenBank Accession No. NZ_AAML04000007), and from *C. difficile* QCD-66c26 (SEQ ID NO:23, translated from the complement of the region corresponding to nucleotides 15690 to 17597 of GenBank Accession No. NZ_ABFD01000037). The sequences were aligned using the multiple sequence alignment program CustalW, which is publicly available. The consensus sequence as shown is SEQ ID NO:38. Amino acid residues that are identical in at least four of the six hypothetical proteins are shown in the consensus sequence. An "" residue in the consensus sequence indicates that two or more of the aligned sequences showed nonidentity at the respective residue or it indicates that sequence information was lacking for the respective residue in three or more of the aligned sequences. A "•" symbol located at any given position in one of the aligned sequences indicates that amino acid position was unreported in the corresponding GenBank entry.

DETAILED DESCRIPTION

The present invention relates to antibodies that bind to the endospore of the bacterium *Clostridium difficile* (also referred to herein as "*C. difficile*," "*C. diff.*," "*c. diff.*," "*C-diff*," or "*C.D*"). Such spore-specific antibodies are useful, for example, in the detection of *C. difficile* endospores in environmental, biological, and food samples. Only a few genera of bacteria, such as, for example, *Bacillus* and *Clostridium*, are capable of forming endospores. Bacterial endospores are highly resistant to hostile physical and chemical conditions, proving to be one of the most durable types of cells found in nature. They can survive high heat, drying, radiation, and many damaging chemicals and are a dormant form of the bacterium that allows it to survive sub-optimal environmental conditions. Endospores can survive for a very long time and then return to a growing state, a process termed germination. Because endospores are resistant to heat, radiation, disinfectants, and desiccation, they are difficult to eliminate from medical and pharmaceutical materials and are a frequent cause of contamination.

Antibodies of the present invention bind to the endospore (also referred to herein as "spore") of the bacterium *C. difficile*. As used herein, the terms "antibody" or "antibodies" are used interchangeably. An antibody of the present invention may bind to both viable spores and inactivated *C. difficile* spores. Spores may be inactivated by any of a variety of methods, including, but not limited to, for example, treatment with formalin, formaldehyde, glutaraldehydes, chemical disinfectants, autoclaving, and ultraviolet radiation. Antibodies of the present invention may bind to both germinated and ungerminated *C. difficile* spores. Antibodies of the present invention may bind to ungerminated *C. difficile* spores and not bind to germinated *C. difficile* spores. Antibodies of the present invention may bind to germinated *C. difficile* spores and not bind to ungerminated *C. difficile* spores. Methods for the preparation of ungerminated spores and germinated spores are well known to the skilled artisan. Briefly, bacterial spores are generally prepared by growing the bacteria on media such as tryptic soy agar or in tryptic soy broth until most cells turn into spores. Spores are collected by centrifugation and washed several times with a buffer such as PBS. The suspension can be treated with alcohol to kill vegetative cells and washed to collect spores (see, for example, Long and Williams, 1958, *J Bacteriol:* 76:332 and Powers, 1968, *Appl Microbiol;* 16:180-181). Spore germination can be triggered by a variety of methods. See, for example, Gould, 1970, *J Appl Bacteriol;* 33:34-49; Foerster and Foster, 1966, *J Bacteriol;* 91:1168-1177; Moir and Smith, 1990, *Ann Rev Microbiol;* 44:531-553; and U.S. Patent Application Serial No. 2003/0175318A1.

Antibodies of the present invention may bind *C. difficile* spores and not bind to the spores of other endospore-forming bacteria. Antibodies of the present invention may bind *C. difficile* spores and not bind to the spores of other endospore-forming bacteria of the Firmicute phylum, such as for example, endospores produced by any of the various species of the *Clostridium* or *Bacillus* genera. Species of the *Clostridium* and *Bacillus* genera of bacteria include, but are not limited to, *Clostridium aceticum*, *Clostridium acetobutylicum*, *Clostridium botulinum*, *Clostridium butyricum*, *Clostridium carnis*, *Clostridium chauvoei*, *Clostridium denitrificans*, *Clostridium fervidus*, *Clostridium formicoaceticum*, *Clostridium novyi*, *Clostridium pasteurianum*, *Clostridium perfringens*, *Clostridium septicum*, *Clostridium sporogenes*, *Clostridium tetani*, *Clostridium thermoaceticum*, *Clostridium thermocellum*, *Clostridium thermosacchrolyticum*, *Clostridium tyrobutyricum*, *Clostridium welchii*, *Bacillus agaradhaerens*, *Bacillus alcalophilus*, *Bacillus amyloliquefaciens*, *Bacillus anthracis*, *Bacillus atrophaeus*, *Bacillus azotoformans*, *Bacillus badius*, *Bacillus* benzoevorans, Bacillus carboniphilus, Bacillus cereus, Bacillus chitinolyticus, Bacillus circulans, Bacillus clarkii, Bacillus clausii, Bacillus coagulans, Bacillus cohnii, Bacillus edaphicus, Bacillus ehimensis, Bacillus fastidiosus, Bacillus firmus, Bacillus flexus, Bacillus fumarioli, Bacillus fusiformis, Bacillus gibsonii, Bacillus globisporus, Bacillus halmapalus, Bacillus haloalkaliphilus, Bacillus halodenitrificans, Bacillus halodurans, Bacillus halophilus, Bacillus horikoshii, Bacillus horti, Bacillus infernos, Bacillus insolitus, Bacillus kaustophilus, Bacillus laevolacticus, Bacillus lentus, Bacillus licheniformis, Bacillus marinus, Bacillus megaterium, Bacillus methanolicus, Bacillus mojavensis, Bacillus mucilaginosus, Bacillus mycoides, Bacillus naganoensis, Bacillus niacini, Bacillus oleronius, Bacillus pallidus, Bacillus pasteurii, Bacillus pseudalcaliphilus, Bacillus Pseudofirmus, Bacillus pseudomycoides, Bacillus psychrophilus, Bacillus psychrosaccharolyticus, Bacillus pumilus, Bacillus schlegelii, Bacillus silvestris, Bacillus simplex, Bacillus siralis, Bacillus smithii, Bacillus sphaericus, Bacillus sporothermodurans, Bacillus stearothermophilus, Bacillus subtilis, Bacillus thermoamylovorans, Bacillus thermocatenulatus, Bacillus thermocloaceae, Bacillus thermodenitrificans, Bacillus thermoglucosidasius, Bacillus thermoleovorans, Bacillus thermosphaericus, Bacillus thuringiensis, Bacillus tusciae, Bacillus vallismortis, Bacillus vedderi, Bacillus vulcani, and Bacillus weihenstephanensis.

Antibodies of the present invention may bind C. difficile spores and not bind to the spores of other bacteria, such as, for example, Desulfotomaculum, Sporolactobacillus, Brevibacillus, Sporosarcina, and Thermoactinomyces.

In some embodiments, antibodies of the present invention bind to C. difficile spores and do not bind to the spores of Bacillus subtilis (also referred to herein as B. subtilis) and Clostridium sporogenes (also referred to herein as C. sporogenes).

Antibodies of the present invention may bind to C. difficile spores and not bind to C. difficile vegetative cells. Antibodies of the present invention may bind to C. difficile spores and not bind to vegetative cells of other endospore-forming bacteria, including any of those described herein. In some embodiments, antibodies of the present invention do not bind to vegetative cells of C. difficile, B. subtilis, and C. sporogenes. Methods for culturing vegetative cells of a wide variety of Clostridium and Bacillus species, including, but not limited C. difficile, C. sporogenes, and B. subtilis, are well known to the skilled artisan. See, for example, Madigan et al., 2003, Brock Biology of Microorganisms, Prentice Hall; and Cappucino, 2005, Microbiology Laboratory Manual, Benjamin Cummings.

Pathogenic C. difficile strains produce various toxins. The best characterized are enterotoxin (toxin A) and cytotoxin (toxin B) and these two toxins are responsible for the diarrhea and inflammation seen in infected patients (see, for example, Gianfrilli et al., 1984, Microbiologica; 7:375-9). Antibodies of the present invention may bind to C. difficile spores and not bind to a toxin produced by C. difficile, for example, the antibody may not bind to toxin A and/or toxin B. Methods for preparing C. difficile toxin A and toxin B and determining if an antibody binds to C. difficile toxin A and/or toxin B are well known to the skilled artisan. See, for example, U.S. Pat. Nos. 4,530,833; 4,533,630; 4,863,852; 4,879,218; 5,231,003; 5,610,023; 5,965,375; 6,503,722; 6,939,548; and 7,179,611.

Bacterial endospores, including C. difficile endospores, are encased in a multilayered protein structure formed by the ordered assembly of many polypeptides. The endospore contains four protective layers, the core, the cortex, the coat, and the exosporium. The outermost layer of the spore is the exosporium, a thin covering made of protein. Interior to this is the spore coat which is made up of highly cross-linked keratin and layers of spore-specific proteins. The spore coat is impermeable to many toxic molecules and may also contain enzymes that are involved in germination. The cortex lies beneath the spore coat and consists of peptidoglycan. The core wall lies beneath the cortex and surrounds the protoplast or core of the endospore. The core has normal cell structures, such as DNA and ribosomes, but is metabolically inactive.

Some embodiments of the present invention include antibodies that bind to a spore-specific protein, such as, for example, an exosporium protein, a spore coat protein, a spore cortex protein, a spore inner membrane protein, or a spore core protein of C. difficile. Such an antibody may bind to a spore-specific protein found on one or more endospore-forming bacteria of the Firmicute phylum described herein. In some embodiments, the antibody binds to a spore-specific protein found in C. difficile, but does not bind to the spore-specific protein other endospore-forming bacteria of the Firmicute phylum, such as, for example, B. subtilis and C. sporogenes.

Some embodiments of the present invention include antibodies that bind to a spore coat assembly protein of C. difficile. One such spore coat assembly protein is the CotH protein (also referred to herein as "cotH"). The CotH protein is a structural component of the spore coat and has been well characterized in B. subtilis. It is involved in directing the assembly of coat proteins and in stabilizing coat proteins. See, for example, Naclerio et al., 1996, J Bacteriol; 178 (15):4375-4380 and Zilha et al., 1999, J Bacteriol; 181:2631-2633). The present invention includes antibodies that bind to a putative CotH protein in C. difficile.

The complete genome sequence of C. difficile strain 630 has been determined and is available in the GenBank® sequence database maintained by the National Center for Biotechnology Information (NCBI), National Library of Medicine (NLM), National Institutes of Health (NIH). See also, Sebaihia et al., 2006, Nat. Genet; 38 (7):779-786). Strain 630 is multi-drug resistant and was isolated from a patient with severe pseudomembraneous colitis that had spread to dozens of other patients on the same ward in Zurich, Switzerland in 1982 (Wren, 2006, Future Microbiol; 1 (3): 243-245). Thus, strain 630 has the genetic attributes of a fully virulent, highly transmissible, drug resistant strain.

Efforts are currently under way to obtain the complete genome sequences of other C. difficile strains. The Sanger Institute (Wellcome Trust Genome Campus, Hinxton, Cambridge, UK) is sequencing the genome of C. difficile strain R20291. C. difficile strain 820291 was isolated in Stoke Mandeville, UK, and is closely related to the North American hypervirulent BI strains. Washington University in St. Louis (St. Louis, Mo.) is sequencing the genome of C. difficile QCD-32g58

A thorough search of all the GenBank entries for C. difficile strain 630 identified hypothetical protein CD1021 (YP_001087502), which demonstrates a conserved domain (amino acid residues 90 to 393) which is homologous to the spore coat assembly protein H (cotH) of B. subtilis. The analysis was performed using conserved domain search tools available from the NCBI. Hypothetical Protein CD1021 of C. difficile 630 (GenBank Accession No. YP_001087502) has the amino acid sequence SEQ ID NO:1. See Sebaihia et al., 2006, Nat. Genet; 38 (7):779.

Some embodiments of the present invention include antibodies that bind to the hypothetical protein CD1021 of C. difficile, and fragments thereof. An antibody of the present invention may bind to a hypothetical protein CD1021 in a variety of *C. difficile* strains, including, but not limited to, any of the *C. difficile* strains discussed herein. For example, an antibody of the present invention may bind to the hypothetical protein CD1021 of *C. difficile* strain 630, *C. difficile* strain R20291, *C. difficile* strain QCD-32q58, *C. difficile* strain QCD-66c26, *C. difficile* ATCC 43255, *C. difficile* ATCC 43593, *C. difficile* ATCC 43594, *C. difficile* ATCC 43596, *C. difficile* ATCC 43597, *C. difficile* ATCC 43598, *C. difficile* ATCC 43603, *C. difficile* ATCC 9689, and/or *C. difficile* ATCC 700792. Antibodies of the present invention include antibodies that bind to the hypothetical protein CD1021 of *C. difficile* strain 630 having SEQ ID NO:1.

Some embodiments of the present invention include antibodies that bind to polypeptide fragments of the hypothetical protein CD1021 of *C. difficile*. A polypeptide fragment may be, for example, about 50, about 100, about 200, about 300, about 400, about 500, or about 600 amino acids in length. A polypeptide fragment may be, for example, about 10, about 15, about 20, about 25, about 30, about 35, about 40, or about 45 amino acids in length. A polypeptide fragment may be about 8-20, about 12-15, or about 10-20 amino acids in length.

Some embodiments of the present invention include antibodies that bind to polypeptide fragments of the hypothetical protein CD1021 of *C. difficile* strain 630 (SEQ ID NO:1). For example, the present invention includes antibodies that bind to a polypeptide including residues 505-604 of hypothetical protein CD1021 of *C. difficile* strain 630 (SEQ ID NO:2), antibodies that bind to a polypeptide including residues 30-120 of hypothetical protein CD1021 of *C. difficile* strain 630 (SEQ ID NO:9), antibodies that bind to a polypeptide including residues 194-293 of hypothetical protein CD1021 of *C. difficile* strain 630 (SEQ ID NO:10), antibodies that bind to a polypeptide including residues 203 to 217 of hypothetical protein CD1021 of *C. difficile* strain 630 (SEQ ID NO:3), and antibodies that bind to a polypeptide including residues 333 to 347 of hypothetical protein CD1021 of *C. difficile* strain 630 (SEQ ID NO:4).

The spore cortex, a thick layer of peptidoglycan, is responsible for maintaining the highly dehydrated state of the spore and contributes to the extreme dormancy and heat resistance of the spores. Bacterial spore germination includes a series of degradation events that lead to the irreversible loss of spore dormancy and the rehydration of the core. The spore contains enzymes that are involved in germination. Thus, an antibody that binds to a spore-specific protein involved in germination may be used to identify germinating spores. The present invention includes antibodies that bind to a spore-specific protein involved in germination. Such an antibody may bind to germinated spores but not bind to ungerminated spores. Such an antibody may bind to ungerminated spores but not bind to germinated spores.

Cortex lytic enzymes, including the amidase N-acetylmuramoyl L-alanine amidase, play a key role in germination, resulting in hydrolysis of the cortex (see, for example, Moriyama et al., 1996, *J Bacteriol*; 181:2373-2378). The present invention includes antibodies that bind to a *C. difficile* amidase, including antibodies that bind to the N-acetylmuramoyl-L-alanine amidase of *C. difficile*.

A thorough search of all the GenBank entries for *C. difficile* strain 630 identified cell surface protein (putative N-acetylmuramoyl-L-alanine amidase, YP_001087517, also referred to herein as "CD1036") which has conserved domains CW_binding_2 (putative cell wall binding repeat 2; 174 to 265, 275 to 368, 381 to 461) and Amidase_3 (N-acetylmuramoyl-L-alanine amidase, 493 to 673). The putative N-acetylmuramoyl-L-alanine amidase cell surface protein of *C. difficile* 630 (GenBank Accession No. YP_001087517) has the amino acid sequence SEQ ID NO:5. See Sebaihia et al., 2006, Nat. Genet; 38 (7):779-786.

The present invention includes antibodies that bind to the putative N-acetylmuramoyl-L-alanine amidase of *C. difficile*, and fragments thereof. An antibody of the present invention may bind to the putative N-acetylmuramoyl-L-alanine amidase in a variety of *C. difficile* strains, including, but not limited to, any of the *C. difficile* strains discussed herein. For example, an antibody of the present invention may bind to the putative N-acetylmuramoyl-L-alanine amidase of *C. difficile* strain 630, *C. difficile* strain R20291, *C. difficile* strain QCD-32q58, *C. difficile* ATCC 43255, *C. difficile* ATCC 43593, *C. difficile* ATCC 43594, *C. difficile* ATCC 43596, *C. difficile* ATCC 43597, *C. difficile* ATCC 43598, *C. difficile* ATCC 9689, and/or *C. difficile* ATCC 700792. Antibodies of the present invention include antibodies that bind to the putative N-acetylmuramoyl-L-alanine amidase of *C. difficile* strain 630 having SEQ ID NO:5.

Some embodiments of the present invention include antibodies that bind to polypeptide fragments of the putative N-acetylmuramoyl-L-alanine amidase. A polypeptide fragment may be, for example, about 50, about 100, about 200, about 300, about 400, about 500, or about 600 amino acids in length. A polypeptide fragment may be, for example, about 10, about 15, about 20, about 25, about 30, about 35, about 40, or about 45 amino acids in length. A polypeptide fragment may be about 8-20, about 12-15, or about 10-20 amino acids in length. The present invention includes antibodies that bind to polypeptide fragments of the putative N-acetylmuramoyl-L-alanine amidase of *C. difficile* strain 630 having SEQ ID NO:5. For example, the present invention includes antibodies that bind to a polypeptide including residues 294-393 of putative N-acetylmuramoyl-L-alanine amidase of *C. difficile* strain 630 (SEQ ID NO:6), antibodies that bind to a polypeptide including residues 582-596 of putative N-acetylmuramoyl-L-alanine amidase of *C. difficile* strain 630 (SEQ ID NO:7), and antibodies that bind to a polypeptide including residues 64-78 of putative N-acetylmuramoyl-L-alanine amidase of *C. difficile* strain 630 (SEQ ID NO:8).

Antibodies of the present invention include, but are not limited to, polyclonal antibodies, affinity-purified polyclonal antibodies, monoclonal antibodies, human antibodies, humanized antibodies, chimeric antibodies, anti-idiotypic antibodies, multispecific antibodies, single chain antibodies, single-chain Fvs (scFv), disulfide-linked Fvs (sdFv), Fab fragments, F(ab') fragments, F(ab')2 fragments, Fv fragments, diabodies, linear antibodies fragments produced by a Fab expression library, fragments comprising either a VL or VH domain, intracellularly-made antibodies (i.e., intrabodies), and antigen-binding antibody fragments thereof. Any of a wide variety of target antigens may be used to produce the antibodies of the present invention, including, but not limited to, *C. difficile* cells, spores or toxins, proteins, peptides, carbohydrates and combinations thereof. Proteins and peptides may be, for example, naturally occurring, chemically synthesized, or recombinantly produced. An antigen may be conjugated to a carrier.

Also included in the present invention are various antibody fragments, also referred to as antigen binding fragments, which include only a portion of an intact antibody, generally including an antigen binding site of the intact antibody and thus retaining the ability to bind antigen. Fragments can be obtained via chemical or enzymatic treatment of an intact or complete antibody or antibody chain. Fragments can also be obtained by recombinant means. Examples of antibody fragments include, for example, Fab, Fab', Fd, Fd', Fv, dAB, and F(ab')2 fragments produced by proteolytic digestion and/or reducing disulfide bridges and fragments produced from an Fab expression library. Such antibody fragments can be generated by techniques well known in the art. Antibodies of the present invention can include the variable region(s) alone or in combination with the entirety or a portion of the hinge region, CH1 domain, CH2 domain, CH3 domain and/or Fc domain(s). The term "antigen-binding fragment" refers to a polypeptide fragment of an immunoglobulin or antibody that binds antigen or competes with the intact antibody for antigen binding.

The antibodies of the present invention can be of any type (such as, for example, IgG, IgE, IgM, IgD, IgA and IgY), class (such as, for example, IgG1, IgG2, IgG3, IgG4, IgA1 and IgA2) or subclass of immunoglobulin molecule. In some embodiments, the immunoglobulin is an IgG. Immunoglobulins can have both heavy and light chains. An array of IgG, IgE, IgM, IgD, IgA, and IgY heavy chains can be paired with a light chain of the kappa or lambda form.

The antibodies of the invention can be from any animal origin, including birds and mammals. In some embodiments, the antibodies are human, murine, rat, donkey, sheep, rabbit, goat, guinea pig, camel, horse, llama, camel, or chicken antibodies. As used herein, "human" antibodies include antibodies having the amino acid sequence of a human immunoglobulin and include antibodies isolated from human immunoglobulin libraries or from animals transgenic for one or more human immunoglobulins.

Antibodies of the present invention may be a polyclonal antibody. The term "polyclonal antibody" refers to an antibody produced from more than a single clone of plasma cells. In contrast "monoclonal antibody" refers to an antibody produced from a single clone of plasma cells. The preparation of polyclonal antibodies is well known.

A polyclonal antibody to a target antigen may be obtained by immunizing any of a variety of host animals with an immunogen. Any of a wide variety of immunization protocols may be used. The host animal may be any mammal, for example, a mouse, hamster, rat, rabbit, guinea pig, goat, sheep, horse, cow, buffalo, bison, camel, or llama. A host animal may be a bird, for example, a chicken or a turkey. In some embodiments, an antibody preparation, rather than obtained from a blood sample, is obtained from another fluid source, for example, from milk, colostrums, egg white, or egg yolk. In some embodiments, an antibody preparation is obtained, not by immunizing a host animal with the target antigen, but rather, from an individual with a prior exposure to the antigen or from pooled serum, for example, from pooled human serum.

It may be useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

Some embodiments of the present invention include antiserum that binds to a C. difficile spore. As used herein, antiserum refers to the blood from an immunized host animal from which the clotting proteins and red blood cells (RBCs) have been removed. An antiserum (also referred to herein as an "antiserum preparation," "crude antiserum," or "raw antiserum") still possesses immunoglobulins of all classes as well as other various serum proteins. Thus, in addition to antibodies that recognize the target antigen, the antiserum also contains antibodies to various non-target antigens that can sometimes react non-specifically in immunological assays.

In some embodiments of the present invention, an antibody may be enriched. Such enrichment may eliminate non-immunoglobulin proteins from the preparation and/or enrich for one or more classes of immunoglobulin (such as, for example, IgG) within the sample. Any of a variety of methods may be used to obtain such an enriched antibody, including, but not limited to, those described herein. Methods of eliminating non-immunoglobulin serum proteins from an antibody preparation and methods for enriching for the IgG fraction are well known in the art. For example, ammonium sulfate precipitation, Protein A binding, Protein G binding, or caprylic acid precipitation may be used to enrich for the IgG class of antibodies.

Antibodies of the present invention include antibodies with enhanced avidity for the target antigen. Such antibodies may be prepared by antigen affinity immunoadsorption. Antigen affinity immunoadsorption may be carried out by any of a variety of means. For example, antigen affinity immunoadsorption may be carried out by antigen affinity column chromatography. Column chromatography may be carried out by any mechanical means, for example, carried out in a column run with or without pressure, carried out in a column run from top to bottom or bottom to top, or the direction of the flow of fluid in the column may be reversed during the chromatography process. Alternatively, antigen affinity immunoadsorption may be carried out by means other than column chromatography. For example, affinity immunoadsorption may be carried out using a batch process in which the solid support is separated from the liquid used to load, wash, and elute the sample by any suitable means, including gravity, centrifugation, or filtration. Affinity immunoadsorption also may be carried out by contacting the sample with a filter that adsorbs or retains some molecules in the sample more strongly than others. The antigen affinity column may be prepared by any of a variety of methods, including, but not limited to, those described herein. The binding of an antibody preparation to an antigen affinity column may be carried out by any of a wide variety of immunoadsorption methods, including, but not limited to, those described herein. The binding of the antibody preparation to the antigen affinity column may occur in a variety of buffers or salts including, but not limited to, sodium, potassium, ammonium, chloride, acetate, phosphate, citrate, Tris buffers and/or organic buffers with a buffering capacity near neutrality. Specific examples of such buffers and salts include, for example, Tris, sodium phosphate, potassium phosphate, ammonium phosphate, sodium chloride, potassium chloride, ammonium chloride, sodium citrate, potassium citrate, ammonium citrate, sodium acetate, potassium acetate, or ammonium acetate.

Antibodies of the present invention include monoclonal antibodies. A population of monoclonal antibodies is homogeneous. All of the monoclonal antibodies in the preparation recognize the same epitope on the target molecule and all of the monoclonal antibodies have the same affinity. As used herein, "affinity" is the binding strength of the interaction of a monoclonal antibody with its antigenic epitope. As used herein, an "epitope" is the portion of an antigen bound by an antibody. The higher the affinity, the tighter the association between antigen and antibody, and the more likely the antigen is to remain in the binding site.

Monoclonal antibodies of the present invention include, but are not limited to, humanized antibodies, chimeric antibodies, single chain antibodies, single-chain Fvs (scFv), disulfide-linked Fvs (sdFv), Fab fragments, F(ab') fragments, F(ab')2 fragments, Fv fragments, diabodies, linear antibodies fragments produced by a Fab expression library, fragments including either a VL or VH domain, intracellularly-made antibodies (i.e., intrabodies), and antigen-binding antibody fragments thereof.

Monoclonal antibodies of the present invention can be produced by an animal (including, but not limited to, human, mouse, rat, rabbit, hamster, goat, horse, chicken, or turkey), chemically synthesized, or recombinantly expressed. Monoclonal antibodies of the present invention can be purified by any method known in the art for purification of an immunoglobulin molecule, for example, by chromatography (e.g., ion exchange, affinity, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Monoclonal antibodies of the present invention may be of any isotype. The monoclonal antibodies of the present invention may be, for example, murine IgM, IgG1, IgG2a, IgG2b, IgG3, IgA, IgD, or IgE. The monoclonal antibodies of the present invention may be, for example, human IgM, IgG1, IgG2, IgG3, IgG4, IgA1, IgA2, IgD, or IgE. In some embodiments, the monoclonal antibody may be murine IgG2a, IgG1, or IgG3. With the present invention, a given heavy chain may be paired with a light chain of either the kappa or the lambda form.

Monoclonal antibodies can be obtained by various techniques familiar to those skilled in the art. For example, spleen cells from an animal immunized with a desired antigen are immortalized, commonly by fusion with a myeloma cell (see, for example, Kohler and Milstein, 1976, *Eur J Immunol;* 6:511-519; J. Goding In "Monoclonal Antibodies: Principles and Practice," Academic Press, pp 59-103 (1986); and Harlow et al., Antibodies: A Laboratory Manual, page 726 (Cold Spring Harbor Pub. (1988)). Monoclonal antibodies can be isolated and purified from hybridoma cultures by techniques well known in the art. Other known methods of producing transformed B cell lines that produce monoclonal antibodies may also be used. Monoclonal antibodies of the present invention may be produced by recombinant DNA techniques, for example, produced by phage display or by combinatorial methods. See, for example, U.S. Pat. No. 5,223,409; WO 92/18619; WO 91/17271; WO 92/20791; WO 92/15679; WO 93/01288; WO 92/01047; WO 92/09690; or WO 90/02809. Such methods can be used to generate human monoclonal antibodies.

Monoclonal antibodies of the present invention include chimeric antibodies. A chimeric antibody is one in which different portions are derived from different animal species. For example, chimeric antibodies can be obtained by splicing the genes from a mouse antibody molecule with appropriate antigen specificity together with genes from a human antibody molecule of appropriate biological specificity. See, for example, Takeda et al., 1985, *Nature;* 314:544-546.

A therapeutically useful antibody may be derived from a "humanized" monoclonal antibody. Humanized monoclonal antibodies are produced by transferring one or more CDRs from the heavy and light variable chains of a mouse (or other species) immunoglobulin into a human variable domain, then substituting human residues into the framework regions of the murine counterparts. The use of antibody components derived from humanized monoclonal antibodies obviates potential problems associated with immunogenicity of murine constant regions. Techniques for producing humanized monoclonal antibodies can be found, for example, in Jones et al., 1986, *Nature;* 321:522 and Singer et al., 1993, *J Immunol:* 150:2844. The constant region of a humanized monoclonal antibody of the present invention can be that from human immunoglobulin belonging to any isotype. It may be, for example, the constant region of human IgG. The framework regions of the constant region derived from human immunoglobulin are not particularly limited.

An intact antibody molecule has two heavy (H) chain variable regions (abbreviated herein as VH) and two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al., *J. Mol. Biol.* 1987; 196: 901-917). Each VH and VL is composed of three CDR's and four FRs, arranged from amino-terminus to carboxy-terminus in the following order: FR1, CDR1, FR2, CDR2, FR3, CDR3, FR4. The present invention includes an antibody with the heavy chain, the light chain, the heavy chain variable region, the light chain variable region, and/or one or more complementarity determining regions of a monoclonal antibody of the present invention.

The present invention includes bispecific or bifunctional antibodies. A bispecific or bifunctional antibody is an artificial hybrid antibody having two different heavy/light chain pairs and two different binding sites. Bispecific antibodies can be produced by a variety of methods including fusion of hybridomas or linking of F(ab') fragments. See, for example, Songsivilai and Lachmann, 1990, *Clin Exp Immunol;* 79:315-321 and Kostelny et al., 1992, *J Immunol;* 148:1547-1553. In addition, bispecific antibodies can be formed as "diabodies" (Holliger et al., 1993, *PNAS USA:* 90:6444-6448) or "Janusins" (Traunecker et al., 1991, *EMBO J;* 10:3655-3659 and Traunecker et al., 1992, *Int J Cancer Suppl;* 7:51-52).

Also included in the present invention are hybridoma cell lines, transformed B cell lines, and host cells that produce the monoclonal antibodies of the present invention; the progeny or derivatives of these hybridomas, transformed B cell lines, and host cells; and equivalent or similar hybridomas, transformed B cell lines, and host cells. Progeny or derivatives thereof may produce an antibody with one or more of the identifying characteristics, such as, for example, isotype and antigen specificity, of the antibody produced by the parental line.

The present invention further provides an isolated polynucleotide molecule having a nucleotide sequence encoding a monoclonal antibody of the invention. The present invention is further directed to an isolated polynucleotide molecule having a nucleotide sequence that has at least 75%, at least 80%, at least 85%, at least 90%, at least 95%, at least 96%, at least 97%, at least 98%, or at least 99% sequence identity to nucleotide sequence encoding a monoclonal antibody of the invention. The invention also encompasses polynucleotides that hybridize under high stringency to a nucleotide sequence encoding an antibody of the invention, or a complement thereof. As used herein "stringent conditions" refer to the ability of a first polynucleotide molecule to hybridize, and remain bound to, a second, filter-bound polynucleotide molecule in 0.5 M NaHPO4, 7% sodium dodecyl sulfate (SDS), and 1 mM EDTA at 65° C., followed by washing in 0.2×SSC/ 0.1% SDS at 42° C. (see Ausubel et al. (eds.), Current Protocols in Molecular Biology, Vol. 1, Green Publishing Associates, Inc., and John Wiley & Sons, Inc., NY, at p. 2.10.3 (1989)). Also included in the present invention are polynucleotides that encode one or more of the CDR regions or the heavy and/or light chains of a monoclonal antibody of the present invention. General techniques for cloning and sequencing immunoglobulin variable domains and constant regions are well known. See, for example, Orlandi et al., 1989, *PNAS USA;* 86:3833.

The present invention also includes recombinant vectors including an isolated polynucleotide of the present invention. The vector can be, for example, in the form of a plasmid, a viral particle, or a phage. The appropriate DNA sequence can be inserted into a vector by a variety of procedures. In general, the DNA sequence is inserted into an appropriate restriction endonuclease site(s) in a vector by procedures known in the art. Such procedures are deemed to be within the scope of those skilled in the art. Large numbers of suitable vectors and promoters are known to those of skill in the art, and are commercially available. The following vectors are provided by way of example. Bacterial vectors include, for example, pQE70, pQE60, pQE-9, pBS, pD10, phagescript, psiX174, pbluescript SK, pbsks, pNH8A, pNH16a, pNH18A, pNH46A, ptrc99a, pKK223-3, pKK233-3, pDR540, and pRIT5. Eukaryotic vectors include, for example, pWLNEO, pSV2CAT, pOG44, pXT1, pSG, pSVK3, pBPV, pMSG, and pSVL. However, any other plasmid or vector can be used.

Some embodiments of the present invention also include host cells containing the above-described vectors. The host cell can be a higher eukaryotic cell, such as a mammalian or insect cell, or a lower eukaryotic cell, such as a yeast cell. Or, the host cell can be a prokaryotic cell, such as a bacterial cell, or a plant cell. Introduction of a vector construct into the host cell can be effected by any suitable techniques, such as, for example, calcium phosphate transfection, DEAE-Dextran mediated transfection, or electroporation. (Davis, L., et al., Basic Methods in Molecular Biology (1986)).

Monoclonal antibodies of the present invention can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y. (1989).

Also included in the present invention are phage display libraries expressing one or more hypervariable regions from a monoclonal antibody of the present invention, and clones obtained from such a phage display library. A phage display library is used to produce antibody derived molecules. Gene segments encoding the antigen-binding variable domains of antibodies are fused to genes encoding the coat protein of a bacteriophage. Bacteriophage containing such gene fusions are used to infect bacteria, and the resulting phage particles have coats that express the antibody-fusion protein, with the antigen-binding domain displayed on the outside of the bacteriophage. Phage display libraries can be prepared, for example, using the Ph.D.™-7 Phage Display Peptide Library Kit (Catalog No. E8100S) or the Ph.D.™-12 Phage Display Peptide Library Kit (Catalog No. E8110S) available from New England Biolabs Inc., Ipswich, Mass. See also, Smith and Petrenko, 1997, *Chem Rev;* 97:391-410.

The antibodies of the present invention may be coupled directly or indirectly to a substrate or detectable marker by techniques well known in the art. A detectable marker is an agent detectable, for example, by spectroscopic (e.g., u.v., i.r., visible, Raman, surface enhanced Raman scattering (SERS), mass spectroscopy), photochemical, biochemical, immunochemical, or chemical means. Useful detectable markers include, but are not limited to, fluorescent dyes, chemiluminescent compounds, radioisotopes, electron-dense reagents, enzymes, colored particles, biotin, or dioxigenin. A detectable marker often generates a measurable signal, such as radioactivity, fluorescent light, color, or enzyme activity. Antibodies conjugated to detectable agents may be used for diagnostic or therapeutic purposes. Examples of detectable agents include various enzymes, naturally-occurring spore-associated biomolecules (e.g., dipicolinic acid, calcium dipicolinate), prosthetic groups, fluorescent materials, luminescent materials, bioluminescent materials, radioactive materials, positron emitting metals using various positron emission tomographies, nonradioactive paramagnetic metal ions, Raman labels and SERS labels. The detectable substance can be coupled or conjugated either directly to the antibody or indirectly, through an intermediate such as, for example, a linker known in the art, using techniques known in the art. See, for example, U.S. Pat. No. 4,741,900, describing the conjugation of metal ions to antibodies for diagnostic use. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113}$mIn, $^{115}$mIn), technetium ($^{99}$Tc, $^{99}$mTc), thallium ($^{201}$Ti), gallium ($^{68}$Ga, $^{67}$Ga), palladium ($^{106}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru. Techniques for conjugating such moieties to antibodies are well-known.

Antibodies of the present invention include derivatives of antibodies that are modified or conjugated by the covalent attachment of any type of molecule to the antibody. Such antibody derivatives include, for example, antibodies that have been modified by glycosylation, acetylation, pegylation, phosphorylation, amidation, derivatization by known protecting/blocking groups, proteolytic cleavage, or linkage to a cellular ligand or other protein. Any of numerous chemical modifications can be carried out by known techniques, including, but not limited to, specific chemical cleavage, acetylation, formylation, and metabolic synthesis of tunicamycin. Additionally, the derivatives can contain one or more non-classical amino acids.

Antibodies of the present invention can be assayed for immunospecific binding by the methods described herein and by any suitable method known in the art. The immunoassays that can be used include, but are not limited to, competitive and non-competitive assay systems using techniques such as BIAcore analysis, fluorescence activated cell sorter (FACS) analysis, immunofluorescence, immunocytochemistry, Western blots, radio-immunoassays, enzyme linked immunosorbent assay (ELISA), "sandwich" immunoassays, immunoprecipitation reactions, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see, for example, Ausubel et al., eds, Current Protocols in Molecular Biology, Vol. 1, John Wiley & Sons, Inc., NY (1994)).

Also included in the present invention are compositions including one or more of the antibodies described herein. A composition may also include, for example, buffering agents to help to maintain the pH in an acceptable range or preservatives to retard microbial growth. A composition may include, for example, carriers, excipients, stabilizers, chelators, salts, or antimicrobial agents. Acceptable carriers, excipients, stabilizers, chelators, salts, preservatives, buffering agents, or antimicrobial agents, include, but are not limited to, buffers such as phosphate, citrate, and other organic acids; antioxidants including ascorbic acid and methionine; preservatives, such as sodium azide, octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; polypeptides; proteins, such as serum albumin, gelatin, or non-specific immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zn-protein complexes); and/or non-ionic surfactants such as TWEEN, PLURONICS, or polyethylene glycol (PEG). As used herein, a composition is not a polyclonal antiserum.

The invention also provides a kits or detection systems including one or more antibodies of the present invention. The kit may include one or more containers filled with one or more of the antibodies of the invention. Additionally, the kit may include other reagents such as buffers and solutions needed to practice the invention are also included. Optionally associated with such container(s) can be a notice or printed instructions. A kit can include packaging material. As used herein, the phrase "packaging material" refers to one or more physical structures used to house the contents of the kit. The packaging material is constructed by well known methods, which can provide a sterile, contaminant-free environment.

The present invention includes isolated antibodies. "Isolated," when used to describe the various antibodies disclosed herein, means the antibody that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes.

The antibodies of the present invention may "specifically bind to" or be "specific for" a particular polypeptide or an epitope on a particular polypeptide. Such an antibody is one that binds to that particular polypeptide or epitope on a particular polypeptide without substantially binding to any other polypeptide or polypeptide epitope.

Antibodies of the present invention can be produced by an animal, chemically synthesized, or recombinantly expressed. Antibodies of the present invention can be purified by any method known in the art for purification of an immunoglobulin molecule, for example, by chromatography (including, but not limited to, ion exchange, affinity, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification or detection.

The antibodies of the present invention may be used in a wide variety of diagnostic and therapeutic methods, including, but not limited to, methods for detecting *C. difficile* spores, and polypeptide fragments thereof, and methods for isolating or purifying *C. difficile* spores, or polypeptide fragments thereof.

The antibodies of the present invention may be used in any of the wide variety of immunoassay techniques known in the art to determine the presence or absence of *C. difficile* spores in a sample. As used herein, an immunoassay is a test that identifies the presence of an analyte, such as *C. difficile* spores, in a sample, using the reaction of an antibody to its antigen target. The assay takes advantage of the specific binding of an antibody to its antigen. Also included in the present invention are such methods of detection.

In an immunoassay, a sample is contacted with one or more antibodies and the antibodies are allowed to bind to their antigenic target, if present in the sample. Then, the binding of the one or more antibodies to their antigenic targets is determined, by detecting antibody bound to its antigen target. Such detection may be accomplished, for example, colorimetrically, fluorimetrically, enzymatically, or with radioactive isotopes. Depending on the format of the assay, detectable labels can be bound to an antigen or an antibody. The detectable moiety should be capable of producing, either directly or indirectly, a detectable signal. For example, the detectable moiety may be a radioisotope, such as, for example, $^3$H, $^{14}$C, $^{32}$P, $^{35}$S, or $^{125}$I, a fluorescent or chemiluminescent compound, such as, for example, fluorescein isothiocyanate, rhodamine, or luciferin, or an enzyme, such as, for example, alkaline phosphatase, beta-galactosidase or horseradish peroxidase, a Raman label, or a SERS label. Any method known in the art for conjugating an antibody or antigen to a detectable moiety may be employed. A detectable moiety (also referred to herein as a detectable label) may be conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

An immunoassay of the present invention includes, but is not limited to, competitive and non-competitive assay systems, using techniques such as BIAcore analysis, fluorescence activated cell sorter (FACS) analysis, immunofluorescence, immunocytochemistry, Western blots, radioimmunoassays, enzyme linked immunosorbent assay (ELISA), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see, for example, Ausubel et al., eds, Current Protocols in Molecular Biology, Vol. 1, John Wiley & Sons, Inc., NY (1994)).

An immunoassay of the present invention may be homogeneous or heterogeneous. A heterogeneous immunoassay requires a step to remove unbound antibody or antigen from the sample, usually using a solid phase reagent. Because homogeneous assays do not require this step, they are typically faster and easier to perform. Separation methods include, for example, precipitation (for example, with a second antibody) and removal on a coated tube, coated bead, coated well, magnetic particles or glass particles.

An immunoassay of the present invention may be, for example, a competitive binding assay. In a competitive immunoassay, the antigen in the sample competes with labeled antigen to bind with antibodies. The amount of labeled antigen bound to the antibody site is then measured. In this method, the response will be inversely proportional to the concentration of antigen in the unknown. This is because the greater the response, the less antigen in the sample was available to compete with the labeled antigen. An example of a competitive immunoassay is a radioimmunoassay (RIA).

An immunoassay of the present invention maybe be, for example, an Enzyme-Linked ImmunoSorbent Assay (ELISA). In an ELISA, an unknown amount of antigen is affixed to a surface and then a specific antibody is washed over the surface so that it can bind to the antigen. This antibody is linked to an enzyme, and in the final step a substance is added that the enzyme can convert to some detectable signal and the amount of antigen in the sample can be measured. Performing an ELISA involves at least one antibody with specificity for a particular antigen. The sample with an unknown amount of antigen is immobilized on a solid support (for example, a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody which is linked to an enzyme through bioconjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. ELISAs may utilize chromogenic, luminescent, or fluorigenic substrates.

An immunoassay of the present invention may be a sandwich assay. In sandwich assays, the analyte is a "sandwich" between two antibodies that bind to different antigenic epitopes on the target analyte. One antibody serves as a capture antibody and a second antibody serves as a detection antibody. The capture antibody may be coated to a solid phase, such as a tube or well, and the detection antibody may be detectably labeled.

An immunoassay of the present invention may be, for example, an immunochromatographic lateral flow assay (also referred to herein as a lateral flow assay, a lateral flow test, or immunochromatographic strip test). Lateral flow assays use a simple device to quickly detect the presence (or absence) of a target analyte in sample. These tests are commonly used for medical diagnostics either for home testing, point of care testing, or laboratory use. Often produced in a dipstick format, lateral flow tests are a form of immunoassay in which the test sample, which may be suspended in an aqueous solution, flows through a porous substrate (for example, a nitrocellulose membrane) via capillary or wicking action towards an absorbent pad. After the sample is applied to the substrate, it encounters a colored reagent (for example, gold or latex particles) which mixes with the sample and binds to the analyate, if present in the sample. The mixture transits the substrate encountering lines or zones which have been pretreated to immobilize an antibody capable of binding the analyte. If the analyte is present in the sample, the colored reagent can become bound at the test line or zone. In alternative embodiments, the lateral flow assay can be used to detect specific antibodies present in a sample. In those embodiments, the colored reagent can be antigen-coated particles and the detection lines or zones can be pretreated with the antigen. See, for example U.S. Pat. Nos. 5,753,517, 6,485,982, 6,509,196, 7,189,522, and RE39664, U.S. Patent Application 2006/0275920, and Jeong et al., 2003, *Korean J Biol Sci;* 7:89-92).

Also included in the present invention are detection methods in which one or more antibodies described herein are used to bind *C. difficile* spores, if present in a sample, to a substrate and the presence of spores is then detected and/or quantified by any of a variety of means. The presence of spores may be determined by, for example, microscopy, culturing, enzymatic activity antibody binding (as, for example, in an ELISA assay), calcium molecular fluorescence or luminescence, or lanthanide metal mediated luminescence. Dipicolinic acid in a 1:1 complex with calcium ions is present in high concentrations in bacterial spores and has not been observed in any other life forms. A lanthanide metal, such as for example, terbium or europium, will combine with dipicolinic acid (DPA) present in any bacterial spores in a sample to produce a lanthanate chelate, such as, for example, terbium or europium dipicolinate. Such lanthanate chelates have distinctive absorbance and emission spectra that can be detected using photoluminescence testing. Lanthanide metal mediated luminescence may also be utilized as a detection signal in any of the various immunoassay methods described herein, for example, in a lateral flow assay. Upon spore germination, Ca-DPA is released and calcium can be detected by a number of means. Fluorimetric detection of calcium by the use of molecular fluorescence or luminescence for sensing offers high sensitivity. Calcium indicator dyes can be categorized into two groups; the first are the dyes that increase their fluorescence in the presence of calcium, while the second group are dyes that have different excitation and/or emission wavelengths in the presence of calcium than they have in its absence. The calcium indicator dyes, calcium green-1, calcium green-2, and Fluo-4 are representative of the dyes that increase their fluorescence in the presence of calcium ion ($Ca^{2+}$) without changing wavelengths. Fura-2 and Indo-1 are ratiometric $Ca^{2+}$ indicators that are generally considered interchangeable in most experiments. Fura-2, upon binding $Ca^{2+}$, exhibits a shift in its absorption or excitation peak from 338 nm to 366 nm. Indo-1 on the other hand has a shift in the emission from 485 nm to 405 nm in the presence of calcium. Calcium can also be detected using calcium-activated photoproteins, such as aequorin and obelin. Since there is no need for excitation from external irradiation for the emission of bioluminescence, the signal produced has virtually no background. This allows for detection limits at extremely low levels, making these photoproteins attractive labels for analytical applications. Calcium mediated signaling may also be utilized as a detection signal in any of the various immunoassay methods described herein, for example, in a lateral flow assay. Such methods, and the other methods described herein, also allow for the quantification of spores present in a sample. See, for example, U.S. Pat. Nos. 5,876,960; 6,498,041; 6,815,178; and 7,306,942, U.S. Patent Application Serial Nos. 2003/0138876; 2004/0014154; and 2005/0136508; and Ponce, 2003, *NASA Tech Brief,* 27 (3): pp. i-ii, 1-3.

With the detection methods of the present invention, one or more antibodies may be used, including one or more of the antibodies described herein that bind to a *C. difficile* spore. Further, one or more additional antibodies of known specificity may be used, for example, one or more antibodies that bind to *C. difficile* vegetative cells, that bind to vegetative cells of a different bacterial species, such as, for example, *C. clostridium* or *B. subtilis,* or that bind to spores of a different bacterial species, such as, for example, spores of *C. clostridium* or *B. subtilis,* may be used.

Samples may be obtained from a wide variety of source and include, but are not limited to, environmental or food samples and medical or veterinary samples. Examples of environmental samples, include, but are not limited to, water samples, soil samples, plant samples, and air samples. Examples of foods include, but are not limited to: meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, and animal feed. Medical or veterinary samples include, but are not limited to: clinical samples, cell lysates, whole blood or a portion thereof (e.g., serum), other bodily fluids or secretions (e.g., saliva, sputum, sweat, sebum, urine, cerebrospinal fluid), feces, cells, tissues, organs, biopsies, and different types of swabs.

A sample may be obtained from a fomite. The term "fomite" is generally used to refer to an inanimate object or substrate capable of carrying infectious organisms and/or transferring them. A fomite serves to transmit an infectious agent, such as *C. difficile*, from person to person. Fomites can include, but are not limited to, cloths, mop heads, towels, sponges, wipes, eating utensils, coins, paper money, cell phones, clothing (including shoes), doorknobs, feminine products, diapers, etc., portions thereof, and combinations thereof. There are many examples of fomites with respect to medicine; tools such as laryngoscopes that are not properly disinfected between uses, dirty towels, eating utensils, and surfaces such as floors, walls, and tables may all serve to spread disease. The surface of interest can include at least a portion of a variety of surfaces, including, but not limited to, walls (including doors), floors, ceilings, drains, refrigeration systems, ducts (e.g., airducts), vents, toilet seats, handles, doorknobs, handrails, bedrails (e.g., in a hospital), countertops, tabletops, eating surfaces (e.g., trays, dishes, etc.), working surfaces, equipment surfaces, clothing, etc., and combinations thereof.

Samples may be liquid, solid, or semi-solid. Samples may be swabs of solid surfaces. Samples may be used directly in the detection methods of the present invention, without preparation or dilution. For example, liquid samples, may be assayed directly. Samples may be diluted or suspended in solution, which may include, but is not limited to a buffered solution or a bacterial culture medium. A sample that is a solid or semi-solid may be suspending in a liquid by mincing, mixing or macerating the solid in the liquid. A sample may by further concentrated or enriched.

The immunoassays of the present invention may include various appropriate control samples. For example, negative control samples containing no bacterial spores, cells or toxin, or positive control samples containing bacterial cells, spores or toxin may be assayed. An immunoassay of the present invention may take as little as a few minutes to develop and may require little or no sample or reagent preparation. An immunoassay of the present invention may be performed in a qualitative or quantitative format. Qualitative results provide a simple positive or negative result for a sample. The cutoff between positive and negative is determined by the analyst and may be statistical. Two or three times the standard deviation is often used to distinguish positive and negative samples. In quantitative formats, results may be interpolated into a standard curve, which is typically a serial dilution of the target.

The present invention is illustrated by the following examples. It is to be understood that the particular examples, materials, amounts, and procedures are to be interpreted broadly in accordance with the scope and spirit of the invention as set forth herein.

EXAMPLES

Example 1

Generation of *C. difficile* Spores

One tube of Brain Heart Infusion Broth (BHI) was inoculated with *C. difficile* (ATCC® No. 700792, American Type Culture Collection, Manassas, Va.) and incubated for twenty-four hours at 35-37° C. under anaerobic conditions. Following incubation, one milliliter (ml) aliquots of the broth culture were transferred to a minimum of four tubes containing BHI broth and then incubated for twelve days at 35-37° C. under anaerobic conditions. The broth cultures were centrifuged at 10,000 rotations per minute (rpm) for 10 minutes (min) and the cell pellet was resuspended in 10 ml of absolute ethanol for one hour at room temperature to kill vegetative cells. After one hour the suspension was centrifuged at 10,000 RPM for 10 minutes and the cell pellet was washed at least twice with sterile Butterfield's buffer. The pellet was resuspended in sterile Butterfield's Buffer and spore number per milliliter was determined by plating serial dilution on anaerobic blood agar. Resuspended spores were used in the following examples as both an immunogen in the generation of polyclonal antibodies to inactivated spores and as an antigenic target in ELISA assays to determine the binding specificity of anti-spore antibodies.

Example 2

Generation of Polyclonal Antibody to Inactivated *C. difficile* Spores

*C. difficile* spores, at a concentration of about $10^6$ spores per ml, were treated with 5% formalin for 10 minutes to inactivate the spores. The inactivated spores were washed twice with sterile Butterfield's buffer and then resuspended in sterile Butterfield's buffer. A polyclonal antibody was raised against the inactivated spores in rabbits using standard protocols (Antagene, Inc, Mountain View, Calif.). Briefly, New Zealand White rabbits (two individual rabbits) were immunized with $1 \times 10^6$/ml equivalent of inactivated spores per immunization. The immunogen was diluted to 1 ml with sterile saline and combined with 1 ml of the appropriate adjuvant. The antigen and adjuvant were mixed to form a stable emulsion which was injected subcutaneously. Rabbits were immunized on day one with antigen in Complete Freund's Adjuvant (CFA), followed by immunizations on days 20, 40, and 60 with antigen in Incomplete Freund's Adjuvant (IFA) for all subsequent injections.

Ten days after the last immunization, the blood was collected from the rabbit and allowed to clot and retract at 37° C. overnight. The clotted blood was then refrigerated for 24 hours and the serum was decanted and clarified by centrifugation at 2500 rpm for 20 minutes. The preimmune and immune serums were tested against inactivated spores by ELISA. For the ELISA protocol, inactivated spores of *C. difficile* were diluted to $10^5$ spores per milliliter (ml) in coating buffer (0.1 M bicarbonate buffer 1.59 grams (g) $Na_2CO_3$ and 2.93 g $NaHCO_3$ per liter of sterile distilled water, pH 9.6). 100 microliter (µl) of the spore solution was added to wells of an ELISA plate (ELISA Enhanced Surface plate, BD Falcon, Franklin Lakes, N.J.). To the control wells, 100 µl of coating buffer was added. The plates were wrapped with PARAFILM and incubated at 4° C. for 15 to 16 hours. The plates were emptied and washed three times with wash buffer (Phosphate buffered saline with 0.05% Tween 20). The plates were blocked with 100 µl of blocking buffer (1% BSA and 0.05% Tween-20 in PBS) for two hours with shaking at room temperature (RT). The plates were emptied, washed three times with wash buffer and incubated with 100 µl primary antibody in blocking buffer for one to two hours with shaking at RT. The plates were emptied, washed three times with wash buffer and incubated with 100 µl of secondary antibody with HRP label (goat anti-rabbit HRP conjugate; 1:10,000 dilution, Pierce, Rockford, Ill.) for one hour with shaking at RT. The plates were emptied and washed four times with wash buffer. 50 µl of the substrate solution (1-step Ultra TMB, Pierce, Rockford, Ill.) was added to each of the wells and incubated with shaking at RT for 15 to 30 minutes. The color was stopped by adding 50 µl of stop solution (1.5 M phosphoric acid) and absorbance of each plate was read in a SpectraMax plus 384 (Molecular Devices, Sunnyvale, Calif.) at 450 nm. The absorbances were compared to determine fold-enhancement of signal for target. The immunized serum showed a good response to inactivated spores, approximately 13 to 15 fold that obtained with the preimmune serum (Table 1).

TABLE 1

Characterization of antiserum generated against inactivated *C. difficile* spores
Absorbance at 450 nm*

| Antibody dilution | Rabbit #1 | | Rabbit #2 | |
|---|---|---|---|---|
| | Preimmune serum | Antisera | Preimmune serum | Antisera |
| 1:1000 | 0.07 | 1.73 | 0.04 | 1.92 |
| 1:10,000 | 0.06 | 1.22 | 0.07 | 1.27 |
| 1:100,000 | 0.06 | 0.78 | 0.06 | 0.82 |

*Average no antigen control readings with preimmune and antiserum were 0.12 at 450 nm.

The antibody was purified by ammonium sulfate precipitation followed by protein A column chromatography. Briefly, antisera were precipitated by drop-wise addition of ice-cold saturated ammonium sulfate to a final ratio of 1:1 (50% saturated ammonium sulfate). This procedure was done in an ice-cold beaker, with constant stirring. The supernatant was transferred to a 50-mL centrifuge tube and placed on a reciprocating mixer overnight at 4° C. The suspension was centrifuged at 10,000×g for 30 minutes at 2° C. The supernatant was removed and the pellet was resuspended in an equal volume of deionized water. The resuspended protein was dialyzed (12,000-14,000 MW cut-off dialysis tubing) against two liters (L) of PBS. The dialysis buffer was removed and replaced after about two hours and again after about 24 hours. After about 48 hours of dialysis, the protein dialysate was removed and filtered with a 0.22 µm filter.

The IgG fraction was recovered from the filtrate by chromatography, using a Protein A affinity column from BioRad (Hercules, Calif.) according to the manufacturer's instructions. Briefly, a Shimadzu HPLC system (Model SCL-10AVP, Shimadzu Corporation, Shimadzu Scientific Instruments, Inc., Columbia, Md.) was used for all preparative chromatography runs. The solvents used for the binding and elution of the antibodies are listed below were Binding Buffer A (Phosphate Buffered Saline, pH 7.3) and Elution Buffer B (20 mM Sodium Acetate, 0.5 M NaCl, pH 3.5). All buffers were prepared with deionized water using a MILLI Q filtration system (Millipore Corp., Billerica, Mass.) and were filtered through a 0.22-µm (pore size) membrane filter. The column was pre-equilibrated with binding buffer A prior to sample injection. The antisera samples were manually injected into the column via a sample injection loop at T=0 minutes. After sample injection, the solvents were run through the column as follows: Binding Buffer B starting at T=0 at a flow rate of 0.6 ml/min; Elution Buffer B starting at T=20 minutes at a flow rate of 1.0 ml/min; and Binding Buffer B starting at T=60 minutes at a flow rate of 1.0 ml/min. Fractions of the column eluate from each of the mobile phase solvents were collected. Purified anti-*C. difficile* antibody protein eluted at around 51 minutes. Each run was 70 minutes long after which the second peak was put into dialysis for three changes of buffer to change the pH. The fractions were then filtered and pooled and the OD measured. At 20 minutes the buffer was changed to elution buffer. The purified antibody was dialysed against PBS with three changes of buffer at 4° C. The dialysed antibody was concentrated using Centricon filters (10,000 molecular weight cut off; Millipore Corporation, Billerica, Mass.)

The purified antibody was tested by ELISA against *C. difficile, C. sporogenes* (ATCC 3584) and *B. subtilis* (ATCC 19659) spores. The *C. sporogenes* and *B. subtilis* spores were obtained from Presque Isle Cultures (Erie, Pa.). Spores were diluted in coating buffer. Various levels of spores ($10^3$ to $10^5$ per ml) of *B. subtilis, C. sporogenes* and *C. difficile* were coated and tested with the antibody in ELISA assays performed as described above. The antigen antibody interaction was detected using anti-rabbit HRP antibody (Pierce, Rockford, Ill.) and the spore antibody showed good reaction with *C. difficile* spores, about 20-fold response over background at $10^5$ spores per ml, and showed a weak, approximately 2-fold with *C. sporogenes*, and no reaction over background with *B. subtilis* spores (see Table 2). The data presented in Table 2 are the average of readings from three wells from one of the experiment and are representative of at least three separate experiments.

TABLE 2

Characterization of purified rabbit *C. difficile* spore antibody
Absorbance at 450 nm

| Spores/ml | *B. subtilis* | *C. sporogenes* | *C. difficile* |
|---|---|---|---|
| 1.00E+03 | 0.21 | 0.24 | 0.17 |
| 1.00E+04 | 0.16 | 0.25 | 0.8 |
| 1.00E+05 | 0.16 | 0.41 | 4.13 |
| No antigen control | 0.17 | 0.17 | 0.17 |

Example 3

Selection of *C. difficile* Spore-Specific Proteins for Generation of Antibodies The complete genome sequence of *C. difficile* strain 630 has been determined and is available on the GenBank® sequence database maintained by the National Center for Biotechnology Information (NCBI), National Library of Medicine (NLM), National Institutes of Health (NIH). See also, Sebaihia et al., 2006, *Nat. Genet;* 38 (7):779-786). A thorough search of all the GenBank® entries for *C. difficile* was made and two spore specific proteins were picked for antibody production. One of the proteins selected was hypothetical protein CD1021 (YP_001087502), which demonstrates a conserved domain (amino acid residues 90 to 393) to the spore coat assembly protein H (cotH). The other protein selected was cell surface protein (putative N-acetylmuramoyl-L-alanine amidase, YP_001087517) which has conserved domains CW_binding_2 (putative cell wall binding repeat 2; 174 to 265, 275 to 368, 381 to 461) and Amidase_3 (N-acetylmuramoyl-L-alanine amidase, 493 to 673). The analysis was performed using conserved domain search tools available from the NCBI.

Hypothetical Protein CD1021 of C. difficile 630 (GenBank Accession No. YP_001087502) has the following amino acid sequence:

```
                                              (SEQ ID NO: 1)
    MKDKKFTLLI SIMIVFLCAV VGVYSTSSNK SVDLYSDVYI

EKYFNRDKVM EVNIEIDESD LKDMNENAIK EEFKVAKVTV

DGDTYGNVGI RTKGNSSLIS VANSDSDRYS YKINFDKYNT

SQSMEGLTQL NLNNCYSDPS YMREFLTYSI CEEMGLATPE

FAYAKVSING EYHGLYLAVE GLKESYLENN FGNVTGDLYK

SDEGSSLQYK GDDPESYSNL IVESDKKTAD WSKITKLLKS

LDTGEDIEKY LDVDSVLKNI AINTALLNLD SYQGSFAHNY

YLYEQDGVFS MLPWDFNMSF GGFSGFGGGS QSIAIDEPTT

GNLEDRPLIS SLLKNETYKT KYHKYLEEIV TKYLDSDYLE

NMTTKLHDMI ASYVKEDPTA FYTYEEFEKN ITSSIEDSSD

NKGFGNKGFD NNNSNNSDSN NNSNSENKRS GNQSDEKEVN

AELTSSVVKA NTDNETKNKT TNDSESKNNT DKDKSGNDNN

QKLEGPMGKG GKSIPGVLEV AEDMSKTIKS QLSGETSSTK

QNSGDESSSG IKGSEKFDED MSGMPEPPEG MDGKMPPGMG

NMDKGDMNGK NGNMNMDRNQ DNPREAGGFG NRGGGSVSKT

TTYFKLILGG ASMIIMSIML VGVSRVKRRR FIKSK
```

See also, Sebaihia et al., 2006, *Nat. Genet;* 38 (7):779-786.

The putative N-acetylmuramoyl-L-alanine amidase cell surface protein of *C. difficile* 630 (GenBank Accession No. YP_001087517) has the following amino acid sequence:

```
                                              (SEQ ID NO: 5)
    MLSKEINMRR NTKLLTTGIL SMAIVAPTMA FATESNAMEN

NADLNINLEK KSIVLGSKSK VSVKFKEKPD ADSIKLKYKC

YDMPLNTTLN YNQSTGAYEG IINYNKDPEY LNVWELQGIT

INSKTNPKTL NRQDLEKMGL NLKDYNVTQE CIIEDITSRK

DVNKYLRKTS SPITELTGSD RYETAVKISK EGWKNGSDKV

VIINGDVSID GIISTPLATT YNAPILLVEK NNVPNSVKSE

LKRLNPKDII IIGDENAISK TTANQIKSTV NASQTRLNGS

NRYETSLLIA KEIDKNHDVE KVYITNANGG EVDALTIAAK

AGQDKQPIIL TDKDSITDNT YKWLKSEDLQ NAYFIGGPQM

ISTNVINKVN GITKDSVTNN RVYGADRHET NANVIKKFYT

DDELEAVLVA KSDVLVDALA AGPLAANLKS PILITPKTYV

SAYHKDNLEA KSANKVYKIG GGLTSKVMSS IASSLSKHNT

TPTEPGNSGG KTVMIDPGHG GSAPGNSSGG MIEKDYNLNT

SLATTEYLRS KGFNVIMTRD TDKTLSLGNR TALSNSLKPD

LFTSIHYNGS TNKQGHGVEV FYKLKDKNGG TTKTVATNIL

NRILEKFKLT NRGIKTRVLP SDSTKDYLYV LRSNDMPAVL

VECAFLDNEN DMSLINSSAK VKEMGTQIGK GIEDSLK.
```

See also, Sebaihia et al., 2006, *Nat. Genet;* 38 (7):779-786.

Example 4

GAT Polyclonal Antibody Against Hypothetical Protein CD1021

A polyclonal antibody against hypothetical protein CD1021 was generated using Strategic Diagnostics Inc.'s (SDI) (Newark, Del.) proprietary Genomic Antibody Technology™ (GAT). A unique amino acid sequence from the protein was identified and this sequence information was placed in SDI's proprietary plasmid vector. The vector was introduced into a mouse. With this technology, cells of the host animal take up the plasmid. In these cells, the immunogen is synthesized and secreted by the host cells and immediately recognized by the immune system leading to production of polyclonal antibodies against the expressed protein sequence. Both polyclonal and monoclonal antibodies can be developed using GAT. The protein immunogen is produced in the host animal using natural protein synthesis machinery. Since the immunogen is not synthesized and purified in a laboratory, it does not have the opportunity to denature or degrade. A native immunogen is presented immediately to the immune system, resulting in a mature antibody response.

The protein sequence of hypothetical protein CD1021 used for polyclonal antibody generation was residues 505 to 604 and had the amino acid sequence:

```
                                              (SEQ ID NO: 2)
    SKTIKSQLSG ETSSTKQNSG DESSSGIKGS EKFDEDMSGM

PEPPEGMDGK MPPGMGNMDK GDMNGKNGNM NMDRNQDNPR

EAGGFGNRGG GSVSKTTTYF.
```

The sera from two immunized mice was pooled and tested against the immunogen by Western blot to determine specificity of the antibody. Later, the antibody was purified by ammonium sulfate precipitation followed by protein A column chromatography, as described in Example 2.

Initially, various levels of spores ($10^3$ to $10^5$ per ml) of *B. subtilis, C. sporogenes* and *C. difficile* were coated and tested with the antibody. The antigen-antibody interaction was detected using anti-mouse HRP antibody (Pierce, Rockford, Ill.). The mouse antibody against the hypothetical protein CD1021 (SEQ ID NO:2) showed about a 10-fold increased response over background at $10^5$ spores per ml, and showed a weak response (about 2-fold) with *C. sporogenes* spores, and no reaction over background with *B. subtilis* spores (see Table 3). The data presented in Table 3 are the average of readings of three wells and are representative of two separate experiments.

TABLE 3

Characterization of C. difficile hypothetical protein CD1021 mouse antibody
Absorbance at 450 nm

| Spores/ml | B. subtilis | C. sporogenes | C. difficile |
|---|---|---|---|
| 1.00E+03 | 0.13 | 0.13 | 0.2 |
| 1.00E+04 | 0.15 | 0.17 | 0.2 |
| 1.00E+05 | 0.15 | 0.32 | 1.61 |
| No antigen control | 0.14 | 0.14 | 0.14 |

The antibody was further tested using sandwich ELISA. Plates were coated with the polyclonal CD1021 antibody followed by binding of spores (*B. subtilis, C. sporogenes* and *C. difficile*). The antibody antigen interaction was detected using the anti-*C. difficile* inactivated spore antibody from example 2, above, as the second antibody, followed by anti-rabbit HRP antibody (BD Pharmingen). The spores of *B. subtilis, C. sporogenes*, and *C. difficile* were used at various levels and antibody is specific for detection of *C. difficile* spores. The results are shown in Table 4, below.

In the sandwich ELISA protocol, the purified mouse CD1021 antibody was diluted in antigen coating buffer at 1 µg/ml concentration. 100 µl of the of the antibody solution was added to wells of an ELISA plate (ELISA Enhanced Surface plate, BD Falcon, Franklin Lakes, N.J.). The plates were wrapped with Parafilm and incubated at 4° C. for 15 to 16 hours. The plates were emptied and washed four times with wash buffer. The plates were blocked with 100 µl of blocking buffer for 2 hours with shaking at room temperature (RT). The plates were emptied, washed four times with wash buffer and spore solutions of *C. difficile, C. sporogenes,* and *B. subtilis* (100 µl of $10^3$, $10^4$, and $10^5$ spores per ml) in blocking buffer were added. For control wells, 100 µl of blocking buffer was added. After incubation at RT for two hours, the plates were emptied, washed four times with wash buffer and incubated with 100 µl of secondary antibody (anti-rabbit *C. difficile* spore antibody, descried in Example 2) in blocking buffer for one hour with shaking at RT. The plates were emptied, washed four times with wash buffer and incubated with 100 µl of secondary antibody with HRP label (goat anti-rabbit HRP conjugate; 1:10,000 dilution, BD Pharmingen) for one hour with shaking at RT. The plates were emptied and washed three times with wash buffer. 50 µl of the substrate solution (1-step Ultra TMB, Pierce) was added to each of the wells and incubated with shaking at RT for 15 to 30 minutes. The color was stopped by adding 50 µl of stop solution (1.5 M phosphoric acid) and absorbance of each plate was read at 450 nm. The absorbances were compared against control to determine fold-enhancement of signal for target (see Table 4). The data presented in Table 4 are the average of readings of three wells and are representative of two separate experiments.

TABLE 4

Characterization of C. difficile hypothetical protein CD1021 mouse antibody by Sandwich ELISA with spore antibody
Fold-change over control*

| Spores/ml | B. subtilis | C. sporogenes | C. difficile |
|---|---|---|---|
| 1.00E+03 | 1.1 | 1.03 | 1.22 |
| 1.00E+04 | 1.12 | 1.08 | 1.4 |
| 1.00E+05 | 1.14 | 1.04 | 2.35 |

*No antigen control readings were 1.05 at 450 nm

Example 5

Polyclonal Antibodies Against Hypothetical Protein CD1021 Peptides

Two unique amino acid sequences were identified from the hypothetical protein CD1021. A search in both protein and DNA databases showed that both sequences are specific to *C. difficile* and have no homology with other bacteria such as *Bacillus*. These two sequences are:

```
Peptide 1   EGSSLQYKGDDPESY      (SEQ ID NO: 3)
            (residues 203 to 217 of CD1021)

Peptide 2   LKNETYKTKYHKYLE      (SEQ ID NO:4)
            (residues 333 to 347 of CD1021).
```

The peptides were synthesized with a free cysteine at the N-terminal end and conjugated to keyhole limpet hemocyanin (KLH) to elicit high titer antibodies. Each of the two KLH conjugated peptides was used separately to immunize two individual rabbits according to standard protocols with antigen by Epitomics (Burlingame, Calif.). Briefly, a primary injection of KLH-conjugated peptide (0.5 mg/ml) with 1 ml of CFA was followed by four boosts of KLH-conjugated peptide (0.25 mg/ml) with 1 ml of IFA.

Blood was collected after each immunization and sera was tested by ELISA using the respective peptides. Bleed three and four showed a good response to the peptides, approximately 5 to 7-fold response over the preimmune serum (Table 5).

TABLE 5

Characterization of C. difficile CD1021 peptide serum (bleed 3)
Absorbance at 450 nm*

| | Peptide 1 | | | | Peptide 2 | | | |
|---|---|---|---|---|---|---|---|---|
| | Rabbit #1 | | Rabbit #2 | | Rabbit #1 | | Rabbit #2 | |
| Antibody dilution | Preimmune serum | Antisera | Preimmune serum | Antisera | Preimmune serum | Antisera | Preimmune serum | Antisera |
| 1:1000 | 0.18 | 1.72 | 0.20 | 1.62 | 0.200 | 1.82 | 0.20 | 1.81 |
| 1:10,000 | 0.15 | 1.21 | 0.15 | 1.12 | 0.120 | 1.18 | 0.14 | 1.05 |
| 1:100,000 | 0.10 | 0.68 | 0.08 | 0.72 | 0.070 | 0.64 | 0.08 | 0.74 |

*Average no antigen control readings with preimmune and antiserum were 0.15 at 450 nm.

The serum from bleed three and four were purified by ammonium sulfate precipitation followed by protein A column chromatography, as described in Example 2. The purified antibody was tested by ELISA for binding to plate bound peptides.

The peptides were diluted in antigen coating buffer at 1 µg/ml concentration. 100 µl of the of the peptide solution was added to wells of an ELISA plate (ELISA Enhanced Surface plate, BD Falcon, Franklin Lakes, N.J.). To the control wells 100 µl of coating buffer was added. The plates were wrapped with Parafilm and incubated at 4° C. for 15 to 16 hours. The plates were emptied and washed three times with wash buffer. The plates were blocked 100 µl of blocking buffer for two hours with shaking at room temperature (RT). The plates were emptied, washed three times with wash buffer and incubated with 100 µl primary antibody in blocking buffer for one to two hours with shaking at RT. The plates were emptied, washed three times with wash buffer and incubated with 100 µl of secondary antibody with HRP label (1;10,000 dilution) for 1 hour with shaking at RT. The plates were emptied and washed three times with wash buffer. 50 µl of the substrate solution (1-step Ultra TMB, Pierce) was added to each of the wells and incubated with shaking at RT for 15 to 30 minutes. The color was stopped by adding 50 µl of stop solution (1.5 M phosphoric acid) and absorbance of each plate was read at 450 nm. The absorbances were compared against control to determine fold-enhancement of signal for target.

Various levels of spores ($10^3$ to $10^5$ per ml) of *B. subtilis, C. sporogenes* and *C. difficile* were coated and tested with the antibody. The antigen antibody interaction was detected using anti-rabbit HRP antibody (Pierce, Rockford, Ill.) and the antibodies were specific for detection of *C. difficile* spores, demonstrating a 6 to 10-fold response over background with *C. difficile* spores (see Table 6). The data presented in Table 6 are the average of readings of three wells and are representative of at least three separate experiments.

immunogen was expressed in vivo in mouse, as described in Example 4. The expressed immunogen is recognized by the host immune system leading to production of a polyclonal antibody against the expressed protein. The protein sequence of cell surface protein (putative N-acetylmuramoyl-L-alanine amidase) used for antibody generation was residues 294 to 393, having the amino acid sequence of DKNHDVEKVYIT-NANGGEV DALTIAAKAG QDKQPIILTD KDSITD-NYKW LKSEDLQNAY FIGGPQMIST NVINKVNGIT KDSVTNNRVY GADRHETNAN (SEQ ID NO:6).

The sera was pooled from immunized animals and tested against the immunogen by Western blot to determine specificity of the antibody. Later, the antibody was purified by ammonium sulfate precipitation followed by protein A column chromatography.

Initially, various levels of ungerminated spores ($10^3$ to $10^5$ per ml) of *B. subtilis, C. sporogenes* and *C. difficile* were coated and tested with the antibody. The antigen antibody interaction was detected using anti-mouse HRP antibody (Pierce, Rockford, Ill.). The antibody against cell surface protein (putative N-acetylmuramoyl-L-alanine amidase) did not show any reaction with *C. difficile* or other spores.

The spores of *B. subtilis, C. sporogenes* and *C. difficile* were germinated using various germinant solutions. The germinated spores ($10^3$ to $10^5$ per ml) were coated and tested with the antibody. The antigen antibody interaction was detected using anti-mouse HRP antibody (Pierce, Rockford, Ill.). The antibody was able to detect germinated *C. difficile* spores, demonstrating about a 6-fold response over background, but not germinated *B. subtilis* or *C. sporogenes* spores (see Table 7). The data presented in Table 7 are the average of readings of three wells and are representative of two separate experiments.

Germination of spores has been well studied with *B. subtilis* spores which can be induced to germinate by specific germinants, including L-alanine and a combination of aspar-

TABLE 6

Characterization of rabbit antibodies to peptide sequences of *C. difficile* hypothetical protein CD1021
Absorbance at 450 nm

| | Peptide 1 Ab | | | Peptide 2 Ab | | |
|---|---|---|---|---|---|---|
| Spores/ml | *B. subtilis* | *C. sporogenes* | *C. difficile* | *B. subtilis* | *C. sporogenes* | *C. difficile* |
| 1.00E+03 | 0.15 | 0.14 | 0.2 | 0.14 | 0.14 | 0.21 |
| 1.00E+04 | 0.16 | 0.17 | 0.21 | 0.17 | 0.17 | 0.48 |
| 1.00E+05 | 0.16 | 0.29 | 1.53 | 0.16 | 0.27 | 0.95 |
| No Antigen control | 0.22 | 0.22 | 0.22 | 0.2 | 0.2 | 0.2 |

Example 6

GAT Polyclonal Antibody Against a Putative N-Acetylmuramoyl-L-Alanine Amidase Cell Surface Protein A polyclonal antibody against a cell surface protein that is a putative N-acetylmuramoyl-L-alanine amidase protein was generated using Strategic Diagnostics Inc.'s (Newark, Del.) proprietary Genomic Antibody Technology™ (GAT). A unique sequence from the protein was identified and the agine glucose, fructose and potassium ions ("AGFK") (Moir and Smith, 1990, *Ann Rev Microbiol;* 44:531-553). Initial attempts to germinate *C. difficile* spores were using various germinants (combination of AGFK with alanine and Inosine), but spore germination was not efficient. The *C. difficile* spores germinate in a nutrient medium with addition of 1% sodium taurocholate (Sorg and Sonenshein, 2008, *J Bacteriol* (published online ahead of print on 1 Feb. 2008) doi:10.1128/JB.01765-07), the spores were germinated in Brain Brain-Heart Infusion broth supplemented with yeast extract (5 mg/ml), L-cysteine (0.1%) and 1% sodium taurocholate. The germination of spores was followed by measuring the OD600 of spore cultures (OD600 decreases upon germination) and by phase contrast microscopy. Spores of *C. sporogenes* and *B. subtilis* were germinated following previously as described before (Broussolle et. al., 2002, *Anaerobe;* 8:89-100; Moir and Smith, 1990, *Ann Rev Microbiol;* 44, 531-553).

TABLE 7

Characterization of *C. difficile* putative amidase mouse antibody
Absorbance at 450 nm

| Spores/ml | B. subtilis | | C. sporogenes | | C. difficile | |
| --- | --- | --- | --- | --- | --- | --- |
| | Ungerminated | Germinated | Ungerminated | Germinated | Ungerminated | Germinated |
| 1.00E+03 | 0.13 | 0.17 | 0.14 | 0.16 | 0.2 | 0.18 |
| 1.00E+04 | 0.12 | 0.2 | 0.13 | 0.22 | 0.2 | 0.39 |
| 1.00E+05 | 0.15 | 0.22 | 0.15 | 0.27 | 0.2 | 0.82 |
| No antigen control | 0.13 | 0.13 | 0.13 | 0.13 | 0.13 | 0.13 |

Example 7

Polyclonal Antibody Against Cell Surface Protein (Putative N-Acetylmuramoyl-L-Alanine Amidase) Peptides Two unique sequences were identified from the protein sequence of *C. difficile* N-acetylmuramoyl-L-alanine amidase and upon BLAST search in both protein and DNA database the sequences are specific to *C. difficile* and have no homology with other bacteria such as *Bacillus*.

```
                                              (SEQ ID NO: 7)
Peptide 1 YKLKDKNGGTTKTVA (amino acid residues 582
to 596)

(SEQ ID NO: 8)
Peptide 2 KFKEKPDADSIKLKY (amino acid residues 64
to 78)
```

The peptides were synthesized with a free cysteine at the N-terminal end and conjugated to KLH to elicit high titer antibodies. Both KLH conjugated peptides were combined and used together to immunize two individual rabbits according to standard protocols by Antagene (Mountain View, Calif.). Ten days after the last immunization, the blood was collected from the rabbit and allowed to clot and retract at 37° C. overnight. The clotted blood was then refrigerated for 24 hours and the serum was decanted and clarified by centrifugation at 2500 rpm for 20 minutes. Initial ELISA was done with preimmune and immunized serum against the peptides. Immunized serum against the peptides showed good response to peptides, demonstrating about a 7 to 10-fold response over the preimmune serum (Table 8).

TABLE 8

Characterization of *C. difficile* putative amidase peptide serum
Absorbance at 450 nm*

| Antibody dilution | Rabbit #1 | | Rabbit #2 | |
| --- | --- | --- | --- | --- |
| | Preimmune serum | Antisera | Preimmune serum | Antisera |
| 1:1000 | 0.25 | 1.83 | 0.22 | 1.70 |
| 1:10,000 | 0.20 | 1.55 | 0.15 | 1.81 |
| 1:100,000 | 0.12 | 0.91 | 0.10 | 0.98 |

*Average no antigen control readings with preimmune and antiserum were 0.20 at 450 nm.

The antibody was purified by ammonium sulfate precipitation followed by protein A column chromatography, as described in Example 2. The purified antibody was tested by ELISA. Initially, various levels of ungerminated spores ($10^3$ to $10^5$ per ml) of *B. subtilis, C. sporogenes* and *C. difficile* were coated and tested with the antibody. The antigen antibody interaction was detected using anti-rabbit HRP antibody (Pierce, Rockford, Ill.). The antibody against cell surface protein (putative N-acetylmuramoyl-L-alanine amidase) did not show any reaction with *C. difficile* or other spores. The spores of *B. subtilis, C. sporogenes* and *C. difficile* were germinated using various germinant solutions. The germinated spores ($10^3$ to $10^5$ per ml) were coated and tested with the antibody. The antigen antibody interaction was detected using anti-rabbit HRP antibody (Pierce, Rockford, Ill.). The antibody was able to detect germinated *C. difficile* spores, demonstrating about a 6-fold response over background, but not *B. subtilis* or *C. sporogenes* germinated spores (see Table 9). The data presented in Table 9 are the average of readings of three wells and are representative of two separate experiments.

TABLE 9

Characterization of *C. difficile* putative amidase rabbit antibody
Absorbance at 450 nm

| Spores/ml | B. subtilis Ungerminated | B. subtilis Germinated | C. sporogenes Ungerminated | C. sporogenes Germinated | C. difficile Ungerminated | C. difficile Germinated |
|---|---|---|---|---|---|---|
| 1.00E+03 | 0.13 | 0.18 | 0.14 | 0.17 | 0.2 | 0.18 |
| 1.00E+04 | 0.13 | 0.19 | 0.12 | 0.21 | 0.18 | 0.44 |
| 1.00E+05 | 0.14 | 0.22 | 0.15 | 0.26 | 0.19 | 0.93 |
| No antigen control | 0.13 | 0.13 | 0.13 | 0.13 | 0.13 | 0.13 |

Example 8

Polyclonal Antibody Against *C. difficile* Common Antigen for Detection of *C. difficile* Spores The commercially available rabbit *C. difficile* common antigen (glutamate dehydrogenase) antibody (Meridian Life Science, Saco, Me.) reacts with both toxigenic and nontoxigenic strains and is used to detect vegetative cells of *C. difficile*. In this example, the commercially available rabbit *C. difficile* common antigen antibody was tested for detection of *C. difficile* spores by ELISA. The antibody was purified by ammonium sulfate precipitation followed by protein A column chromatography. Various levels of spores ($10^3$ to $10^5$ per ml) of *B. subtilis*, *C. sporogenes* and *C. difficile* were coated to a plate and tested with the antibody. The antigen antibody interaction was detected using anti-rabbit HRP antibody (Pierce, Rockford, Ill.). The common antigen antibody showed good reaction with *C. difficile* spores (about a 10-fold response with $10^4$ spores per ml and an 18-fold response over background at $10^5$ spores per ml) and showed a weak (about 2-fold response over background) with *C. sporogenes* spores and no reaction over background with *B. subtilis* spores (see Table 10). The data presented in Table 10 are the average of readings of three wells and are representative of at least three separate experiments. This antibody may be used as a capture antibody in sandwich ELIZA assays.

TABLE 10

Characterization of rabbit *C. difficile* common antigen antibody
Absorbance at 450 nm

| Spores/ml | B. subtilis | C. sporogenes | C. difficile |
|---|---|---|---|
| 1.00E+03 | 0.14 | 0.15 | 0.44 |
| 1.00E+04 | 0.15 | 0.15 | 2.13 |
| 1.00E+05 | 0.2 | 0.31 | 3.69 |
| No antigen control | 0.19 | 0.19 | 0.19 |

Example 9

Binding of *C. difficile* Antibodies to Vegetative Cells

The rabbit polyclonal antibody to inactivated spores (described in more detail in Example 2), rabbit polyclonal antibody to CD1021 sequence SEQ ID NO:3 (described in more detail in Example 5), rabbit polyclonal antibody to the two amidase peptides SEQ ID NO:7 and SEQ ID NO:8 (described in more detail in Example 7), and the commercially available anti-GDH antibody (described in more detail in Example 8) were screened by ELISA for binding to vegetative cells of *C. difficile*. *C. difficile* ATCC strains 43594, 43596, and 43603 were grown in thioglycollate medium under anaerobic conditions for 16 to 18 hours. The cells were serially diluted in antigen coating buffer and 100 µl of various dilutions was added to the ELISA plate and the plate was incubated under anaerobic condition for one hour at 37° C., to prevent sporulation. The plates were emptied and washed three times with wash buffer and blocked with blocking buffer for one hour under anaerobic conditions at 37° C. The plate was emptied and washed three times with wash buffer and incubated with primary antibody at RT for one hour. The plates were emptied, washed three times with wash buffer, incubated with secondary antibody with HRP label (1:10,000) for one hour at RT. The plates were washed and substrate was added to develop color and plates were read at 450 nm after adding the stop solution. The rabbit polyclonal antibodies to inactivated spores, CD1021 (SEQ ID NO:3) and amidase (SEQ ID NO:7 and SEQ ID NO:8) did not show any binding with vegetative cells (about $10^3$ to $10^7$ cells per ml). However, the commercially available anti-GDH antibody showed good binding at about $10^7$ cells per ml, with a four-fold enhancement of signal over control (see Table 11). The data presented in Table 11 are the average of readings of three wells and are representative of two separate experiments.

TABLE 11

Binding of antibodies with vegetative cells.

| Antibody | No antigen control | $10^3$ cells/ml | $10^4$ cells/ml | $10^5$ cells/ml | $10^6$ cells/ml | $10^7$ cells/ml |
|---|---|---|---|---|---|---|
| ATCC 43594 Absorbance at 450 nm | | | | | | |
| Spore Ab | 0.12 | 0.11 | 0.13 | 0.12 | 0.12 | 0.16 |
| Amidase Ab | 0.15 | 0.14 | 0.11 | 0.11 | 0.12 | 0.27 |
| CD1021 peptide 1 Ab | 0.11 | 0.11 | 0.11 | 0.12 | 0.12 | 0.24 |
| GDH Ab | 0.12 | 0.11 | 0.10 | 0.14 | 0.35 | 0.85 |
| ATCC 43596 Absorbance at 450 nm | | | | | | |
| Spore Ab | 0.12 | 0.12 | 0.12 | 0.11 | 0.11 | 0.14 |
| Amidase Ab | 0.15 | 0.11 | 0.11 | 0.11 | 0.12 | 0.22 |
| CD1021 peptide 1 Ab | 0.11 | 0.11 | 0.12 | 0.11 | 0.13 | 0.21 |
| GDH Ab | 0.12 | 0.11 | 0.12 | 0.16 | 0.40 | 0.76 |
| ATCC 43603 Absorbance at 450 nm | | | | | | |
| Spore Ab | 0.12 | 0.12 | 0.13 | 0.12 | 0.12 | 0.15 |
| Amidase Ab | 0.15 | 0.11 | 0.12 | 0.11 | 0.13 | 0.25 |
| CD1021 peptide 1 Ab | 0.11 | 0.11 | 0.12 | 0.11 | 0.12 | 0.22 |
| GDH Ab | 0.12 | 0.09 | 0.10 | 0.14 | 0.43 | 0.80 |

Example 10

Use of Antibodies in Lateral Flow Devices for C. difficile Spore Detection

Various antibodies described in the above examples, were labeled with Cy3 (Cy3 Ab labeling kit, Amersham Biosciences, Piscataway, N.J.) and tested for ability to detect C. difficile spores. Specifically, the rabbit polyclonal antibody to inactivated spores (described in more detail in Example 2 and referred to as "spore" antibody in Table 12), the rabbit polyclonal antibody to CD1021 sequence SEQ ID NO:3 (described in more detail in Example 5 and referred to as CD1021 peptide 1 Ab in Table 12), the rabbit polyclonal antibody to a mix of the two amidase peptides SEQ ID NO:7 and SEQ ID NO:8 (described in more detail in Example 7 and referred to as amidase peptide Ab in Table 12), and the commercially available rabbit antibody to C. difficile glutamate dehydrogenase common antigen (described in more detail in Example 8 and referred to as "GDH" antibody in Table 12) were labeled and tested.

A typical lateral flow strip with conjugate pad, nitrocellulose membrane, and absorbent pad was prepared. Antibodies were spotted on the nitrocellulose and allowed to dry. Germinated and ungerminated spores ($10^5$ per ml) of C. difficile, C. sporogenes and B. subtilis were mixed with of each of the labeled antibodies (50 µl of 10 µg/ml Cy3 labeled antibody) separately and applied to the conjugate pad. The antibody-spore mixture was allowed to wick for ten minutes. Phosphate buffered saline was used as a control. After ten minutes, the strips were scanned using a microarray scanner (Tecan, Durham, N.C.).

The lateral flow strips using the C. difficile spore antibody, amidase antibody, or the CD1021 antibody, showed that the antibodies are specific in detecting C. difficile spores. The amidase antibody did not detect ungerminated spores, but was able to detect germinated spores. Based on these observations one can design lateral flow strips for detecting C. difficile spores. For example, labeled GDH antibody could be used as a detection reagent and spore antibody or CD1021 antibody as capture reagent to detect ungerminated spores and amidase antibody as capture reagent to detect germinated spores.

As outlined in Table 12, various pairings of antibodies can be used to detect the C. difficile spores, detecting, spores or germinated spores.

TABLE 12

Antibody pairings for detection of C. difficile spores

| Antibody 1 | Antibody2 | Specificity |
|---|---|---|
| Amidase Peptide Ab | GDH | C. difficile germinated spores |
| Amidase Peptide Ab | CD1021 peptide 1 Ab | C. difficile germinated spores |
| Amidase Peptide Ab | Spore | C. difficile germinated spores |
| CD1021 peptide 1 Ab | GDH | C. difficile spores |
| CD1021 Peptide 1 Ab | Amidase Peptide Ab | C. difficile germinated spores |
| CD1021 Peptide 1 Ab | Spore | C. difficile spores |
| Spore | GDH | C. difficile spores |
| Spore | Amidase Peptide Ab | C. difficile germinated spores |
| Spore | CD1021 Peptide 1 Ab | C. difficile spores |
| Spore | Spore | C. difficile spores |

TABLE 12-continued

Antibody pairings for detection of C. difficile spores

| Antibody 1 | Antibody2 | Specificity |
|---|---|---|
| CD1021 Peptide 1 Ab | CD1021 Peptide 1 Ab | C. difficile spores |
| Amidase Peptide Ab | Amidase Peptide Ab | C. difficile germinated spores |

Example 11

Detection of C. difficile Spores on a Surface

100 µl $10^6$ per ml of C. difficile spores were spread on sterile aluminum coupons (1"×3") and allowed to dry at RT for about an hour. The spores were recovered by rubbing vigorously for 5 to 10 seconds with a sterile swab moistened with about 50 µl of sterile PBS. The swabs containing the spores were immersed in 1 ml of coating buffer and vortexed vigorously for one to two minutes. The cotton swab was removed from the solution and recovery of spores was determined by ELISA. For control, the coupons were spread with sterile PBS and processed similarly. As seen in Table 13, the C. difficile spore antibody and the CD1021 peptide 1 Ab were able to detect the presence of spores on a surface.

TABLE 13

Detection of C. difficile spores from aluminum coupons
Absorbance at 450 nm

| | C. difficile | | No antigen control | |
|---|---|---|---|---|
| | Spore Ab | CD1021 peptide 1 Ab | Spore Ab | CD1021 Ab1 |
| Coupon 1 | 1.35 | 1.12 | 0.15 | 0.18 |
| Coupon 2 | 1.64 | 1.24 | 0.18 | 0.21 |
| Coupon 3 | 1.22 | 0.93 | 0.14 | 0.2 |

Example 12

Antigen Affinity Purification of Antibodies

The purification of an antibody specific for a particular antigen and free of cross reactants from other immunoglobulins is often beneficial. Any of the polyclonal antibodies described in the above examples may be purified by affinity chromatography using the peptide or protein antigen covalently bound to an affinity matrix through $NH_2$ linkages. Purification can be achieved using peptide/protein bound affinity matrix such as Affygel (Biorad, Hercules, Calif.), AminoLink resin (Pierce, Rockford, Ill.) or CNBr activated Sepharose 4B (Amersham Biosciences, Piscataway, N.J.) in a column. The antibodies that are specific to the antigen bind to the column. The unbound antibodies and other serum proteins pass through the column. The antigen bound antibodies are then eluted from the column. The resulting purified antibody is highly specific.

Example 13

Antibodies to Additional Regions of C. Difficile Hypothetical Protein CD1021

Following the procedures described in more detail in Example 4, murine polyclonal and monoclonal antibodies can be developed to additional polypeptide sequences of the hypothetical protein CD1021 *C. difficile* strain 630. For example, a polypeptide having residues 30 to 120 of the hypothetical protein CD1021 *C. difficile* strain 630 having the amino acid sequence of KSVDLYSDVY IEKYFNRDKV MEVNIEIDES DLKDMNENAI KEEFKVAKVT VDGDTYGNVG IRTKGNSSLI SVANSDSDRY SYKINFDKYN T (SEQ ID NO: 9) or a polypeptide having residues 194 to 293 of the hypothetical protein CD1021 *C. difficile* strain 630 having the amino acid sequence of VTGDLYKSDE GSSLQYKGDD PESYSNLIVE SDKKTADWSK ITKLLKSLDT GEDIEKYLDV DSVLKNIAIN TALLNLDSYQ GSFAHNYYLY EQDGVFSMLP (SEQ ID NO: 10) can be used as immunogens. Polyclonal and monoclonal antibodies can also be developed to fragments thereof, including, for example, fragments of about 10-20 amino acids and about 14 amino acids of SEQ ID NO:9 and SEQ ID NO:10.

Example 14

Monoclonal Antibodies

Monoclonal antibodies that bind to *C. difficile* endospores may be produced by a variety of known methods. Monoclonal antibodies may be produced using any of SEQ ID NO:1-12, 16-23, 38, and 45-50, and fragments thereof, as an antigen. For example, mice that have been immunized with the hypothetical CD1021 protein sequence SEQ ID NO:2, as described in Example 4, or the putative amidase protein sequence SEQ ID NO:6, as described in Example 6, may be used for the generation of murine monoclonal antibodies. Further, rabbits that have been immunized with the hypothetical CD1021 peptides SEQ ID NO:3 or SEQ ID NO:4, as described in Example 5, or the putative amidase peptide sequences SEQ ID NO:7 or SEQ ID NO:8, as described in Example 7, may be used for the generation of rabbit monoclonal antibodies. Epitomic's proprietary method for making monoclonal antibodies from rabbits rather than the conventional method of starting with mice may be used. The basic principal for making the antibody is the same as for mouse monoclonals. A proprietary rabbit fusion partner is used that can fuse to rabbit B-cells to create the rabbit hybridoma cells. Hybridomas are then screened to select for clones with specific and sensitive antigen recognition and the antibodies are characterized using a variety of methods.

Example 15

Blast Analysis

The *C. difficile* strain 630 protein sequences for the hypothetical protein CD1021 (YP_001087502) (SEQ ID NO:1) and the putative N-acetylmuramoyl-L-alanine amidase cell surface protein (YP_001087517) (SEQ ID NO:5) were searched for homologies against the approximately 988 microbial genomic sequences available at GenBank, RefSeq Nucleotides, EMBL, DDBJ, and PDB sequences (excluding HTGS0, 1, 2, EST, GSS, STS, PAT, WGS). Sequences producing significant alignments (E value of 0.0) were found only in the genomic sequence databases for *C. difficile* strain 630, *C. difficile* QCD-66c26, and *C. difficile* QCD-32g58. Hypothetical Protein CD1021 in *C. difficile* QCD-32g58.

For hypothetical protein CD1021 of *C. difficile* strain 630 (SEQ ID NO:1) the following sequences with significant homology (E value of 0.0) were found in *C. difficile* QCD-32g58.

GenBank Accession No. ZP_01804840, hypothetical protein CdifQ_04001048 in *C. difficile* QCD-32g58 having the amino acid sequence:

```
                                          (SEQ ID NO: 11)
MIIFLCAVVG VYSTSSNKSV DLYSDVYIEK YFNRDKVMEV
NIEIDESDLK DMNENAIKEE FKVAKVTVDG DTYGNVGIRT
KGNSSLTSVA NSDSDRYSYK INFDKYNTSQ SMEGLTQLNL
NNCYSDPSYM REFLTYSICE EMGLATPEFA YAKVSINGEY
HGLYLAVEGL KESYLENNFG NVTGDLYKSD EGSSLQYKGD
DPESYSNLIV ESDKKTADWS KITKLLKSLD TGEDIEKYLD
VDSVLKNIAI NTALLNLDSY QGSFAHNYYL YEQDGVFSML
PWDFNMSFGG FSGFGGGSQS IAIDEPTTGN LEDRPLISSL
LKK.
```

GenBank Accession No. ZP_01804841, hypothetical protein CdifQ_04001049 in *C. difficile* QCD-32g58 having the amino acid sequence:

```
                                          (SEQ ID NO: 12)
MTTKLHDMIA SYVKEDPTAF YTYEEFEKNI TSSIEDSSDN
KGFGNKGFDN NNSNNSDSNN NSNSENKRSG NQSDKKEVNA
ELTSSVVKTN TDNETENKTT NDSESKNNTD KDKSGNDNNQ
KLEGPRGKGG KSIPGVLEVA EDMSKTIKSQ LSGETSSTKQ
NSGDESSSGI KGSEKFDEDM SGMPEPPEGM DGKMPPGMGN
MDKGDMNGKN GNMNMDRNQD NPREAGGFGN RGGGSVSKTT
TYFKLILGGA SMIIMSIMLV GVSRVKRRRF IKSK.
```

REGION 461827 to 462825 of GenBank Accession No. NZ_AAML04000007; *C. difficile* QCD-32g58 C_difficile_bld4_cont00007 having the nucleotide sequence:

```
                                          (SEQ ID NO: 13)
AAGATAAAAA AATTTACCCT TCTTATCTCT ATTATGATTA
TATTTTTATG TGCTGTAGTT GGAGTTTATA GTACATCTAG
CAACAAAAGT GTTGATTTAT ATAGTGATGT ATATATTGAA
AAATATTTTA ACAGAGACAA GGTTATGGAA GTTAATATAG
AGATAGATGA AAGTGACTTG AAGGATATGA ATGAAAATGC
TATAAAAGAA GAATTTAAGG TTGCAAAAGT AACTGTAGAT
GGAGATACAT ATGGAAACGT AGGTATAAGA ACTAAAGGAA
ATTCAAGTCT TACATCTGTA GCAAATAGTG ATAGTGATAG
ATACAGCTAT AAGATTAATT TTGATAAGTA TAATACTAGT
CAAAGTATGG AAGGGCTTAC TCAATTAAAT CTTAATAACT
GTTACTCTGA CCCATCTTAT ATGAGAGAGT TTTTAACATA
TAGTATTTGC GAGGAAATGG GATTAGCGAC TCCAGAATTT
GCATATGCTA AAGTCTCTAT AAATGGCGAA TATCATGGTT
TGTATTTGGC AGTAGAAGGA TTAAAAGAGT CTTATCTTGA
AAATAATTTT GGTAATGTAA CTGGAGACTT ATATAAGTCA
```

-continued

```
GATGAAGGAA GCTCGTTGCA ATATAAAGGA GATGACCCAG

AAAGTTACTC AAACTTAATC GTTGAAAGTG ATAAAAAGAC

AGCTGATTGG TCTAAAATTA CAAAACTATT AAAATCTTTG

GATACAGGTG AAGATATTGA AAAATATCTT GATGTAGATT

CTGTCCTTAA AAATATAGCA ATAAATACAG CTTTATTAAA

CCTTGATAGC TATCAAGGCA GTTTTGCCCA TAACTATTAT

TTATATGAGC AAGATGGAGT ATTTTCTATG TTACCATGGG

ATTTTAATAT GTCATTTGGT GGATTTAGTG GTTTTGGTGG

AGGTAGTCAA TCTATAGCAA TTGATGAACC TACGACAGGT

AATTTAGAAG ACAGACCTCT CATATCCTCG TTATTAAAA.
```

An amino acid sequence encoded by nucleotide sequence SEQ ID NO:13 is:

```
                                   (SEQ ID NO: 21)
KIKKFTLLIS IMIIFLCAVV GVYSTSSNKS VDLYSDVYIE

KYFNRDKVME VNIEIDESDL KDMNENAIKE EFKVAKVTVD

GDTYGNVGIR TKGNSSLTSV ANSDSDRYSY KINFDKYNTS

QSMEGLTQLN LNNCYSDPSY MREFLTYSIC EEMGLATPEF

AYAKVSINGE YHGLYLAVEG LKESYLENNF GNVTGDLYKS

DEGSSLQYKG DDPESYSNLI VESDKKTADW SKITKLLKSL

DTGEDIEKYL DVDSVLKNIA INTALLNLDS YQGSFAHNYY

LYEQDGVFSM LPWDFNMSFG GFSGFGGGSQ SIAIDEPTTG

NLEDRPLISS LLK.
```

And, REGION 462824 to 463732 of GenBank Accession No. NZ_AAML04000007; *C. difficile* QCD-32g58_difficile_bld4_cont00007 having the nucleotide sequence:

```
                                   (SEQ ID NO: 14)
AAAAATGAGA CACACAAAAC AAAATACCAT AAATATCTGG

AAGAGATAGT AACAAAATAC CTAGATTCAG ACTATTTAGA

GAATATGACA ACAAAATTGC ATGACATGAT AGCATCATAT

GTAAAAGAAG ACCCAACAGC ATTTTATACT TATGAAGAAT

TTGAAAAAAA TATAACATCT TCAATTGAAG ATTCTAGTGA

TAATAAGGGA TTTGGTAATA AAGGGTTTGA CACACAAAAC

TCTAATAACA GTGATTCTAA TAATAATTCT AATAGTGAAA

ATAAGCGCTC TGGAAATCAA AGTGATAAAA AAGAAGTTAA

TGCTGAATTA ACATCAAGCG TAGTCAAAAC TAATACAGAT

AATGAAACTG AAAATAAAAC TACAAATGAT AGCGAAAGTA

AGAATAATAC AGATAAAGAT AAAAGTGGAA ATGATAATAA

TCAAAAGCTA GAAGGTCCTA GGGGTAAAGG AGGTAAGTCA

ATACCAGGGG TTTTGGAAGT TGCAGAAGAT ATGAGTAAAA

CTATAAAATC TCAATTAAGT GGAGAAACTT CTTCGACAAA

GCAAAACTCT GGTGATGAAA GTTCAAGTGG AATTAAAGGT

AGTGAAAAGT TTGATGAGGA TATGAGTGGT ATGCCAGAAC

CACCTGAGGG AATGGATGGT AAAATGCCAC CAGGAATGGG

TAATATGGAT AAGGGAGATA TGAATGGTAA AAATGGCAAT

ATGAATATGG ATAGAAATCA AGATAATCCA AGAGAAGAAG

GAGGTTTTGG CAATAGAGGA GGAGGCTCTG TGAGTAAAAC

AACAACATAC TTCAAATTAA TTTTAGGTGG AGCTTCAATG

ATAATAATGT CGATTATGTT AGTAGGTGTA TCAAGGGTAA

AGAGAAGAAG ATTTATAAAG TCAAAATAA.
```

An amino acid sequence encoded by nucleotide sequence SEQ ID NO:14 is:

```
                                   (SEQ ID NO: 22)
KNETHKTKYH KYLEEIVTKY LDSDYLENMT TKLHDMIASY

VKEDPTAFYT YEEFEKNITS SIEDSSDNKG FGNKGFDNNN

SNNSDSNNNS NSENKRSGNQ SDKKEVNAEL TSSVVKTNTD

NETENKTTND SESKNNTDKD KSGNDNNQKL EGPRGKGGKS

IPGVLEVAED MSKTIKSQLS GETSSTKQNS GDESSSGIKG

SEKFDEDMSG MPEPPEGMDG KMPPGMGNMD KGDMNGKNGN

MNMDRNQDNP REAGGFGNRG GGSVSKTTTY FKLILGGASM

IIMSIMLVGV SRVKRRRFIK SK.
```

Hypothetical Protein CD1021 in *C. difficile* QCD-66c26

For hypothetical protein CD1021 of *C. difficile* strain 630 (SEQ ID NO:1) one sequence with significant homology (E value of 0.0) was found in *C. difficile* QCD-66c26.

The complement of REGION 15690 to 17597 of GenBank Accession No. NZ_ABFD01000037; *C. difficile* QCD-66c26 contig00122 having the nucleotide sequence:

```
                                   (SEQ ID NO: 15)
ATGAAAGATA AAAAATTTAC CCTTCTTATC TCTATTATGA

TTATATTTTT ATGTGCTGTA TTGGAGTTT ATAGTACATC

TAGCAACAAA AGTGTTGATT TATATAGTGA TGTATATATT

GAAAAATATT TTAACAGAGA CAAGGTTATG GAAGTTAATA

TAGAGATAGA TGAAAGTGAC TTGAAGGATA TGAATGAAAA

TGCTATAAAA GAAGAATTTA AGGTTGCAAA AGTAACTGTA

GATGGAGATA CATATGGAAA CGTAGGTATA AGAACTAAAG

GAAATTCAAG TCTTACATCT GTAGCAAATA GTGATAGTGA

TAGATACAGC TATAAGATTA ATTTTGATAA GTATAATACT

AGTCAAAGTA TGGAAGGGCT TACTCAATTA AATCTTAATA

ACTGTTACTC TGACCCATCT TATATGAGAG AGTTTTTAAC

ATATAGTATT TGCGAGGAAA TGGGATTAGC GACTCCAGAA

TTTGCATATG CTAAAGTCTC TATAAATGGC GAATATCATG

GTTTGTATTT GGCAGTAGAA GGATTAAAAG AGTCTTATCT

TGAAAATAAT TTTGGTAATG TAACTGGAGA CTTATATAAG
```

-continued

```
TCAGATGAAG GAAGCTCGTT GCAATATAAA GGAGATGACC

CAGAAAGTTA CTCAAACTTA ATCGTTGAAA GTGATAAAAA

GACAGCTGAT TGGTCTAAAA TTACAAAACT ATTAAAATCT

TTGGATACAG GTGAAGATAT TGAAAAATAT CTTGATGTAG

ATTCTGTCCT TAAAAATATA GCAATAAATA CAGCTTTATT

AAACCTTGAT AGCTATCAAG GCAGTTTTGC CCATAACTAT

TATTTATATG AGCAAGATGG AGTATTTTCT ATGTTACCAT

GGGATTTTAA TATGTCATTT GGTGGATTTA GTGGTTTTGG

TGGAGGTAGT CAATCTATAG CAATTGATGA ACCTACGACA

GGTAATTTAG AAGACAGACC TCTCATATCC TCGTTATTAA

AAAATGAGAC ACACAAAACA AAATACCATA AATATCTGGA

AGAGATAGTA ACAAAATACC TAGAGATAGA CTATTTAGAG

AATATGACAA CAAAATTGCA TGACATGATA GCATCATATG

TAGAGATAGA CCCAACAGCA TTTTATACTT ATGAAGAATT

TGAAAAAAAT ATAACATCTT CAATTGAAGA TTCTAGTGAT

AATAAGGGAT TTGGTAATAA AGGGTTTGAC AACAATAACT

CTAATAACAG TGATTCTAAT AATAATTCTA ATAGTGAAAA

TAAGCGCTCT GGAAATCAAA GTGATAAAAA AGAAGTTAAT

GCTGAATTAA CATCAAGCGT AGTCAAAACT AATACAGATA

ATGAAACTGA AAATAAAACT ACAAATGATA GCGAAAGTAA

GAATAATACA GATAAAGATA AAAGTGGAAA TGATAATAAT

CAAAAGCTAG AAGGTCCTAG GGGTAAAGGA GGTAAGTCAA

TACCAGGGGT TTTGGAAGTT GCAGAAGATA TGAGTAAAAC

TATAAAATCT CAATTAAGTG GAGAAACTTC TTCGACAAAG

CAAAACTCTG GTGATGAAAG TTCAAGTGGA ATTAAAGGTA

GTGAAAAGTT TGATGAGGAT ATGAGTGGTA TGCCAGAACC

ACCTGAGGGA ATGGATGGTA AAATGCCACC AGGAATGGGT

AATATGGATA AGGGAGATAT GAATGGTAAA AATGGCAATA

TGAATATGGA TAGAAATCAA GATAATCCAA GAGAAGCTGG

AGGTTTTGGC AATAGAGGAG GAGGCTCTGT GAGTAAAACA

ACAACATACT TCAAATTAAT TTTAGGTGGA GCTTCAATGA

TAATAATGTC GATTATGTTA GTAGGTGTAT CAAGGGTAAA

GAGAAGAAGA TTTATAAAGT CAAAATAA.
```

An amino acid sequence encoded by nucleotide sequence SEQ ID NO:15 is:

```
                                    (SEQ ID NO: 23)
MKDKKFTLLI SIMIIFLCAV VGVYSTSSNK SVDLYSDVYI
EKYFNRDKVM EVNIEIDESD LKDMNENAIK EEFKVAKVTV
DGDTYGNVGI RTKGNSSLTS VANSDSDRYS YKINFDKYNT
SQSMEGLTQL NLNNCYSDPS YMREFLTYSI CEEMGLATPE
FAYAKVSING EYHGLYLAVE GLKESYLENN FGNVTGDLYK
```

-continued

```
SDEGSSLQYK GDDPESYSNL IVESDKKTAD WSKITKLLKS
LDTGEDIEKY LDVDSVLKNI AINTALLNLD SYQGSFAHNY
YLYEQDGVFS MLPWDFNMSF GGFSGFGGGS QSIAIDEPTT
GNLEDRPLIS SLLKNETHKT KYHKYLEEIV TKYLDSDYLE
NMTTKLHDMI ASYVKEDPTA FYTYEEFEKN ITSSIEDSSD
NKGFGNKGFD NNNSNNSDSN NNSNSENKRS GNQSDKKEVN
AELTSSVVKT NTDNETENKT TNDSESKNNT DKDKSGNDNN
QKLEGPRGKG GKSIPGVLEV AEDMSKTIKS QLSGETSSTK
QNSGDESSSG IKGSEKFDED MSGMPEPPEG MDGKMPPGMG
NMDKGDMNGK NGNMNMDRNQ DNPREAGGFG NRGGGSVSKT
TTYFKLILGG ASMIIMSIML VGVSRVKRRR FIKSK.
```

FIG. 1 demonstrates the high degree of homology between the amino acid sequences for hypothetical CD1021 proteins YP_001087502 from *C. difficile* strain 630 (SEQ ID NO:1), ZP_01804840, from *C. difficile* QCD-32g58 (SEQ ID NO:11), ZP_01804841 from *C. difficile* QCD-32g58 (SEQ ID NO:12), Region 461827 to 462825 NZ_AAML04000007 from *C. difficile* QCD-32g58 (SEQ ID NO:21), Region 462824 to 463732 of NZ_AAML04000007 *C. difficile* QCD-32g58 (SEQ ID NO:22), and the complement of Region 15690 to 17597 NZ-ABFD01000037 from *C. difficile* QCD-66c26 (SEQ ID NO:23). A consensus sequence is shown as SEQ ID NO:38.

Putative N-Acetylmuramoyl-L-Alanine Amidase Cell Surface Proteins

For putative N-acetylmuramoyl-L-alanine amidase cell surface protein of *C. difficile* strain 630 (SEQ ID NO:5) the following additional sequences with significant homology (E value of 0.0) in *C. difficile* strain 630 were found.

GenBank Accession No. YP_001087516, cell surface protein putative N-acetylmuramoyl-L-alanine amidase, *C. difficile* strain 630, having the amino acid sequence:

```
                                    (SEQ ID NO: 16)
MLSKEINMRR NTKLLTTGIL SMAIVTPTMA FATESNAMEN
NADLNINLEK KSIVLGSTSK VSVKFKEKPD ADSITLKYKC
YDMPLDTTLN YNQSTESYEG TINYNKDPEY LNVWELQGIT
INSKNNPKTL NKQELEKMGL NLKDYNVTQE CIIEDITSRK
DVNKYLRKTS APITELTGSD RYETAVKISK EGWKNGSDKV
VIINGDVSID GIISTPLATT YNAPILLVEK NNVPNSVKSE
LKRLNPRDVI IIGDENAISK TTANQIKSTV NASQTRLKGS
NRYETSLLIA KEIDKNHDVE KVYITNANGG EVDALTIAAK
AGQDKQPIIL TDKNSITDNT YKWLKSEDLQ NAYFIGGPQM
ISTNVINKVN DITKDNVTNN RVYGADRHET NANVIKKFYT
DDELEAVLVA KSDVLVDALA AGPLAANLKS PILITPKTYV
SAYHKENLEA KSANKVYKIG GGLTSKVMSS IASSLSKHNT
TPTEPGNSGG KTVMIDPGHG GSDTGTTGKP LGGIREKDYT
LNTSLATTEY LRSKGFNVIM TRDTDKTLSL GNRTALSNSL
```

```
RPDLFTSIHY NASDTTGNGV EVFYKLKDKD GGTTKTVATN

ILNRILEKFN LKNRGAKTRT LSTDPTKDYL YVLRNNDMPA

VLVECAFLDN EKDMSLLNTS NKVKEMGTQI GKGIEDSLK.
```

And, GenBank Accession No. YP_001089297 (cell surface protein *C. difficile* 630) having the amino acid sequence:

```
                                      (SEQ ID NO: 17)
MMKKTTKLLA TGMLSVAMVA PNVALAAENT TANTESNSDI

NINLQRKSVV LGSKSNASVK FKEKLNADSI TLNFMCYDMP

LEATLNYNEK TDSYEGVINY NKDPEYLNVW ELQSIKINGK

DEQKVLNKED LESMGLNLKD YDVTQEFIIS DANSTKAVNE

YMRKTSAPVK KLAGATRFET AVEISKQGWK DGSSKVVIVN

GELAADGITA TPLASTYDAP ILLANKDDIP ESTKAELKRL

NPSDVIIIGD DGSVSQKAVS QIKSAVNVNV TRIGGVDRHE

TSLLIAKEID KYHDVNKIYI ANGYAGEYDA LNISSKAGED

QQPIILANKD SVPQGTYNWL SSQGLEEAYY IGGSQSLSSK

IIDQISKIAK NGTSKNRVSG ADRHETNANV IKTFYPDKEL

SAMLVAKSDI IVDSITAGPL AAKLKAPILI TPKTYVSAYH

STNLSEKTAE TVYQIGDGMK DSVINSIASS LSKHNAPTEP

DNSGSAAGKT VVIDPGHGGS DSGATSGLNG GAQEKKYTLN

TALATTEYLR SKGINVVMTR DTDKTMALGE RTALSNTIKP

DLFTSIHYNA SNGSGNGVEI YYKVKDKNGG TTKTAASNIL

KRILEKFNMK NRGIKTRTLD NGKDYLYVLR NNNYPAILVE

CAFIDNKSDM DKLNTAEKVK TMGTQIGIGI EDTVK.
```

For putative N-acetylmuramoyl-L-alanine amidase cell surface protein of *C. difficile* strain 630 (SEQ ID NO:5) the following sequences with significant homology (E value of 0.0) were found in *C. difficile* QCD-32g58.

GenBank Accession No. ZP_01804350 (hypothetical protein CdifQ_04001133; *C. difficile* QCD-32g58) having the amino acid sequence:

```
                                      (SEQ ID NO: 18)
MFRFKEKPDA DSITLKYKCY DMPLDTTLNY NQSTESYEGT

INYNKDPEYL NVWELQGITI NSKNNPKTLN KQELEKMGLN

LKDYNVTQEC IIEDITSRKD VNKYLRKTSA PITELTGSDR

YETAVKISKE GWKNGSDKVV IINGDVSIDG IISTPLATTY

NAPILLVEKN NVPNSVKSEL KRLNPRDVII IGDENAISKT

TANQIKSTVN ASQTRLKGSN RYETSLLIAK EIDKNHDVEK

VYITNANGGE VDALTIAAKA GQDKQPIILT DKNSITDNTY

KWLKSEDLQN AYFIGGPQMI STNVINKVND ITKDNVTNNR

VYGADRHETN ANVIKKFYTD DELEAVLVAK SDVLVDALAA

GPLAANLKSP ILITPKTYVS AYHKDNLEAK SANKVYKIGG

GLTSKVMNSI ASSLSKHNTT PTEPGNSGGK TVMIDPGHGG

SDTGTTGKPL GGIKEKDYTL NTSLATTEYL RSKGFNVIMT

RDTDKTLSLG NRTALSNSLR PDLFTSIHYN ASDTTGNGVE

VFYKLKDKDG GTTKTVATNI LNRILEKFNL KNRGAKTRTL

STDPTKDYLY VLRNNDMPAV LVECAFLDNE KDMSLLNTSN

KVKEMGTQIG KGIEDSLK.
```

GENEBANK Accession No. ZP_01804351 (hypothetical protein CdifQ_04001134; *C. difficile* QCD-32g58) having the amino acid sequence:

```
                                      (SEQ ID NO: 19)
MLSKEINMRR NTKLLTTGIL SMAIVAPTMA FATESNAMEN

NADLNINLEK KSIVLGSKSK VSVKFKEKPD ADSITLKYKC

YDMPLDTTLN YNQSTGAYEG TINYNQDPEY LNVWELQGIT

INSKNNPKTL NGQDLEKMGL NLKDYNVTQE CIIEDITSRK

DVNKYLRKTS APITELTGSD RYETAVKISK EGWKNGSDKV

VIINGDVSID GIISTPLATT YNAPILLVEK NNVPNSVKSE

LKRLNPKDII IGDENAISK TTANQIKSTV NASQTRLNGS

NRYETSLLIA KEIDKNHDVE KVYITNANGG EVDALTIAAK

AGQDKQPIIL TDKDSITDNT YKWLKSEDLQ NAYFIGGPQM

ISTNVINKVN GITKDSVTNN RVYGADRHET NANVIKKFYT

EDEIEAVLVA KSDVLVDALA AGPLAANLKS PILITPKTYV

SAYHKDNLEA KSANKVYKIG GGLTSKVMSS IASSLSKHNT

TPTEPGNSGG KTVMIDPGHG GSAPGNSSGG MIEKDYNLNT

SLATTEYLRS KGFNVIMTRD TDKTLSLGNR TA.
```

And, GenBank Accession No. ZP_01802273 (hypothetical protein CdifQ_04003247; *C. difficile* QCD-32g58) having the amino acid sequence:

```
                                      (SEQ ID NO: 20)
MMKKTTKLLA TGMLSVAMVA PNVALAAENT TANTESNSDI

NINLQRKSVV LGSKSNASVK FKEKLNADSI TLNFMCYDMP

LEATLNYNEK TDSYEGVINY NKDPEYLNVW ELQSIKINGK

DEQKVLNKED LESMGLNLKD YDVTQEFIIS DANSTKAVNE

YMRKTSAPVK KLAGATRFET AVEISKQGWK DGSSKVVIVN

GELAADGITA TPLASTYDAP ILLANKDDIP ESTKAELKRL

NPSDVIIIGD DGSVSQKAVS QIKSAVNVNV TRIGGVDRHE

TSLLIAKEID KYHDVNKIYI ANGYAGEYDA LNISSKAGED

QQPIILANKD SVPQGTYNWL SSQGLEEAYY IGGSQSLSSK

IIDQISKIAK NGTSKNRVSG ADRHETNANV IKTFYPDKEL

SAMLVAKSDI IVDSITAGPL AAKLKAPILI TPKTYVSAYH

STNLSEKTAG TVYQIGDGMK DSVINSIASS LSKHNAPTEP

DNSGSAAGKT VVIDPGHGGS DSGATSGLNG GAQEKKYTLN

TALATTEYLR SKGINVVMTR DTDKTMALGE RTALSNTIKP

DLFTSIHYNA SNGAGNGVEI YYKVKDKNGG TTKTAASNIL
```

```
KRILEKFNMK NRGIKTRTLD NGKDYLYVLR NNNYPAILVE

CAFIDNKSDM DKLNTAEKVK TMGTQIGIGI EDTVK.
```

The antibodies described herein may bind to one or more of the amino acid sequences of SEQ ID NO:11, SEQ ID NO:12, SEQ ID NO:16, SEQ ID NO:17, SEQ ID NO:18, SEQ ID NO:19, SEQ ID NO:20, SEQ ID NO:21, SEQ ID NO:22, and SEQ ID NO:23, and fragments thereof. Antibodies described herein may bind to one or more of the amino acid sequences encoded by the genomic nucleotide sequences of SEQ ID NO:13, SEQ ID NO:14, and SEQ ID NO:15 and polypeptide fragment thereof.

Antibodies may be produced, by any of a variety methods, including, but not limited to, any of those described herein, that bind to one or more of the amino acid sequences of SEQ ID NO:11, SEQ ID NO:12, SEQ ID NO:16, SEQ ID NO:17, SEQ ID NO:18, SEQ ID NO:19, SEQ ID NO:20, SEQ ID NO:21, SEQ ID NO:22, and SEQ ID NO:23, and fragment thereof. Antibodies may be produced, by any of the various methods described herein, that bind to one or more of the amino acid sequences encoded by the genomic nucleotide sequences of SEQ ID NO:13, SEQ ID NO:14, and SEQ ID NO:15 and polypeptide fragment thereof. Any such antibodies may be used in methods of detecting *C. difficile* spores in a sample.

Example 16

Cloning and Sequencing CD1021 from *C. difficile* ATCC 9689

A CD1021 coding sequence was amplified by PCR using a forward primer with NheI site (5'-TAAGCTAGCATGAAA-GATAAAAAATTTACC-3') (SEQ ID NO:24), a reverse primer with XhoI site (5'-TTACTCGAGTTTTGACTT-TATAAATCTTCT-3') (SEQ ID NO:25) and genomic DNA from ATCC strain 9689 as the template. A stop codon was removed from the reverse primer to facilitate addition of 6-HIS tag to the end of the sequence. The resulting fragment size was 1923 base pairs (bp).

Similarly, the region corresponding to amino acid residues 30 to 120 of CD1021 in *C. difficile* strain 630 (SEQ ID NO:9) (also referred to herein as "fragment 1") was amplified using genomic DNA from ATCC strain 9689 as the template with a forward primer with NheI site (5'-ACAGCTAGCAT-GAAAAGTGTTGATTTATATAGT-3') (SEQ ID NO:26) and a reverse primer with XhoI site (5'-ACTCTCGAGAGTAT-TATACTTATCAAAATTA-3') (SEQ ID NO:27). The resulting fragment size was 294 bp and included an ATG initiation codon.

The region corresponding to amino acid residues 194 to 293 of CD1021 in *C. difficile* strain 630 (SEQ ID NO:10) (also referred to herein as "fragment 2") was amplified using genomic DNA from ATCC strain 9689 as the template with a forward primer with NheI site (5'-AATGCTAGCATGG-TAACTGGAG ACTTATATAAGTCA-3') (SEQ ID NO:28) and a reverse primer with XhoI site (5'-AAACTCGAGTGG TAACA TAGAAAATACTCCAT-3') (SEQ ID NO:29). The resulting fragment size was 321 bp and included an ATG initiation codon.

And, the region corresponding to amino acid residues 505 to 604 of CD1021 in *C. difficile* strain 630 (SEQ ID NO:2) (also referred to herein as "fragment 3") was amplified using genomic DNA from ATCC strain 9689 as the template with a forward primer with NheI site (5'-GCAGCTAGCATGAG-TAAAACTATAAAATCTCAA-3') (SEQ ID NO:30) and a reverse primer with XhoI site (5'-AATCTCGAGGAAGTAT-GTTGTTGTTTTACT CAC-3') (SEQ ID NO:31). The resulting fragment size was 321 bp and included an ATG initiation codon.

The resultant PCR reactions were run on an agarose gel (0.8%) and products of the expected size were observed. The PCR fragments were cloned using Zero Blunt TOPO PCR Cloning Kit (Invitrogen, Carlsbad, Calif.) according to manufacturer's instructions. The transformed colonies were picked and grown in LB with Kanamycin (100 μg/ml) for 16 hours at 37° C. The plasmid was isolated from these cultures using Qiaprep spin miniprep kit (Qiagen, Valencia, Calif.) and the plasmids were cut with EcoRI (Invitrogen) and analyzed by agarose gel. The clones having the insert were sequenced using BigDye® Terminator v1.1 Cycle Sequencing Kit (Applied Biosystems, Foster City, Calif.) with M13 forward -20 primer (5'-GTAAAACGACGGCCAGT-3') (SEQ ID NO:32) and M13 reverse -27 primer (5'-CAGGAAACAGCTAT-GAC-3') (SEQ ID NO:33). Appropriate internal primers were used to obtain the complete sequence of the 1923 bp CD1021 coding sequence. Three clones were selected for further characterization for each of the four cloning reactions. For the 1923 bp CD1021 coding sequence, the three clones were pCD1021-1, pCD1021-2, and pCD1021-3. For fragment 1, the three clones were pCD1021-Fr1-1, pCD1021-Fr1-2, and pCD1021-Fr1-3. For fragment 2, the three clones were pCD1021-Fr2-1, pCD1021-Fr2-2, and pCD1021-Fr2-3. For fragment 3, the three clones were pCD1021-F3-1, pCD1021-Fr3-2, and pCD1021-Fr3-3.

The nucleotide sequence of *C. difficile* ATCC 9689 CD1021 fragment in plasmid pCD1021-2 is:

```
                                            (SEQ ID NO: 39)
ATGAAAGATA AAAAATTTAC CCTTCTTATC TCGATTATGA

TTATATTTTT ATGTGCTGTA GTTGGAGTTT ATAGTACATC

TAGCAACAAA AGTGTTGATT TATATAGTGA TGTATATATT

GAAAAATATT TTAACAGAGA CAAGGTTATG GAAGTTAATA

TAGAGATAGA TGAAAGTGAC TTGAAGGATA TGAATGAAAA

TGCTATAAAA GAAGAATTTA AGGTTGCAAA AGTAACTGTA

GATGGAGATA CATATGGAAA CGTAGGTATA AGAACTAAAG

GAAATTCAAG TCTTATATCT GTAGCAAATA GTGATAGTGA

TAGATACAGC TATAAGATTA ATTTTGATAA GTATAATACT

AGTCAAAGTA TGGAAGGGCT TACTCAATTA AATCTTAATA

ACTGTTACTC TGACCCATCT TATATGAGAG AGTTTTTAAC

ATATAGTATT TGCGAGGAAA TGGGATTAGC GACTCCAGAA

TTTGCATATG CTAAAGTCTC TATAAATGGC GAATATCATG

GTTTGTATTT GGCAGTAGAA GGATTAAAAG AGTCTTATCT

TGAAAATAAT TTTGGTAATG TAACTGGAGA CTTATATAAG

TCAGATGAAG GAAGCTCGTT GCAATATAAA GGAGATGACC

CAGAAAGTTA CTCAAACTTA ATCGTTGAAA GTGATAAAAA

GACAGCTGAT TGGTCTAAAA TCACAAAACT ATTAAAATCT

TTGGATACAG GTGAAGATAT TGAAAAATAT CTTGATGTAG

ATTCTGTCCT TAAAAATATA GCAATAAATA CAGCTTTATT
```

-continued

```
AAACCTTGAT AGCTATCAAG GGAGTTTTGC CCATAACTAT

TATTTATATG AGCAAGATGG AGTATTTTCT ATGTTACCAT

GGGATTTTAA TATGTCATTT GGTGGATTTA GTGGTTTTGG

TGGAGGTAGT CAATCTATAG CAATTGATGA ACCTACGACA

GGTAATTTAG AAGACAGACC TCTCATATCC TCGTTATTAA

AAAATGAGAC ATACAAAACA AAATACCATA AATATCTGGA

AGAGATAGTA ACAAAATACC TAGATTCAGA CTATTTAGAG

AATATGACAA CAAAATTGCA TGACATGATA GCATCATATG

TAAAAGAAGA CCCAACAGCA TTTTATACTT ATGAAGAATT

TGAAAAAAAT ATAACATCTT CAATTGAAGA TTCTAGTGAT

AATAAGGGAT TTGGTAATAA AGGGTTTGAC AACAATAACT

CTAATAACAG TGATTCTAAT AATAATTCTA ATAGTGAAAA

TAAGCGCTCT GGAAATCAAA GTGATGAAAA AGAAGTTAAT

GCTGAATTAA CATCAAGCGT AGTCAAAGCT AATACAGATA

ATGAAACTAA AAATAAAACT ACAAATGATA GTGAAAGTAA

GAATAATACA GATAAAGATA AAGTGGAAA TGATAATAAT

CAAAAGCTAG AAGGTCCTAT GGGTAAAGGA GGTAAGTCAA

TACCAGGGGT TTTGGAAGTT GCAGAAGATA TGAGTAAAAC

TATAAAATCT CAATTAAGTG GAGAAACTTC TTCGACAAAG

CAAAACTCTG GTGATGAAAG TTCAAGTGGA ATTAAAGGTA

GTGAAAAGTT TGATGAGGAT ATGAGTGGTA TGCCAGAACC

ACCTGAGGGA ATGGATGGTA AAATGCCACC AGGAATGGGT

AATATGGATA AGGGAGATAT GAATGGTAAA AATGGCAATA

TGAATATGGA TAGAAATCAA GATAATCCAA GAGAAGCTGG

AGGTTTTGGC AATAGAGGAG GAGGCTCTGT GAGAAGAAGA

ACAACATACT TCAAATTAAT TTTAGGTGGA GCTTCAATGA

TAATAATGTC GATTATGTTA GTTGGTGTAT CAAGGGTAAA

GAGAAGAAGA TTTATAAAGT CAAA.
```

The translated amino acid sequence of CD1021 fragment in plasmid pCD1021-2 is:

(SEQ ID NO: 45)
MKDKKFTLLISIMIIFLCAVVGVYSTSSNKSVDLYSDVYIEKYFNRDKVM
EVNIEIDESDLKDMNENAIKEEFKVAKVTVDGDTYGNVGIRTKGNSSLIS
VANSDSDRYSYKINFDKYNTSQSMEGLTQLNLNNCYSDPSYMREFLTYSI
CEEMGLATPEFAYAKVSINGEYHGLYLAVEGLKESYLENNFGNVTGDLYK
SDEGSSLQYKGDDPESYSNLIVESDKKTADWSKITKLLKSLDTGEDIEKY
LDVDSVLKNIAINTALLNLDSYQGSFAHNYYLYEQDGVFSMLPWDFNMSF
GGFSGFGGGSQSIAIDEPTTGNLEDRPLISSLLKNETYKTKYHKYLEEIV
TKYLDSDYLENMTTKLHDMIASYVKEDPTAFYTYEEFEKNITSSIEDSSD
NKGFGNKGFDNNNSNNSDSNNNSNSENKRSGNQSDEKEVNAELTSSVVKA

NTDNETKNKTTNDSESKNNTDKDKSGNDNNQKLEGPMGKGGKSIPGVLEV
AEDMSKTIKSQLSGETSSTKQNSGDESSSGIKGSEKFDEDMSGMPEPPEG
MDGKMPPGMGNMDKGDMNGKNGNMNMDRNQDNPREAGGFGNRGGGSVSKT
TTYFKLILGGASMIIMSIMLVGVSRVKRRRFIKSK.

The nucleotide sequence of *C. difficile* ATCC 9689 CD1021 fragment (30 to 120 amino acid residues) in plasmid pCD1021-Fr1-1 is:

(SEQ ID NO: 40)
```
ATGAAAAGTG TTGATTTATA TAGTGATGTA TATATTGAAA

AATATTTTAA CAGAGACAAG GTTATGGAAG TTAATATAGA

GATAGATGAA AGTGACTTGA AGGATATGAA TGAAAATGCT

ATAAAAGAAG AATTTAAGGT TGCAAAAGTA ACTGTAGATG

GAGATACATA TGGAAACGTA GGTATAAGAA CTAAAGGAAA

TTCAAGTCTT ATATCTGTAG CAAATAGTGA TAGTGATAGA

TACAGCTATA AGATTAATTT TGATAAGTAT AATACT.
```

The translated amino acid sequence of CD1021 fragment (30 to 120 amino acid residues) in plasmid pCD1021-Fr1-1 is:

(SEQ ID NO: 46)
MKSVDLYSDVYIEKYFNRDKVMEVNIEIDESDLKDMNENAIKEEFKVAKV
TVDGDTYGNVGIRTKGNSSLISVANSDSDRYSYKINFDKYNT.

The nucleotide sequence of *C. difficile* ATCC 9689 CD1021 fragment (194 to 293 amino acid residues) in plasmid pCD1021-Fr2-1 is:

(SEQ ID NO: 41)
```
ATGGTAACTG GAGACTTATA TAAGTCAGAT GAAGGAAGCT

CGTTGCAATA TAAAGGAGAT GACCCAGAAA GTTACTCAAA

CTTAATCGTT GAAAGTGATA AAAAGACAGC TGATTGGTCT

AAAATCACAA AACTATTAAA ATCTTTGGAT ACAGGTGAAG

ATATTGAAAA ATATCTTGAT GTAGATTCTG TCCTTAAAAA

TATAGCAATA AATACAGCTT TATTAAACCT TGATAGCTAT

CAAGGGAGTT TTGCCCATAA CTATTATTTA TATGAGCAaG

ATGGAGTATT TTCTATGTTA CCA.
```

The translated amino acid sequence of CD1021 fragment (194 to 293 amino acid residues) in plasmid pCD1021-Fr2-1 is:

(SEQ ID NO: 47)
MVTGDLYKSDEGSSLQYKGDDPESYSNLIVESDKKTADWSKITKLLKSLD
TGEDIEKYLDVDSVLKNIAINTALLNLDSYQGSFAHNYYLYEQDGVFSML
P.

The nucleotide sequence of *C. difficile* ATCC 9689 CD1021 fragment (505 to 604 amino acid residues) in plasmid pCD1021-Fr3-1 is:

(SEQ ID NO: 42)
```
ATGAGTAAAA CTATAAAATC TCAATTAAGT GGAGAAACTT

CTTCGACAAA GCAAAACTCT GGTGATGAAA GTTCAAGTGG

AATTAAAGGT AGTGAAAAGT TTGATGAGGA TATGAGTGGT

ATGCCAGAAC CACCTGAGGG AATGGATGGT AAAATGCCAC

CAGGAATGGG TAATATGGAT AAGGGAGATA TGAATGGTAA

AAATGGCAAT ATGAATATGG ATAGAAATCA AGATAATCCA

AGAGAAGCTG GAGGTTTTGG CAATAGAGGA GGAGGCTCTG

TGAGTAAAAC AACAACATAC TTC.
```

The translated amino acid sequence of CD1021 fragment (505 to 604 amino acid residues) in plasmid pCD1021-Fr3-1 is:

(SEQ ID NO: 48)
```
MSKTIKSQLSGETSSTKQNSGDESSSGIKGSEKFDEDMSGMPEPPEGMDG

KMPPGMGNMDKGDMNGKNGNMNMDRNQDNPREAGGFGNRGGGSVSKTTTY

F.
```

Example 17

Expression of C. difficile ATCC 9689 CD1021 Clones

The recombinant plasmid pCD1021-2, obtained in Example 16, and the expression vector pET21-a(+) (Novagen, Madison, Wis.) were separately cut with the restriction enzymes NheI and XhoI (New England Biolabs, Ipswich, Mass.) according to manufacturer's instructions. The restriction enzyme-digested pCD1021-2 DNA was run on an agarose gel (0.8%) and the full-length CD1021 fragment was purified from the gel using Qiaquick gel extraction kit (Qiagen). The resultant fragment (1917 bp) was ligated into the restriction enzyme-digested expression vector pET21-a(+) using T4 DNA ligase (Invitrogen) according to manufacturer's instructions.

The ligated mixture was used to transform TOP10 chemically competent E. coli cells and plated on LB Agar with ampicillin (50 µg/ml). The plates were incubated at 37° C. for 12 to 16 hours and the recombinant clones were picked and grown in LB with ampicillin (100 µg/ml) for 16 hours at 37° C. The plasmid was isolated from these cultures by miniprep using alkaline lysis protocol (Miniprep kit, Qiagen) and the plasmids were cut with NheI and XhoI and analyzed by agarose gel. The clones having the full-length CD1021 insert were selected and tested for expression of proteins according to manufacturer's instruction.

Similarly, the fragment 1, fragment 2, and fragment 3 of clones CD1021-Fr1-1, CD1021-Fr2-2, and CD1021-Fr3-1 obtained in Example 16, were restriction digested with NheI and XhoI and cloned into NheI/XhoI restricted pET21a+. The recombinant clones were picked and analyzed as described above. The clones having the inserts were selected and tested for expression of proteins according to manufacturer's instruction.

The recombinant clones were transformed into competent cells of BLR(DE3) and plated on LB Agar with ampicillin (50 µg/ml). The plates were incubated at 37° C. for 12 to 16 hours. Several colonies were picked and grown in 5 ml of LB with ampicillin (100 µg/ml) for 16 hours at 37° C. The overnight grown clones were diluted 1:100 into 5 ml LB with ampicillin (100 µg/ml) and grown to an OD600 of 0.6 to 0.7. The clones were induced with 0.4 mM isopropyl β-D-1-thiogalactopyranoside (IPTG; Sigma, St. Louis, Mo.) for 3 hrs either at 37° C. or 15° C. using Lab-Line MaxQ 4000 Incubated and Refrigerated Shakers (Barnstead International, Dubuque, Iowa).

The induced cells were spun at 5000 rpm at 4° C. for 10 min and resuspended in 1 ml of 0.1 mM TRIS-HCl buffer, pH 8.0. The cells were sonicated using Branson Digital Sonifier model S-250D (Branson, Danbury, Conn.) using ⅛ inch tapered microtip for 10 sec to lyse the cells. The cell extracts were analyzed by SDS-PAGE. The gels were stained with Coomassie blue and the induced cells showed better expression of recombinant protein of expected molecular weight at 15° C. than at 37° C.

Example 18

Cloning and Sequencing Amidase (CD1036) from C. difficile ATCC 9689

A putative N-acetylmuramoyl-L-alanine amidase cell surface protein coding sequence was amplified by PCR using a forward primer with NcoI site (5'-AATCCATG G TAAGTAAGGAGATTAATATG-3') (SEQ ID NO:34), a reverse primer with XhoI site (5'-TTCCTCGAGTTTTAATGAATCTTCTATTCC-3') (SEQ ID NO:35) and genomic DNA from C. difficile ATCC strain 9689 as the template. A stop codon was removed from the reverse primer to facilitate addition of 6-HIS tag to the end of the sequence. The resulting fragment size was 2045 bp.

Similarly, the region corresponding to amino acid residues 294 to 393 of the putative N-acetylmuramoyl-L-alanine amidase cell surface protein of C. difficile 630 (SEQ ID NO:6) was amplified using genomic DNA from ATCC strain 9689 as the template with a forward primer with NcoI site (5'-AGG CCA TGGATAAAAATCATGATGTGGAA-3') (SEQ ID NO:36) and a reverse primer with XhoI site (5'-TTTCTCGAGGTTTGCATTTG TTTCGTGTCT-3') (SEQ ID NO:37). The resulting fragment size was 317 bp and included an ATG initiation codon.

The resultant PCR fragments were cloned using Zero Blunt TOPO PCR Cloning Kit (Invitrogen, San Diego, Calif.) and recombinant clones sequenced, using the procedures described in Example 16. Three clones were characterized for each of the two cloning reactions. For the 2045 bp CD1036 coding sequence, the three clones were pCD1036-1, pCD1036-2, and pCD1036-3. For fragment 1, the three clones were pCD1036-Fr1-1, pCD1036-Fr1-2, and pCD1036-Fr1-3.

The nucleotide sequence of C. difficile ATCC 9689 CD1036 fragment in plasmid pCD1036-2 is:

(SEQ ID NO: 43)
```
ATGGTAAGTA AGGAGATTAA TATGAGAAGA AATACAAAAT

TATTAACAAC AGGGATTCTT TCAATGGCAA TCGTCGCACC

TACAATGGCA TTTGCTACTG AATCTAATGC TATGGAAAAT

AACGCTGATT TAAATATAAA CTTAGAGAAA AAAAGTATCG

TTTTAGGTAG CAAATCAAAA GTTAGTGTCA AATTTAAAGA

AAAACCAGAT GCAGATAGCA TTAcATTAAA GTATAAATGC
```

-continued

```
TATGACATGC CATTGAATAC AACTCTAAAT TACAATCAAT

CAACTGGGGC ATATGAAGGA ACTATCAATT ATAACCAAGA

CCCAGAATAT CTAAATGTTT GGCAACCACA AGGGATAACA

ATAAACAGCA AAAATAATCa TAAAACTTTA AACAGACAAG

ACCTAGAAAA GCTGGGATTA AATTTAAAAG ACTATAATGT

AACACAGGAA TGTATAATTG AAGATATAAC TTCTAGAAAA

GATGTAAATA AATATTTGAG AAAAACTTCT TCACCTATTA

CAGAACTTAC AGGAAGTGAT AGATATGAAA CAGCAGTTAA

AATAAGTAAA GAGGGCTGGA AAAATGGTTC AGATAAGGTA

GTTATAATAA ATGGGATGT AAGTATAGAT GGCATTATAT

CAACTCCACT GGCAACCACA TATAATGCAC AATACTTTT

GGTTGAAAAA AACAATGTAC CTAATAGTGT AAAATCAGAA

TTAAAGCGCC TAAACCCTAA AGATATAATT ATAATTGGAG

ATGAGAATGC TATTTCTAAA ACTACTGCTA ATCAAATTAA

ATCAACTGTA AATGCTAGTC AAACACGTTT AAATGGTTCT

AATAGATATG AGACATCTTT ATTGATAGCA AAGGAAATAG

ATAAAAATCA TGATGTGGAA AAAGTATACA TAACAAATGC

TAATGGCGGA GAAGTGGATG CACTTACTAT AGCAGCAAAA

GCAGGTCAAG ACAAGCAACC AATTATATTA ACTGATAAAG

ATAGTATTAC AGACAATACA TATAAATGGT TAAAGAGTGA

GGATTTACAA AATGCTTATT TTATAGGTGG TCCTCAAATG

ATATCAACAA ATGTTATAAA TAAGGTAAAT GGAATAACTA

AAGATAGTGT TACTAATAAT AGAGTATACG GAGCAGATAG

ACACGAAACA AATGCAAACG TAATAAAAAA ATTCTATACA

GATGATGAGT TAGAGGCTGT TTTAGTAGCT AAATCAGATG

TACTTGTTGA TGCTTTAGCA GCAGGTCCAT GGCTGCGAA

CTTAAAATCT CCAATACTTA TAACACCAAA GACGTATGTA

TCTGCATACC ATAAAGATAA TTTAGAAGCT AAATCAGCTA

ATAAGGTATA CAAAATAGGA GGAGGATTGA CTTCTAAGGT

AATGAGCTCT ATAGCATCAT CATTATCTAA ACACAATACG

ACTCCAACAG AACCAGGAAA TAGTGGGGGC AAGACAGTTA

TGATTGACCC AGGGCATGGT GGTTCAGCAC CTGGAAATTC

ATCTGGAGGA ATGATTGAAA AGATTACAA TTTAAATACT

TCACTTGCAA CAACTGAATA TTTACGTTCA AAGGGATTCA

ATGTAATAAT GACAAGAGAC ACAGATAAGA CTTTATCTCT

TGGAAATAGA ACTGCTCTAT CTAATTCATT GAAACCAGAT

TTATTTACAA GTACACATTA TAATGGCTCA ACTAATAAAC

AAGGTCATGG TGTAGAAGTA TTTTATAAGC TTAAAGATAA

AAATGGAGGG ACTACTAAAA CTGTAGCTAC CAATATATTA

AATAGAATTT TAGAGAAATT TAAACTTACA AATAGAGGTA

TAAAAACAAG AGTACTTCCT AGTGATTCTA CAAAAGATTA

TTTATACGTT TTAAGAAGTA ATGATATGCC AGCTGTACTT

GTAGAATGTG CATTTTTGGA TAATGAAAAT GATATGAGTT

TAATAAACTC ATCTGCAAAA GTAAAAGAAA TGGGTACACA

AATAGGTAAA GGAATAGAAG ATTCATTAAA A.
```

The translated amino acid sequence of CD1036 fragment in plasmid pCD1036-2 is:

(SEQ ID NO: 49)
MVSKEINMRRNTKLLTTGILSMAIVAPTMAFATESNAMENNADLNINLEK
KSIVLGSKSKVSVKFKEKPDADSITLKYKCYDMPLNTTLNYNQSTGAYEG
TINYNQDPEYLNVWELQGITINSKNNHKTLNRQDLEKLGLNLKDYNVTQE
CIIEDITSRKDVNKYLRKTSSPITELTGSDRYETAVKISKEGWKNGSDKV
VIINGDVSIDGIISTPLATTYNAPILLVEKNNVPNSVKSELKRLNPKDII
IIGDENAISKTTANQIKSTVNASQTRLNGSNRYETSLLIAKEIDKNHDVE
KVYITNANGGEVDALTIAAKAGQDKQPIILTDKDSITDNTYKWLKSEDLQ
NAYFIGGPQMISTNVINKVNGITKDSVTNNRVYGADRHETNANVIKKFYT
DDELEAVLVAKSDVLVDALAAGPLAANLKSPILITPKTYVSAYHKDNLEA
KSANKVYKIGGGLTSKVMSSIASSLSKHNTTPTEPGNSGGKTVMIDPGHG
GSAPGNSSGGMIEKDYNLNTSLATTEYLRSKGFNVIMTRDTDKTLSLGNR
TALSNSLKPDLFTSIHYNGSTNKQGHGVEVFYKLKDKNGGTTKTVATNIL
NRILEKFKLTNRGIKTRVLPSDSTKDYLYVLRSNDMPAVLVECAFLDNEN
DMSLINSSAKVKEMGTQIGKGIEDSLK.

The nucleotide sequence of *C. difficile* ATCC 9689 CD1036 fragment (294 to 393 amino acid residues) in plasmid pCD1036-Fr1-1 is:

(SEQ ID NO: 44)
ATGGATAAAA ATCATGATGT GGAAAAAGTA TACATAACAA

ATGCTAATGG CGGAGAAGTG GATGCACTTA CTATAGCAGC

AAAAGCAGGT CAAGACAAGC AACCAATTAT ATTAACTGAT

AAAGATAGTA TTACAGACAA TACATATAAA TGGTTAAAGA

GTGAGGATTT ACAAAATGCT TATTTTATAG GTGGTCCTCA

AATGATATCA ACAAATGTTA TAAATAAGGT AAATGGAATA

ACTAAAGATA GTGTTACTAA TAATAGAGTA TACGGAGCAG

ATAGACACGA AACAAATGCA AAC.

The translated amino acid sequence 9689 CD1036 fragment (294 to 393 amino acid residues) in plasmid pCD1036-Fr1-1 is:

(SEQ ID NO: 50)

MDKNHDVEKVYITNANGGEVDALTIAAKAGQDKQPIILTDKDSITDNTYK

WLKSEDLQNAYFIGGPQMISTNVINKVNGITKDSVTNNRVYGADRHETNA

N.

Example 19

Expression of *C. difficile* ATCC 9689 Amidase Clones

The entire coding sequence of a putative N-acetylmuramoyl-L-alanine amidase cell surface protein from the recombinant plasmid pCD1036-2, as obtained in Example 18, and the expression vector pET21-d(+) (Novagen) were cut with the restriction enzymes NcoI and XhoI (New England Labs, Ipswich, Mass.) and cloned into pET21-d(+), using the procedures described in Example 17. Similarly, the fragment corresponding to amino acid residues 294 to 393 of the putative N-acetylmuramoyl-L-alanine amidase cell surface protein of *C. difficile* 630 (SEQ ID NO:6) from the recombinant plasmid pCD1036-Fr-1 was cut with the restriction enzymes NcoI and XhoI and cloned in to pET21-d(+), following the procedures described in Example 17. The recombinant clones were picked and analyzed as described in example 17. The clones having the inserts were selected and tested for expression of proteins according to manufacturer's instruction.

The recombinant clones were transformed into competent cells of BLR(DE3) and plated on LB Agar with ampicillin (50 µg/ml). Several colonies were picked and analyzed for protein expression as described in Example 17. The induced cells showed better expression of recombinant protein of expected molecular weight at 15° C. than at 37° C.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text

SEQ ID NO:1 hypothetical protein CD1021 of *C. difficile* strain 630

SEQ ID NO:2 residues 505-604 of hypothetical protein CD1021

SEQ ID NO:3 residues 203 to 217 hypothetical protein CD1021

SEQ ID NO:4 residues 333 to 347 hypothetical protein CD1021

SEQ ID NO:5 putative N-acetylmuramoyl-L-alanine amidase of *C. difficile* 630

SEQ ID NO:6 residues 294-393 of putative N-acetylmuramoyl-L-alanine amidase

SEQ ID NO:7 residues 582-596 of putative N-acetylmuramoyl-L-alanine amidase

SEQ ID NO:8 residues 64-78 of putative N-acetylmuramoyl-L-alanine amidase

SEQ ID NO:9 residues 30-120 of hypothetical protein CD1021

SEQ ID NO:10 residues 194-293 of hypothetical protein CD1021

SEQ ID NO:11-12 Amino acid sequence encoded in genome of *C. difficile* QCD-32g58

SEQ ID NO:13-14 Genomic sequence from *C. difficile* QCD-32g58

SEQ ID NO:15 Genomic sequence from *C. difficile* QCD-66c26

SEQ ID NO:16-17 Amino acid sequence encoded in genome of *C. difficile* strain 630

SEQ ID NO:18-20 Amino acid sequence encoded in genome of *C. difficile* QCD-32g58

SEQ ID NO:21 Translated amino acid sequence of *C. difficile* QCD-32g58

SEQ ID NO:22 Translated amino acid sequence of *C. difficile* QCD-32g58 genomic sequence SEQ ID NO:23 Translated amino acid sequence of *C. difficile* QCD-66c26

SEQ ID NO:24-37 Synthetic oligonucleotide primers

SEQ ID NO:38 Consensus sequence

SEQ ID NO:39-44 Genomic sequence from *C. difficile* ATCC 9689

SEQ ID NO:45-50 Translated amino acid sequence of *C. difficile* ATCC 9689

---

What is claimed is:

1. A method of detecting the presence of a *Clostridium difficile* spore in a sample, the method comprising contacting the sample with an isolated antibody that binds to a *Clostridium difficile* spore, wherein the isolated antibody binds to hypothetical protein CD1021 of *C. difficile* strain 630 having SEQ ID NO: 1.

2. A method of detecting the presence of a *Clostridium difficile* spore in a sample, the method comprising contacting the sample with at least two isolated antibodies or antigen-binding fragments thereof, wherein each isolated antibody binds to a distinct antigenic epitope of the *C. difficile* spore, wherein a first isolated antibody or antigen-binding fragment thereof binds to hypothetical protein CD1021 of *C. difficile* strain 630 having SEQ ID NO: 1, and wherein a second isolated antibody or antigen-binding fragment thereof binds to putative N-acetylmuramoyl-L-alanine amidase protein of *C. difficile* strain 630 having SEQ ID NO: 5.

3. A method of detecting the presence of a *Clostridium difficile* spore in a sample, the method comprising:
contacting the sample with a first isolated antibody or antigen-binding fragment thereof, wherein the first isolated antibody binds to a first antigenic epitope of the *C. difficile* spore; and
contacting the sample with a second isolated antibody or antigen-binding fragment thereof, wherein the second isolated antibody binds to a second antigenic epitope of the *C. difficile* spore;
wherein the first isolated antibody or antigen-binding fragment thereof binds or the second isolated antibody or antigen-binding fragment thereof binds to hypothetical protein CD1021 of *C. difficile* strain 630 having SEQ ID NO: 1.

* * * * *

UNITED STATES PATENT AND TRADEMARK OFFICE
CERTIFICATE OF CORRECTION

PATENT NO. : 8,697,374 B2
APPLICATION NO. : 12/919254
DATED : April 15, 2014
INVENTOR(S) : Rajagopal et al.

It is certified that error appears in the above-identified patent and that said Letters Patent is hereby corrected as shown below:

Title page 2
Item [56] References Cited under OTHER PUBLICATIONS
Line 17, "Colstridium" should read --Clostridium--.
Line 20, "Microbiologica;" should read --Microbiologcal;--.

Title page 3
Item [56] References Cited under OTHER PUBLICATIONS
Line 34, "Mannalian" should read --Mammalian--.

In the Specification

Column 1
Line 19, "pseudomembraneous" should read --pseudomembranous--.

Column 5
Line 55, "An''''''" should read --An "X"--.

Column 8
Line 40, "pseudomembraneous" should read --pseudomembranous--.
Line 53, "QCD-32$_g$58" should read --QCD-32$_g$58.--.

Column 20
Line 19, "lanthanate" should read --lanthanide--.
Line 20, "lanthanate" should read --lanthanide--.

Column 21
Line 48, "may by" should read --may be--.

Signed and Sealed this
Fifth Day of May, 2015

Michelle K. Lee
*Director of the United States Patent and Trademark Office*

Column 27
Line 25, "of the of the" should read --of the--.

Column 29
Line 7, "of the of the" should read --of the--.